(12) United States Patent
Alsharifi et al.

(10) Patent No.: US 10,251,947 B2
(45) Date of Patent: Apr. 9, 2019

(54) INFLUENZA VACCINES

(71) Applicant: Gamma Vaccines Pty Limited, Forrest (AU)

(72) Inventors: Mohammed Alsharifi, Gilles Plains (AU); Arno Mullbacher, Curtin (AU)

(73) Assignee: Gamma Vaccines Pty Limited, Forrest (AU)

( * ) Notice: Subject to any disclaimer, the term of this patent is extended or adjusted under 35 U.S.C. 154(b) by 0 days.

(21) Appl. No.: 14/744,924

(22) Filed: Jun. 19, 2015

(65) Prior Publication Data

US 2015/0283224 A1   Oct. 8, 2015

Related U.S. Application Data

(63) Continuation of application No. 13/056,932, filed as application No. PCT/AU2009/000983 on Jul. 31, 2009, now abandoned.

(60) Provisional application No. 61/085,802, filed on Aug. 1, 2008.

(51) Int. Cl.

| *A61K 39/145* | (2006.01) |
| *C07K 16/10* | (2006.01) |
| *C12N 7/00* | (2006.01) |
| *A61K 39/12* | (2006.01) |
| *A61K 39/00* | (2006.01) |

(52) U.S. Cl.
CPC .......... *A61K 39/145* (2013.01); *A61K 39/12* (2013.01); *C07K 16/1018* (2013.01); *C12N 7/00* (2013.01); *A61K 2039/5252* (2013.01); *A61K 2039/543* (2013.01); *A61K 2039/545* (2013.01); *A61K 2039/58* (2013.01); *A61K 2039/70* (2013.01); *C12N 2760/16134* (2013.01); *C12N 2760/16161* (2013.01); *C12N 2760/16163* (2013.01); *C12N 2760/16171* (2013.01); *C12N 2760/16234* (2013.01)

(58) Field of Classification Search
None
See application file for complete search history.

(56) References Cited

U.S. PATENT DOCUMENTS

| 3,259,546 A | 7/1966 | Polley |
| 3,557,370 A | 1/1971 | Piekenbrock et al. |
| 3,567,938 A | 3/1971 | Piekenbrock |

(Continued)

FOREIGN PATENT DOCUMENTS

| EP | 0399843 | 11/1990 |
| EP | 1216053 | 6/2002 |

(Continued)

OTHER PUBLICATIONS

Lowy, et al. Comparison of gamma and neutron radiation inactivation of influenza A virus. Antivir. Res. 2001; 52: 261-273.*

(Continued)

*Primary Examiner* — Janet L Andres
*Assistant Examiner* — Stuart W Snyder
(74) *Attorney, Agent, or Firm* — Kilpatrick Townsend & Stockton LLP

(57) ABSTRACT

The invention relates to a method for the treatment or prevention of an influenza virus infection in a subject, the method comprising administering to the subject a therapeutically effective amount of a gamma-irradiated influenza virus.

10 Claims, 30 Drawing Sheets

(56) References Cited

U.S. PATENT DOCUMENTS

| | | | |
|---|---|---|---|
| 5,698,433 | A | 12/1997 | Kistner et al. |
| 5,753,489 | A | 5/1998 | Kistner et al. |
| 5,824,536 | A | 10/1998 | Webster et al. |
| 6,146,873 | A | 11/2000 | Kistner et al. |
| 6,344,354 | B1 | 2/2002 | Webster et al. |
| 6,372,223 | B1 | 4/2002 | Kistner et al. |
| 6,455,298 | B1 | 9/2002 | Groner et al. |
| 6,569,458 | B1 | 5/2003 | Gombotz et al. |
| 6,673,591 | B2 | 1/2004 | Lau |
| 6,686,190 | B2 | 2/2004 | Lau |
| 6,825,036 | B2 | 11/2004 | Keiichi et al. |
| 6,951,752 | B2 | 10/2005 | Manfred et al. |
| 7,029,678 | B2 | 4/2006 | Momin et al. |
| 7,132,271 | B2 | 11/2006 | Lau |
| 7,192,759 | B1 | 3/2007 | Pau et al. |
| 7,270,990 | B2 | 9/2007 | Williams et al. |
| 2011/0150926 | A1 | 6/2011 | Alsharifi et al. |

FOREIGN PATENT DOCUMENTS

| | | | | |
|---|---|---|---|---|
| WO | | 1994/000153 | | 1/1994 |
| WO | | 1994/021797 | | 9/1994 |
| WO | | 1995/017210 | | 6/1995 |
| WO | | 1996/002555 | | 2/1996 |
| WO | | 1996/033739 | | 10/1996 |
| WO | | 2002/067983 | | 9/2002 |
| WO | | 2005/024039 | | 3/2005 |
| WO | | 2005/113756 | | 12/2005 |
| WO | | 2006/108846 | | 10/2006 |
| WO | | 2007/006939 | | 1/2007 |
| WO | WO 2007/107585 | A1 * | 9/2007 | ........... A61K 39/145 |
| WO | | 2008/017956 | A2 | 2/2008 |
| WO | | 2008/073490 | A1 | 6/2008 |
| WO | WO 2008/073490 | | * 6/2008 | |
| WO | | 2010/012045 | | 5/2010 |

OTHER PUBLICATIONS

Morenweiser Downstream processing of viral vectors and vaccines. Gene Ther. 2005; 12: S103-S110.*
Müllbacher et al. Gamma-irradiated influenza A virus can prime for a cross-reactive and cross-protective immune response against influenza A viruses. Immunol. Cell Biol. 1988; 66: 153-157.*
Furuya et al. Cytotoxic T Cells Are the Predominant Players Providing Cross-Protective Immunity Induced by γ-Irradiated Influenza A Viruses. J. Virol. 2010; 84(9): 4212-4221.*
Furuya et al. Effect of inactivation method on the cross-protective immunity induced by whole 'killed' influenza A viruses and commercial vaccine preparations. J. Gen. Virol. 2010; 91: 1450-1460.*
McGill, J., et al., "Cutting Edge: Contribution of Lung-Resident T Cell Proliferation to the Overall Magnitude of the Antigen-Specific CD8 T Cell Response in the Lungs following Murine Influenza Virus Infection," J. Immunol, vol. 183, 2009, pp. 4177-4181.
Stambas, J., et al., "Killer T cells in influenza," Pharmacology & Therapeutics, vol. 120, 2008, pp. 186-196.
Ada, G. L. & Jones, P. D. (1986). The immune response to influenza infection. Curr Top Microbiol Immunol 128, 1-54.
Adachi Targeted disruption of the MyD88 gene results in loss of IL-1- and IL-18-mediated function. Immunity, 1998. 9(1): p. 143-50.
Alexopoulou, L., Recognition of double-stranded RNA and activation of NF-kappaB by Toll-like receptor 3. Nature, 2001. 413(6857): p. 732-8.
Alsharifi, M., A. Mullbacher, and M. Regner, Interferon type I responses in primary and secondary infections. Immunol Cell Biol, 2008.
Alsharifi, M., et ah. Exhaustion of type I interferon response following an acute viral infection. J Immunol, 2006. 177(5): p. 3235-41.
Alsharifi, M., et al. Type I interferons trigger systemic, partial lymphocyte activation in response to viral infection. J Immunol, 2005. 175(7): p. 4635-40.

Anders, E.M., A.A. Scalzo, and D.O. White, Mitogenic activity of influenza virus and haemagglutinin. Vaccine, 1985. 3(3 Suppl): p. 241-4.
Anders, E.M., et ah. Relationship between mitogenic activity of influenza viruses and the receptor-binding specificity of their hemagglutinin molecules. J Virol, 1986. 60(2): p. 476-82.
Article in The Canberra Times (May 2007).
Asselin-Paturel, C., et al., Mouse type I IFN-producing cells are immature APCs with plasmacytoid morphology. Nat Inmrunol, 2001. 2(12): p. 1144-50.
Barber, B.H., "The immunotargeting approach to adjuvant-independent subunit vaccine design," Immunology, vol. 9, pp. 293-301, (1997).
Barchet, W., et ah. Dendritic cells respond to influenza virus through TLR7- and PKR-independent pathways. Eur J Immunol, 2005. 35(1): p. 236-42.
Barry, D. W., Mayner, R. E., Staton, E., Dunlap, R. C., Rastogi, S. C., Hannah, J. E., Blackburn, R. J., Nortman, D. F. & Graze, P. R. (1976). Comparative trial of influenza vaccines. I. Immunogenicity of whole virus and split product vaccines in man. Am J Epidemiol 104, 34-46.
Barry, D. W., Staton, E. & Mayner, R. E. (1974). Inactivated influenza vaccine efficacy: diminished antigenicity of split-product vaccines in mice. Infect Immun 10, 1329-1336.
Bennink et al, 1978, "Influenzal pneumonia: early appearance of cross-reactive T cells in lungs of mice primed with heterologous type A viruses", Immunology 35: 503-509.
Bieback, K., Hemagglutinin protein of wild-type measles virus activates toll-like receptor 2 signaling. J Virol, 2002. 76(17): p. 8729-36.
Blazevic, V., Trubey, C. M. & Shearer, G. M. (2000). Comparison of in vitro immunostimulatory potential of live and inactivated influenza viruses. Hum Immunol 61, 845-849.
Boehme, K.W., M. Guerrero, and T. Compton. Human cytomegalovirus envelope glycoproteins B and H are necessary for TLR2 activation in permissive cells. J Immunol, 2006. 177(10): p. 7094-102.
Braciale, T. J. & Yap, K. L. (1978). Role of viral infectivity in the induction of influenza virus-specific cytotoxic T cells. J Exp Med 147, 1236-1252.
Braun, D., I. Caramalho, and J. Demengeot, IFN-alpha/beta enhances BCR-dependent B cell responses. Int Immunol, 2002. 14(4): p. 411-9.
Budimir, N., "Heterosubtypic cross-protection induced by whole inactivated influenza virus vaccine in mice; influence of the route of vaccine administration," Influenza and Other Respiratory Viruses, vol. 7, Issue 6, pp. 1202-1209, Nov. 2013.
Budowsky, E. I., Bresler, S. E., Friedman, E. A. & Zlieleznova, N. V. (1981). Principles of selective inactivation of viral genome. I. UV-induced inactivation of influenza virus. Arch Virol 68, 239-247.
Budowsky, E. I., Friedman, E. A., Zheleznova, N. V. & Noskov, F. S. (1991). Principles of selective inactivation of viral genome. VI. Inactivation of the infectivity of the influenza virus by the action of beta-propiolactone. Vaccine 9, 398-402.
Budowsky, E. I., Smirnov Yu, A. & Shenderovich, S. F. (1993). Principles of selective inactivation of viral genome. VIII. The influence of beta-propiolactone on immunogenic and protective activities of influenza virus. Vaccine 11, 343348.
Carrasquillo (2001), "Reduction of structural perturbations in bovine serum albumin by non-aqueous microencapsulation", J Pharm Pharmacol., 53:115-120.
Carrasquillo (2001); "Non-aqueous encapsulation of excipient-stabilized spray-freeze dried BSA into poly(lactide-co-glycolide) microspheres results in release of native protein", J Control Release, 76:199-208.
Chinese Application No. 200980138757.4 Office Action dated Nov. 15, 2012.
Chinese Application No. 200980138757.4 Office Action dated Oct. 11, 2013.
Cohn, M. and R.E. Langman, The protection: the unit of humoral immunity selected by evolution. Immunol Rev, 1990. 115: p. 11-147.

(56) References Cited

OTHER PUBLICATIONS

Costantino et al., (2002), "Protein spray freeze drying. 2. Effect of formulation variables on particle size and stability", J Pharm Sci., 91:388-395.
Costantino, et al., (2000), "Protein spray-freeze drying. Effect of atomization conditions on particle size and stability", Pharm Res. 17:1374-1383.
Cox et al., 1994, "An early humoral immune response in peripheral blood following parenteral inactivated influenza vaccination". Vaccine, 12:993-999.
De Benedictis, P., Beato, M. S. & Capua, I. (2007). Inactivation of avian influenza viruses by chemical agents and physical conditions: a review. Zoonoses Public Health 54, 51-68.
De Flora, S. & Badolati, G. (1973a). Inactivation of A2-Hong Kong influenza virus by heat and by freeze-thawing. Comparison of untreated and gamma-irradiated preparations. Boll 1st Sieroter Milan 52, 293-305.
De Flora, S. & Badolati, G. (1973b). Thermal inactivation of untreated and gamma-irradiated A2-Aichi-2-68 influenza virus. J Gen Virol 20, 261-265.
Degiorgi "Cryo-gamma radiation inactivation of bovine herpesvirus type 1," Radiation Phys. Chem. 1999; 55: 469-471.
Diebold, S.S., et ah. Innate antiviral responses by means of TLR7-mediated recognition of single-stranded RNA. Science, 2004. 303(5663): p. 1529-31.
Diebold, S.S., et ah. Viral infection switches non-plasmacytoid dendritic cells into high interferon producers. Nature, 2003. 424(6946): p. 324-8.
EP09802286.6 Extended EP Search Report dated Oct. 12, 2012.
Fisher "Average protein density is a molecular-weight-dependent function," Prot. Sci. 2004; 13:2825-2828.
Flynn, 1999, "In vivo proliferation of naive and memory influenza specific CD8+ T cells" PNAS, 96(15): 8597-8602
Fridman, A. L., Ermolaev, A. I., Bichurina, M. A. & Chubarova, N. I. (1979). [Effect of gamma radiation on the biological characteristics of purified influenza virus]. Tr Inst Im Pastera 52, 135-139.
Geeraedts, F., Superior immunogenicity of inactivated whole virus H5N1 influenza vaccine is primarily controlled by Toll-like receptor signalling. PLoS Pathog, 2008. 4(8): p. eI0Q00138.
Georgel, P., et al.. Vesicular stomatitis virus glycoprotein G activates a specific antiviral Toll-like receptor 4-dependent pathway. Virology, 2007. 362(2): p. 304-13.
Goldstein, M. A. & Tauraso, N. M. (1970). Effect of formalin, betapropiolactone, merthiolate, and ultraviolet light upon influenza virus infectivity chicken cell agglutination, hemagglutination, and antigenicity. Appl Microbiol 19, 290-294.
Guillot, L., Involvement of toll-like receptor 3 in the immune response of lung epithelial cells to double-stranded RNA and influenza A virus. J Biol Chem, 2005. 280(7): p. 5571-80.
Harmon et al, 1988, "Antibody Response in Humans to Influenza Virus Type B Host-Cell-Derived Variants after Vaccination with Standard (Egg-Derived) Vaccine or Natural Infection", J. Clin. Microbiol., 26:333-337.
Heine, H.G., et al, 2007 "Rapid detection of highly pathogenic avian influenza H5N1 virus by TaqMan reverse transcriptase-polymerase chain reaction" Avian Dis. 51: 370-372.
Higashi, Y. and Y. Sokawa, Microinjection of interferon and 2',5'-oligoadenylate into mouse L cells and their effects on virus growth. J Biochem, 1982. 91(6): p. 2021-8.
Hoshino, K., et al.. Cutting edge: Toll-like receptor 4 (TLR4)-deficient mice are hyporesponsive to lipopolysaccharide: evidence for TLR4 as the LPS gene product. J Immunol, 1999. 162(7): p. 3749-52.
Huang, S., et al.. Immune response in mice that lack the interferon-gamma receptor. Science, 1993. 259(5102): p. 1742-5.
Huez, G., M. Silhol, and B. Lebleu, Microinjected interferon does not promote an antiviral response in Hela cells. Biochem Biophys Res Commun, 1983. 110(1): p. 155-60.

IAEA (1973). The Manual on Radiation Sterilization of Medical and Biological Material: The technical reports series. 149: 65-70,. Vienna: International Atomic Energy Agency.
Ichinohe, T. et al, "Cross-protection against H5N1 influenza virus infection is afforded by intranasal inoculation with seasonal trivalent inactivated influenza vaccine," J Infect Dis 196, 1313-1320 (2007).
Indonesian Application No. W-00201100673 Corrected First Examination Report, no date available.
Indonesian Application No. W-00201100673 First Examination Report, no date available.
International Preliminary Report on Patentability issued in Parent International Appl. No. PCT/AU2009/000983 dated Jun. 17, 2010.
International Search Report issued in Parent International Appl. No. PCT/AU2009/000983 dated Sep. 24, 2009.
Jackson, V. (1978). Studies on histone organization in the nucleosome using formaldehyde as a reversible cross-linking agent. Cell 15, 945-954.
Japanese Application No. 2011-520282 Notice of Reasons for Rejection dated Jul. 16, 2013.
Jiang, Z., et al., CD14 is required for MyD88-independent LPS signalling. Nat Immunol, 2005. 6(6): p. 565-70.
Kato, H., Differential roles of MDA5 and RIG-I helicases in the recognition of RNA viruses. Nature, 2006. 441(7089): p. 101-5.
Khorlin et al., (1970), "Synthetic inhibitors of Vibrio cholerae neuraminidase and neuraminidases of some influenza vu-us strains", FEES Lett., 8:17-19.
Koller, B.H., Normal development of mice deficient in beta 2M, MHC class I proteins, and CD8+ T cells. Science, 1990. 248(4960): p. 1227-30.
Kulevich, E. E. & Kosiakov, P. N. (1974). [Immunogenic properties of A2/Hongkong/I/68 influenza virus inactivated with gamma rays]. Vopr Virusol, 696-700.
Kuniagai, Y., Alveolar macrophages are the primary interferon-alpha producer in pulmonary infection with RNA viruses. Immunity, 2007. 27(2): p. 240-52.
Kurt-Jones, E.A., Pattern recognition receptors TLR4 and CD14 mediate response to respiratory syncytial virus. Nat Immunol, 2000. 1(5): p. 398-401.
Lauffer "Biophysical properties of preparations of Pr8 influenza virus," J. Expt. Med. 1944; 531-548.
Le Goffic, R., Cutting Edge: Influenza A virus activates TLR3-dependent inflammatory and RIG-I-dependent antiviral responses in human lung epithelial cells. J Immunol, 2007. 178(6): p. 3368-72.
Lee, H.K., Autophagy-dependent viral recognition by plasmacytoid dendritic cells. Science, 2007. 315(5817): p. 1398-401.
Lidbury "Studies on the igA-independent immunological responses in mice to influenza virus challenge after oral vaccination with irradiated whole virus and an erythrocyte complex," Immunology and Cell Biology 2000; 78, 149-155.
Lidbury, B. A., Grissell, T. V., Sizer, P. J., Pang, G. T., Clancy, R. & Cripps, A. W. (1997). Erythrocytes enhance the immunogenicity of oral vaccination with gamma irradiated influenza virus: increasing the dose of irradiation results in a significant diminution of lung IgA response. Vaccine 15, 1529-1537.
Liu Immune Responses Induced with Soluble Tachyzoite Antigen of Toxoplasma gondii in Mice by Various Routes, Chin J Biologicals, May 2008, 21(5): 398-400.
Longhi 2008, "Interleukin-6 Is Crucial for Recall of Influenza-Specific Memory CD4-t-T Cells", PLoS Pathog., 4(2): eI000006.
Louria, D.B. et al.. Studies on influenza in the pandemic of 1957-1958. II. Pulmonary complications of influenza. J Clin Invest, 1959. 38(1 Part 2): p. 213-65.
Lowy, R. J., Vavrina, G. A. & LaBarre, D. D. (2001). Comparison of gamma and neutron radiation inactivation of influenza A virus. Antiviral Res 52, 261-273.
Lund, J., et al.. Toll-like receptor 9-mediated recognition of Herpes simplex virus-2 by plasmacytoid dendritic cells. J Exp Med, 2003. 198(3): p. 513-20.
Lund, J.M., et al.. Recognition of single-stranded RNA viruses by Toll-like receptor 7. Proc Natl Acad Sci USA, 2004. 101(15): p. 5598-603.

(56) References Cited

OTHER PUBLICATIONS

Maa (1999), "Protein inhalation powders: spray drying vs spray freeze drying", Pharm Res, 16:249-254.
Madsen, L., et al.. Mice lacking all conventional MHC class II genes. Proc Natl Acad Sci USA, 1999. 96(18): p. 10338-43.
Marshall-Clarke, S., et al.. Influenza H2 haemagglutinin activates B cells via a MyD88-dependent pathway. Eur J Immunol, 2006. 36(1): p. 95-106.
Martinson, H. G., True, R., Lau, C. K. & Mehrabian, M. (1979). Histon-histone interactions within chromatin. Preliminary location of multiple contact sites between histones 2A, 2B, and 4. Biochemistry 18, 1075-1082.
Mazanec, M. B., Kaetzel, C. S., Lamm, M. E., Fletcher, D. & Nedrud, J. G. (1992). Intracellular neutralization of virus by immunoglobulin A antibodies. Proc Natl Acad Sci U S A 89, 6901-6905.
Mazanec, M. B., Coudret, C. L. & Fletcher, D. R. (1995a). Intracellular neutralization of influenza virus by immunoglobulin A antihemagglutinin monoclonal antibodies. J Virol 69, 1339-1343.
Mazanec, M. B., Kaetzel, C. S., Lamm, M. E., Fletcher, D., Peterra, J. & Nedrud, J. G. (1995b). Intracellular neutralization of Sendai and influenza viruses by IgA monoclonal antibodies. Adv Exp Med Biol 371A, 651-654.
Melchjorsen, J., et al., Activation of innate defense against a paramyxovirus is mediated by RIG-I and TLR7 and TLR8 in a cell-type-specific manner. J Virol, 2005. 79(20): p. 12944-51.
Migunov, A. L. "Physicochemical characteristics of an influenza virus population inactivated by gamma rays," Radiobiologiia 26, 647-651 (1986).
Miller, J.L. and E.M. Anders, Virus-cell interactions in the induction of type 1 interferon by influenza virus in mouse spleen cells. J Gen Virol, 2003. 84(Pt 1): p. 193-202.
Morens, D.M., J.K. Taubenberger, and A.S. Fauci, Predominant role of bacterial pneumonia as a cause of death in pandemic influenza: implications for pandemic influenza preparedness. J Infect Pis, 2008. 198(7): p. 962-70.
Morenweiser, R. Downstream processing of viral vectors and vaccines. *Gene Therapy* (2005) 12, S103-S110.
Mullbacher 1999, "Spontaneous mutation at position 114 in H-2Kd affects cytotoxic T cell responses to influenza virus infection" Eur. J. Immunol. 29, 1228-1234.
Mullbacher and Tha Hla, 1993, "In vivo administration of major histocompatibility complex class I-specific peptides from influenza virus induces specific cytotoxic T cell hyporesponsiveness", Eur. J. Immunol., 23, 2526-2531.
Mullbacher, 1984, "Hyperthermia and the generation and activity of murine influenza-immune cytotoxic T cells in vitro", J. Virol., 52, 928-931.
Mullbacher, A., Ada, G. L. & Hla, R. T. (1988). Gamma-irradiated influenza A virus can prime for a cross-reactive and cross-protective immune response against influenza A viruses. Immunol Cell Biol 66 (Pt 2), 153-157.
Mullbacher, A., Hill, A. B., Blanden, R. V., Cowden, W. B., King, N. J. & Hla, R. T. (1991). Alloreactive cytotoxic T cells recognize MFIC class I antigen without peptide specificity. J Immunol 147, 1765-1772.
Mullbacher, A., Lobigs, M., Alsharifi, M. & Regner, M. (2006). Cytotoxic T-cell immunity as a target for influenza vaccines. Lancet Infect Pis 6, 255-256.
Muller, U., et al.. Functional role of type I and type II interferons in antiviral defense. Science, 1994. 264(5167): p. 1918-21.
Mutsch, (2004), "Use of the inactivated intranasal influenza vaccine and the risk of Bell's palsy in Switzerland", The New England journal of medicine, 350: 896-903.
Nguyen, H. H., Moldoveanu, Z., Novak, M. J., van Ginkel, F. W., Ban, E., Kiyono, H., McGhee, J. R. & Mestecky, J. (1999). Heterosubtypic immunity to lethal influenza A virus infection is associated with virus-specific CD8(+) cytotoxic T lymphocyte responses induced in mucosa-associated tissues. Virology 254, 50-60.
NHMRC website posting (Feb. 10, 2006).
NHMRC website posting (2006).
Noack, K., Tischner, H., Brauniger, S., Nordheim, W. & Pohl, W. D. (1986). [Long-term effect of oral immunization against influenza with a gamma ray inactivated vaccine in mice]. Z Erkr Atmungsorgane 166, 286-289.
O'Neill, L.A., K.A. Fitzgerald, and A.G. Bowie, The Toll-IL-1 receptor adaptor family grows to five members. Trends Immunol, 2003. 24(6): p. 286-89.
Ortbals, D. W. & Liebhaber, H. (1978). Comparison of immunogenicity of a whole virion and a subunit influenza vaccine in adults. J Clin Microbiol 8, 431434.
Palese, P. (2006). Making belter influenza virus vaccines? Emerg Infect Dis 12, 61-65.
Pang, G. T. A novel particulate influenza vaccine induces long-term and broad-based immunity in mice after oral immunization. Journal of Virology, 1992, 66(2): 1162-1170.
Pang, G. T., Clancy, R. L., O'Reilly, S. E. & Cripps, A. W. (1992). A novel particulate influenza vaccine induces long-term and broad-based immunity in mice after oral immunization. J Virol 66, 1162-1170.
Parish and Miillbacher, 1983, "Automated colorimetric assay for T cell cytotoxicity", J. Immunol Meth., 58: 225-237.
Perrin and Morgeaux, "Inactivation of DNA by beta-propiolactone," Biologicals, 1995; 23, 207-211.
Pichlmair, A., RIG-I-mediated antiviral responses to single-stranded RNA bearing 5'-phosphates. Science, 2006. 314(5801): p. 997-1001.
Poltorak, A., et al.. Defective LPS signaling in C3II/HeJ and C57BL/10ScCr mice: mutations in TIr4 gene. Science, 1998. 282(5396): p. 2085-8.
Polyanskaya, N. (1979). [Preparation of an influenza vaccine from allantoic viral cultures inactivated with UV irradiation]. Tr Inst Im Pastera 52, 107-110.
Pothlichet, J., M. Chignard, and M. Si-Tahar, Cutting edge: innate immune response triggered by influenza A virus is negatively regulated by SOCSI and SOCS3 through a RIG-PIFNARI-dependent pathway. J Immunol, 2008. 180(4): p. 2034-8.
Poumbourios, P., et al.. Direct role of viral hemagglutinin in B-cell mitogenesis by influenza viruses. J Virol, 1987. 61(1): p. 214-7.
Quah, B.J., et al.. Bystander B cells rapidly acquire antigen receptors from activated B cells by membrane transfer. Proc Natl Acad Sci USA, 2008. 105(11): p. 4259-64.
Quan, et al. Induction of Heterosubtypic immunity to influenza virus by intranasal immunization. J. Virol. 2008; 82(3): 1350-1359.
Rassa, J.C., et al.. Murine retroviruses activate B cells via interaction with toll-like receptor 4. Proc Natl Acad Sci USA, 2002. 99(4): p. 2281-6.
Rastogi, S.C., H.D. Hochstein, and E.B. Seligmann, Jr., Statistical determination of endotoxin content in influenza virus vaccine by the limulus amoebocyte lysate test. J Clin Microbiol, 1977. 6(2): p. 144-8.
Redfield, D. C., Richman, D. D., Oxman, M. N. & Kxonenberg, L. H. (1981). Psoralen inactivation of influenza and herpes simplex viruses and of virus-infected cells. Infect Immun 32, 1216-1226.
Riviere, I. and J. de Maeyer-Guignard, Alpha/beta interferons fail to induce antiviral activity from within the nucleus. J Virol, 1990. 64(5): p. 2430-2.
Rota 1987 "Comparison of the immune response to variant influenza type B hemagglutinins expressed in vaccinia virus". Virology, 161:269-75.
Rott, O. and E. Cash, Influenza virus hemagglutinin induces differentiation of mature resting B cells and growth arrest of immature WEHI-231 lymphoma cells. J Immunol, 1994. 152(11): p. 5381-91.
Rott, O., J. Charreire, and E. Cash, Influenza A virus hemagglutinin is a B cellsuperstimulatory lectin. Med Microbiol Immunol, 1996. 184(4): p. 185-93.
Russian Application No. 2011107757/15(010978) Office Action dated Jul. 17, 2012.
Salk, J. E. (1948). Reactions to concentrated influenza virus vaccines. J Immunol 58, 369-395.
Sanceau, J., Intracellular human ganmia-interferon triggers an antivual state in transformed murine L cells. Proc Natl Acad Sci USA, 1987. 84(9): p. 2906-10.

(56) References Cited

OTHER PUBLICATIONS

Sasaki 2007, "Comparison of the influenza virus-specific effector and memory B-cell responses to immunization of children and adults with live attenuated or inactivated influenza virus vaccines", J Virol. 2007; 81:215-28.
Sato (1983), "Separation and purification of the hemagglutinins from Bordetella pertussis", Infect. Immun., 41, 313-320.
Sato 1996, "Immunostimulatory DNA sequences necessary for effective intradermal gene immunization", Science, 273:352-354.
Scalzo, A.A. and E.M. Anders, Influenza viruses as lymphocyte mitogens. I. B cell mitogenesis by influenza A viruses of the H2 and H6 subtypes is controlled by the I-E/C subregion of the major histocompatibility complex. J Immunol, 1985. 134(2): p. 757-60.
Scalzo, A.A. and E.M. Anders, Influenza viruses as lymphocyte mitogens. II. Role of I-E molecules in B cell mitogenesis by influenza A viruses of the H2 and H6 subtypes. J Immunol, 1985. 135(5): p. 3524-9.
Sheffield, F.W., W. Smith, and G. Belyavin, Purification of influenza virus by red-cell adsorption and elution. Br J Exp Pathol, 1954. 35(3): p. 214-22.
Shinichi, Tamuma; Kurata, Takeshi "Nasal vaccine: Prevention of influenza" (1996) Igaku no Ayumi: Additional Volume, pp. 168-173.
Shiow, L.R., CD69 acts downstream of interferon-alpha/beta to inhibit SIPI and lymphocyte egress from lymphoid organs. Nature, 2006. 440(7083): p. 540-4.
Sokolov (1971), "Purification and concentration of influenza virus", Archiv für die gesarate Vlnisforschung, 35, 356-363.
Steven, A.C. and P.G. Spear, Biochemistry. Viral glycoproteins and an evolutionary conundrum. Science, 2006. 313(5784): p. 177-8.
Takada, A., Intranasal immunization with formalin-inactivated virus vaccine induces a broad spectrum of heterosubtypic inmiunity against influenza A virus infection in mice. Vaccine, 2003. 21(23): p. 3212-8.
Takada, A., Kuboki, N., Okazaki, K., Ninomiya, A., Tanaka, H., Ozaki, H., Itamura, S., Nishimura, H., Enami, M., Tashiro, M., Shortridge, K. F. & Kida, H. (1999). Avirulent Avian influenza virus as a vaccine strain against a potential human pandemic. J Virol 73, 8303-8307.
Takeuchi, O., et al.. Differential roles of TLR2 and TLR4 in recognition of gram-negative and gram-positive bacterial cell wall components. Immunity, 1999. 11(4): p. 443-51.
Tamura Superior cross-protective effect of nasal vaccination to subcutaneous inoculation with influenza hemagglutinin vaccine, Eur J Immunol, 1992, 22(2):477-81.
Thoelen, S., "A prophylactic hepatitis B vaccine with a novel adjuvant system". Vaccine (2001) 19:2400-2403.
Tomohiko, Kusuhara "Investigation on cross-protection effect by intranasal vaccination of inactivated influenza vaccine" (1991) Kurume University School of Medicine Magazine 54(1), 58-77.
Triantafilou, K. and M. Triantafilou, Coxsackievirus B4-induced cytokine production in pancreatic cells is mediated through toll-like receptor 4. J Virol, 2004. 78(20): p. 11313-20.
Tumpey, T. M., Renshaw, M., Clements, J. D. & Katz, J. M. (2001). Mucosal delivery of inactivated influenza vaccine induces B-cell-dependent heterosubtypic cross-protection against lethal influenza A H5N1 virus infection. J Virol 75, 5141-5150.
Uittenborgaard "Reactions of beta-propiolactone with nucleobase analogues, nucleosides and peptides: Implications for the inactivation of viruses," J. Biol. chem. 2011; 286:36198-36214.

Van Deusen (1983), "Micro neuraminidase-inhibition assay for classification of influenza A virus neuraminidases" Avian Pis., 27:745-50.
Vogt 2008, "Transcutaneous anti-influenza vaccination promotes both CD4 and CDS T cell immune responses in humans", J. Immunol., 180: 14821489.
Who (2005). Immunization against diseases of public health importance. In Fact sheets.
Will, A., Intracellular murine IFN-gamma mediates virus resistance, expression of oligoadenylate synthetase, and activation of ST AT transcription factors. J Immunol, 1996. 157(10): p. 4576-83.
Written Opinion issued in Parent International Appl. No. PCT/AU2009/000983 dated Sep. 11, 2009.
Yap 1977, "Cytotoxic T cells specific for influenza virus-infected target cells," Immunology, 32: 151-159.
Zuniga, E.I., et al.. Persistent virus infection inhibits type I interferon production by plasmacytoid dendritic cells to facilitate opportunistic infections. Cell Host Microbe, 2008. 4(4): p. 374-86.
Alsharifi, M., et al., "Intranasal Flu Vaccine Protective against Seasonal and H5N1 Avian Influenza Infections," PLoS ONE, vol. 4, Issue 4, Apr. 2009, e5336. doi:10.1371/journal.pone.0005336.
Ely, K., et al., "Memory T Cell Populations in the Lung Airways Are Maintained by Continual Recruitment," *The Journal of Immunology*, vol. 176, 2006, pp. 537-543.
Gebhardt, K., et al., "Memory T cells in nonlymphoid tissue that provide enhanced local immunity during infection with herpes simplex virus," *Nature Immunology*, vol. 10, No. 5, May 2009, pp. 524-530.
Hagenaars, N., et al., "Physicochemical and Immunological Characterization of N,N,N-Trimethyl Chitosan-Coated Whole Inactivated Influenza Virus Vaccine for Intranasal Administration," *Pharmaceutical Research*, vol. 26, No. 6, Jun. 2009, pp. 1353-1364.
Hasegawa, H., et al., "Development of mucosal adjuvants for intranasal vaccine for H5N1 infl uenza viruses," *Therapeutics and Clinical Risk Management*, vol. 5, 2009, pp. 125-132.
Kedzierska, K., et al., "Tracking phenotypically and functionally distinct T cell subsets via T cell repertoire diversity," *Mol Immunol.*, 45(3), Feb. 2008, pp. 607-618.
Lu, Y.-J., et al., "Protection against Pneumococcal Colonization and Fatal Pneumonia by a Trivalent Conjugate of a Fusion Protein with the Cell Wall Polysaccharide," *Infection and Immunity*, vol. 77, No. 5, May 2009, pp. 2076-2083.
Takamura, S., et al., "Specific niches for lung-resident memory CD8+ T cells at the site of tissue regeneration enable CD69-independent maintenance," *J. Exp. Med.*, vol. 213, No. 13, 2016, pp. 3057-3073.
Thomas, P., et al., "Cell-mediated Protection in Influenza Infection," *Emerging Infectious Diseases*, vol. 12, No. 1, Jan. 2006, pp. 48-54.
Williams, M., et al., "Effector and Memory CTL Differentiation," *Annu. Rev. Immunol.*, vol. 25, 2007, pp. 171-192.
Youn, H.-J., et al., "A single intranasal immunization with inactivated influenza virus and α-galactosylceramide induces long-term protective immunity without redirecting antigen to the central nervous system," *Vaccine*, vol. 25, 2007, pp. 5189-5198.
Zhou, F., et al., "Prolonged Protection against Intranasal Challenge with Influenza Virus following Systemic Immunization or Combinations of Mucosal and Systemic Immunizations with a Heat-Labile Toxin Mutant," *Clinical and Vaccine Immunology*, vol. 16, No. 4, Apr. 2009, pp. 471-478.

\* cited by examiner

INFLUENZA VACCINES

This application is a continuation of U.S. application Ser. No. 13/056,932, filed Mar. 8, 2011, which is a national stage application under 35 U.S.C. § 371 of PCT/AU2009/000983, filed Jul. 31, 2009, which claims priority to U.S. Provisional Application No. 61/085,802, filed Aug. 1, 2008, the contents of each of which are incorporated herein in its entirety.

TECHNICAL FIELD

The invention relates to compositions and methods for the prevention and treatment of infection by influenza virus. More specifically, the invention relates to vaccine compositions and methods for eliciting cross-reactive immunity to influenza viruses.

BACKGROUND

Influenza is a highly contagious disease caused by infection of the respiratory tract with influenza virus. It can cause potentially life-threatening complications especially in infants and the elderly.

Protection against re-infection with homologous virus is mediated primarily by neutralizing antibodies, but recovery from influenza virus infections requires cytotoxic CD8+ T (Tc) cell responses. Current vaccines against influenza virus are predominantly inactivated whole virus or subunit preparations, where the infectivity of the virus is inactivated by chemical treatment. These vaccines function almost exclusively by inducing neutralising antibodies targetting viral surface glycoproteins subject to frequent antigenic variation (e.g. HA and NA). The frequent antigenic variation exhibited by viral surface glycoproteins means that vaccines directed against them do not elicit a broadly cross-reactive immune response and are thus unable to protect against multiple influenza virus subtypes and strains. The protective value of antibody-based vaccines is thus restricted in that little or no protective immunity is provided against new subtypes/strains arising from frequent antigenic drift and/or shift of influenza viruses. Furthermore, the selective pressures imparted on viral surface glycoproteins by such vaccines serve to enhance antigenic variation rendering the vaccines ineffective.

The formulation of current influenza vaccines is based on "educated guesses" made by comparing currently circulating human influenza strains to known isolates. However, the prediction of influenza strain/s that may cause infection in a given flu season can not accommodate for the expected antigenic variability arising due to viral mutations. Moreover, while ongoing virus mutations and associated antigenic variation decreases the efficacy of vaccines, incorrect prediction renders the vaccine ineffective. The northern hemisphere flu vaccine formulation for season 2007-2008 (A/Solomon Islands/3/2006 (H1N1)-like virus; A/Wisconsin/67/2005 (H3N2)-like virus; and B/Malaysia/2506/2004-like virus) illustrates such a scenario. According to the Centers for Disease Control and Prevention in the U.S., Type A H3N2 Brisbane strain and Type B Florida strain were responsible for most of the illnesses in that flu season, however those strains were not incorporated into the vaccine which was consequently ineffective.

The beneficial affects of vaccination induced T cell-mediated immunity in ameliorating the severity of influenza has been largely ignored. The T cell response is central to successful recovery from primary infections with influenza and reduces disease severity by lowering the viral burden early after infection. T cell immunity is also long-lasting, and the antigenic determinants involved in eliciting T cell responses are generally derived from conserved proteins (e.g. viral nucleoprotein and matrix proteins) that are usually not subject to immune evasion by the virus. Hence, vaccines capable of eliciting T-cell mediated immunity are desirable and this need is not met by currently available inactivated influenza vaccine preparations.

Moreover, methods used in the manufacture of currently available influenza vaccines involve harsh treatments that compromise the integrity of viral antigens. For example, ultracentrifugation has a damaging effect on viral antigens but is commonly used to purify virus prior to attenuation. Furthermore, chemically inactivated influenza vaccine preparations require the use of unfrozen virus allowing physical and chemical agents to damage antigenic proteins. Therefore, viral inactivation methods effective on frozen virus preparations offer the advantage of limiting antigen degradation which enhances immunogenicity.

A need exists for influenza vaccines capable of inducing T lymphocyte responses. In particular, a need exists for influenza vaccines capable of inducing cross-protective immunity to influenza viruses, regardless of surface antigen variability frequently arising from antigenic shift and/or drift.

SUMMARY

In a first aspect, the invention provides a method for the treatment or prevention of an influenza virus infection in a subject, the method comprising administering to the subject a therapeutically effective amount of a gamma-irradiated influenza virus.

In a second aspect, the invention provides a method for the treatment or prevention of an influenza virus infection in a subject, the method comprising intranasally administering to the subject a therapeutically effective amount of a gamma-irradiated influenza virus.

In one embodiment of the first or second aspect, the influenza virus infection is influenza A subtype H5N1 infection.

In one embodiment of the first or second aspect, the influenza virus infection is influenza A subtype HPAI A(H5N1) infection.

In one embodiment of the first or second aspect, the influenza virus infection is influenza A subtype H1N1 09 Swine Flu infection.

In a third aspect, the invention provides a method for inducing cross-reactive immunity against multiple influenza virus subtypes in a subject, the method comprising administering to the subject a therapeutically effective amount of a gamma-irradiated influenza virus.

In a fourth aspect, the invention provides a method for inducing or enhancing cross-reactive immunity against multiple influenza virus subtypes in a subject, the method comprising intranasally administering to the subject a therapeutically effective amount of a gamma-irradiated influenza virus.

In one embodiment of the third or fourth aspect, the cross-reactive immunity comprises cross-reactive cellular immunity. The cross-reactive cellular immunity may comprise either or both of:
 (i) a cross-reactive helper T cell response
 (ii) a cross-reactive cytotoxic T cell response.

In one embodiment of the third or fourth aspect, the cross-reactive immunity may comprise cross-reactive humoral immunity.

In one embodiment of the third or fourth aspect, the multiple influenza virus subtypes comprise one or more of human, avian, swine, canine or equine influenza virus subtypes. The avian influenza virus subtypes may comprise influenza virus subtype H5N1.

In one embodiment of the third or fourth aspect, the multiple influenza virus subtypes comprise influenza A subtype HPAI A(H5N1).

In one embodiment of the third or fourth aspects, the multiple influenza virus subtypes comprise influenza A subtype H1N1 09 Swine Flu.

In a fifth aspect, the invention provides a method of inducing or enhancing a T cell immune response against influenza virus in a subject, the method comprising administering to the subject a therapeutically effective amount of a gamma-irradiated influenza virus. The T cell immune response may be induced or enhanced against influenza subtype H5N1. The T cell immune response may comprise either or both of:
 (i) a helper T cell immune response
 (ii) a cytotoxic T cell immune response.

In one embodiment of the fifth aspect, the T cell immune response is induced or enhanced against influenza A subtype HPAI A(H5N1).

In one embodiment of the fifth aspect, the T cell immune response is induced or enhanced against influenza A subtype H1N1 09 Swine Flu.

In one embodiment of the first, second, third, fourth or fifth aspect, the gamma-irradiated influenza virus is an influenza A virus. The influenza A virus may be selected from the group consisting of A/WSN [H1N1], A/PR8 [H1N1], A/JAP [H2N2] and A/PC [H3/N2].

In one embodiment of the first, second, third, fourth or fifth aspect, the gamma-irradiated influenza virus is a zoonotic influenza virus. The zoonotic influenza virus may be a zoonotic influenza A virus.

In one embodiment of the first, second, third, fourth or fifth aspect, the gamma-irradiated influenza virus is prepared in a freeze-dried form.

In one embodiment of the first, second, third, fourth or fifth aspect, the gamma-irradiated influenza virus is prepared from a virus stock purified by tangential/cross-flow filtration.

In one embodiment of the first, second, third, fourth or fifth aspect, the gamma-irradiated influenza virus is generated by gamma-irradiating a frozen viral preparation.

In one embodiment of the first, second, third, fourth or fifth aspect, the gamma-irradiated influenza virus is generated by exposing said virus to a total dose of between about $6.5 \times 10^4$ rad and about $2 \times 10^7$ rad of gamma rays.

In another embodiment of the first, second, third, fourth or fifth aspect, the gamma-irradiated influenza virus is generated by exposing said virus to a total dose of about $1 \times 10^6$ rad of gamma rays.

In an additional embodiment of the first, second, third, fourth or fifth aspect, the gamma-irradiated influenza virus is administered in multiple separate doses. One or more of the multiple separate doses may be administered as a booster for the purpose of revaccination.

In another embodiment of the first, second, third, fourth or fifth aspect, the therapeutically effective amount of a gamma-irradiated influenza virus is administered together with a pharmaceutically acceptable carrier, adjuvant or excipient.

In a sixth aspect, the invention provides a method of producing an influenza vaccine, the method comprising inactivating a preparation of influenza virus by gamma-irradiation.

In one embodiment of the sixth aspect, the preparation of influenza virus is purified by tangential/cross-flow filtration prior to a said inactivating by gamma-irradiation.

In one embodiment of the sixth aspect, the preparation of influenza virus is gamma-irradiated while frozen.

In one embodiment of the sixth aspect, the method comprises the additional step of freeze-drying said virus after said inactivating by gamma-irradiation.

In one embodiment of the sixth aspect, the vaccine is formulated for intranasal administration.

In one embodiment of the sixth aspect, the influenza vaccine induces cross-reactive immunity against multiple influenza virus subtypes.

In one embodiment of the sixth aspect, the multiple influenza virus subtypes comprise influenza A subtype HPAI A(H5N1).

In one embodiment of the sixth aspect, the multiple influenza virus subtypes comprise influenza A subtype H1N1 09 Swine Flu.

In one embodiment of the sixth aspect, the inactivating comprises exposing said virus to a total dose of between about $6.5 \times 10^4$ rad and about $2 \times 10^7$ rad of gamma rays.

In one embodiment of the sixth aspect, the inactivating comprises exposing said virus to a total dose of about $1 \times 10^6$ rad of gamma rays.

In another embodiment of the sixth aspect, the influenza vaccine induces cross-reactive immunity against multiple influenza virus subtypes. The influenza virus subtypes may comprise influenza virus subtype H5N1.

In another embodiment of the sixth aspect, the preparation of influenza virus comprises influenza A virus.

In a seventh aspect, the invention provides use of a gamma-irradiated influenza virus for the preparation of a medicament for treatment or prevention of influenza virus infection.

In one embodiment of the seventh aspect, the medicament is formulated for intranasal administration.

In another embodiment of the seventh aspect, the treatment or prevention of influenza virus infection is influenza virus subtype H5N1 infection.

In one embodiment of the seventh aspect, medicament induces cross-reactive immunity against multiple influenza virus subtypes. The multiple influenza virus subtypes comprise influenza A subtype HPAI A (H5N1). The multiple influenza virus subtypes comprise influenza virus subtype H1N1 09 Swine Flu.

In one embodiment of the seventh aspect, the medicament is a vaccine. The vaccine may induce cross-reactive immunity against multiple influenza virus subtypes.

In one embodiment of the seventh aspect, the gamma-irradiated influenza virus is influenza A virus.

In an eighth aspect, the invention provides gamma-irradiated influenza virus for use in the treatment or prevention of influenza infection.

In a ninth aspect, the invention provides a vaccine produced in accordance with the method of the sixth aspect.

BRIEF DESCRIPTION OF THE DRAWINGS

A preferred embodiment of the present invention will now be described, by way of an example only, with reference to the accompanying drawings wherein.

DEFINITIONS

Figure 1:
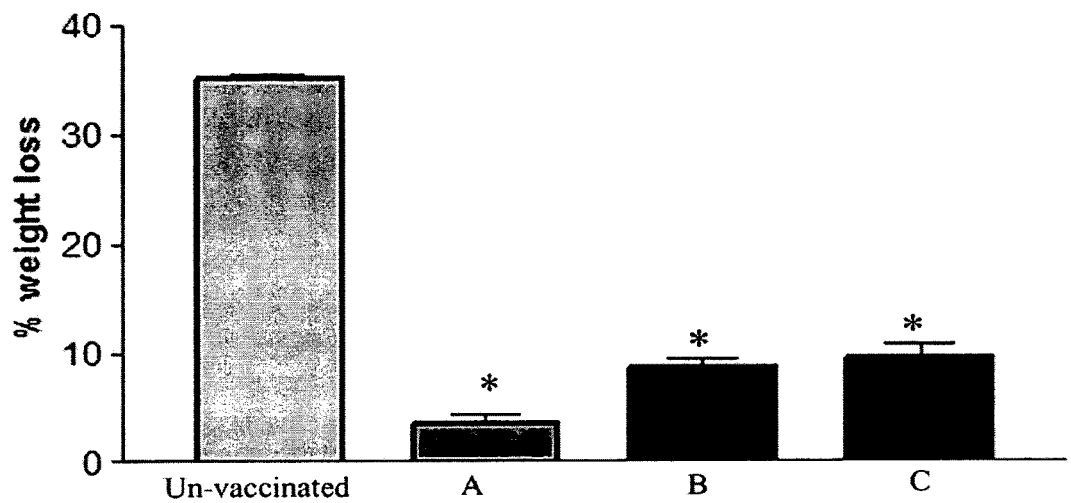
FIG. 1 is a bar graph showing weight loss of intravenously vaccinated animals following intranasal infection with A/JAP (50 HAU/mouse). Mice, from groups shown in Table 5, were weighed at day 6 post-infection.

As used in this application, the singular form "a", "an" and "the" include plural references unless the context clearly dictates otherwise. For example, the term "a plant cell" also includes a plurality of plant cells.

As used herein, the term "comprising" means "including." Variations of the word "comprising", such as "comprise" and "comprises", have correspondingly varied meanings. Thus, for example, a polynucleotide "comprising" a sequence encoding a protein may consist exclusively of that sequence or may include one or more additional sequences.

The terms "cross-reactive immunity" and "cross-protective immunity" are used interchangeably herein and have the same intended meaning.

As used herein, the terms "antibody" and "antibodies" include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-5 linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains.

Antibodies may be monoclonal, polyclonal, chimeric, multispecific, humanized, and human monoclonal and polyclonal antibodies which specifically bind the biological molecule.

Any description of prior art documents herein, or statements herein derived from or based on those documents, is not an admission that the documents or derived statements are part of the common general knowledge of the relevant art in Australia or elsewhere.

For the purposes of description all documents referred to herein are incorporated by reference unless otherwise stated.

DETAILED DESCRIPTION

Currently available influenza vaccines induce predominantly humoral responses (antibody responses derived from B cells). Those responses are directed primarily against the viral surface glycoproteins hemagglutinin (HA) and neuraminidase (NA), which are subject to frequent antigenic variation due to mutation. Accordingly, a notable disadvantage of current influenza vaccines is that little or no protection is provided against new influenza subtypes/strains arising from frequent antigenic drift and/or shift.

In contrast, T cell responses against influenza viruses are predominantly directed against internal viral proteins. These proteins are highly conserved among all influenza virus subtypes and are less susceptible to mutation. Hence, vaccines that induce T cell responses are more likely to confer cross-protective immunity to newly arising influenza subtypes/strains. T cell responses are also long-lasting and crucial for effective recovery from influenza infection. Accordingly, the ability to induce T cell immunity is a highly desirable property of an inactivated influenza virus vaccine. Despite this, currently available influenza vaccines are incapable of inducing T cell immunity and are thus substantially limited in their effectiveness.

The present invention provides a means of overcoming these disadvantages by providing influenza vaccines capable of inducing T cell immunity directed against conserved proteins of influenza virus. The gamma-irradiated (γ-irradiated) influenza vaccines of the present invention are also demonstrated to induce cross-reactive/cross-protective immunity to different influenza virus subtypes and strains.

Without being restricted by a particular mechanism, it is believed that the reduced impact of γ-irradiation on the antigenic structure and biological integrity of influenza viral surface proteins leaves their functional domains intact, thereby allowing efficient uptake and uncoating of viral particles by host immune cells. This in turn may provide sufficient viral antigen (matrix and nucleoprotein) into the cytoplasm of antigen presenting cells for the effective induction of T cell immunity. In addition, abortive replication/translation of fragmented genomic influenza virus RNA may occur allowing the priming of virus-specific T cell immunity, as defective ribosomal products (e.g. prematurely terminated and/or misfolded) are considered to be a dominant source of viral antigen for MHC class I antigen presentation. The reduced impact of γ-irradiation on the antigenic structure of viral particles is also believed to improve the magnitude and/or quality of humoral immunity in vaccine recipients compared to humoral immunity induced by currently used vaccine preparations.

In contrast to chemical treatments currently used in the production of inactivated influenza virus vaccines (e.g. formalin or β-propiolactone) which interact with and induce cross-linking of proteins, γ-irradiation is believed to inactivate viral infectivity by generating strand-breaks in genetic material. γ-irradiation has the further advantage, compared with chemical agents, of high penetration into and through biological materials. In addition γ-irradiation can be used to inactivate frozen preparations of influenza virus facilitating the preservation of viral antigens during vaccine manufacture.

Compositions and Vaccines

The present invention provides compositions and vaccines comprising γ-irradiated influenza virus. The compositions and vaccines may comprise any subtype or strain of γ-irradiated influenza virus. Mixtures of two or more strains of γ-irradiated influenza virus are also contemplated. Strains used in mixtures may be derived from the same or different influenza virus subtypes.

Compositions and vaccines of the invention may comprise a single γ-irradiated influenza strain, or a mixture of different γ-irradiated influenza strains. The influenza strain/s may be derived from any genera of the family Orthomyxoviridae. For example, the influenza strain may be derived from a subtype of the genus influenzavirus A (type A), influenzavirus B (type B), or influenzavirus C (type C).

Preferred subtypes of influenzavirus A include, but are not limited to H1N1 (e.g. H1N1 09 Swine Flu), H1N2, H1N7, H2N2, H3N1, H3N2, H3N8, H4N8, H5N1 (e.g. HPAI A(H5N1)), H5N2, H5N3, H5N8, H5N9, H6N5, H7N1, H7N2, H7N3, H7N4, H7N7, H8N4, H9N2, H10N7, H11N6, H12N5, H13N6, H14N5, and any other subtypes arising from re-assortment between influenza A viruses.

"H1N1 09 Swine Flu virus" as contemplated herein has also been referred to as "pandemic influenza A (H1N1)" by the World Health Organisation.

In certain embodiments, compositions and/or vaccines of the invention comprise γ-irradiated zoonotic influenza virus strain/s.

Influenza viruses for use in accordance with the invention can be generated using methods known in the art. For example, influenza viruses may be derived by serial passaging in embryonated eggs as described, for example, in Coico et al., (Eds) "Current Protocols in Microbiology", (2007), John Wiley and Sons, Inc. (see in particular Unit 15G.1 entitled "Influenza: Propagation, Quantification, and Storage"). A brief description of this technique is provided below.

Embryonated eggs may be obtained 9-12 days after fertilization and candled to locate the air sac. The egg may then be pierced under aseptic conditions, and the seed-virus inoculated into the air-space with a syringe. The procedure may be carried out manually or automatically by machines. The inoculated egg may then be incubated for approximately two to three days in a humidified atmosphere. At the end of this period, the egg can be maintained at approximately 4° C. if desired in order to terminate the embryo and aid clarification of the allantoic fluid. The top of the egg may then be removed, the membrane pierced, and the allantoic fluid collected. Again his can be achieved manually, or by automated machinery. The allantoic fluid may be clarified, for example, by centrifugation to remove cell debris and/or subjected to further purification prior to or following inactivation of the influenza virus by γ-irradiation. Purification of allantoic fluid may be achieved for example, by temperature-dependent adsorption to chicken red blood cells (CRBC), sucrose gradient, or dialysis.

Modifications of the above-mentioned process also suitable for the production of influenza virus are described, for example, in U.S. Pat. No. 7,270,990, PCT publication No. WO02/067983 and PCT publication No. WO 2005/113756.

Additionally or alternatively, influenza virus for use in the compositions and vaccines of the invention may be generated in cell culture (see, for example, Furminger, "Vaccine Production", in Nicholson et al. (eds.), Textbook of Influenza, Chapter 24, pp. 324-332 and Merten et al., 1996, "Production of influenza virus in cell cultures for vaccine preparation", in Cohen & Shafferman (eds.), Novel Strategies in Design and Production of Vaccines, pp. 141 151, U.S. Pat. No. 5,824,536 and U.S. Pat. No. 6,344,354).

Non-limiting examples of suitable cell lines that may be used as substrates for the growth of influenza virus include vero cells, Madin Darby canine kidney (MDCK) cells, PERC6 cells (see, for example, U.S. Pat. No. 7,192,759), chicken embryo cells (e.g. chicken embryo fibroblasts) and avian embryonic cell lines (see, for example, PCT publication No. WO 2006/108846). Variants of these cell lines may be used, including, but not limited to, those described in U.S. Pat. No. 6,825,036, U.S. Pat. No. 6,455,298 and PCT publication No. WO 2006/108846.

Propagation of influenza virus using cell lines will, in general, involve expanding the cells to the desired quantity in a chemically defined medium. Preferably, the medium is a serum free medium. Propagation of the virus can be assisted by the addition of proteases to the medium. Generally, the cells are infected with influenza virus and incubated for a period of time sufficient to generate the required numbers of virus (e.g. several days). Parameters such as multiplicity of infection, incubation time and temperature will generally need to be optimised for the specific cell line used and/or specific influenza strain/s being propagated. The optimisation of growth parameters including those referred to above can be readily determined by a person of ordinary skill in the field without undue experimentation. Following the incubation period, the virus may be harvested and purified if so desired.

Non-limiting examples of processes suitable for the production of influenza virus in cell culture include those described in U.S. Pat. No. 5,698,433, U.S. Pat. No. 5,753,489, U.S. Pat. No. 6,146,873, U.S. Pat. No. 6,455,298 and U.S. Pat. No. 6,951,752.

The yield of influenza virus production in cell culture may be enhanced, for example, by modifying cellular genes encoding the protein kinase PKR or (2'-5') oligoadenylate (2-5A) synthetase genes (see, for example, U.S. Pat. No. 6,673,591 and U.S. Pat. No. 6,686,190), or modifying the viral backbone with an alternative nonstructural protein 1 (NS1) gene (see, for example, PCT publication No. WO 2005/024039). Additionally or alternatively, cell lines utilised for the propagation of influenza virus may over-express sialyltransferase (see, for example, U.S. Pat. No. 7,132,271).

Influenza virus propagated using the methods above (or by any other means) may be purified and/or concentrated prior to γ-irradiation. Any suitable method known in the art may be used for this purpose. For example, influenza virus may be purified by temperature-dependent adsorption to chicken red blood cells using the method described by Laver (1969) "Purification of influenza virus", HKaS NP, (ed) New York and London: Academic Press. pp. 82-86. Alternatively, influenza virus may be purified by density gradient centrifugation (see, for example, Sokolov et al., (1971), "Purification and concentration of influenza virus", Archiv fair die gesarate Virusforschung, 35, 356-363).

Preferably, influenza virus is purified and/or concentrated prior to γ-irradiation using tangential/cross-flow filtration. For example, virus-containing fluid may be applied to a filtering device such as a membrane having an appropriate pore size (e.g. less than about 80 nm). The fluid is pumped tangentially along the surface of the membrane (i.e. across the surface) and pressure applied to force a portion of the fluid through the membrane to the filtrate side. The applied pressure will generally be of a degree that does not adversely affect virion structure and/or the integrity of viral antigens. Filtrate containing viral particles passes through the membrane, whereas particulates and macromolecules in the fluid that are too large to pass through the membrane pores are retained on the opposing side. In general, retentate (i.e. retained components) does not build up at the surface of the membrane and is instead swept along by the tangential flow. The retentate may be rediluted with appropriate media (e.g. PBS containing dextran and/or sucrose) and the filtration process repeated if required.

The use of tangential/cross-flow filtration to purify influenza virus used for γ-irradiation provides an advantage over purification techniques currently used for influenza vaccine preparation (e.g. ultracentrifugation) as the integrity of viral antigens is better preserved. This in turn enhances the immunogenicity of γ-irradiated viral preparations, and in particular their ability to elicit cross-reactive/cross-protective immunity against multiple influenza subtypes and strains.

Influenza virus for use in the compositions and vaccines of the invention is γ-irradiated. Any suitable source of γ-radiation may be used. Convenient gamma emitters include, but are not limited to $Ba^{137}$, $Co^{60}$, $Cs^{137}$, $Ir^{192}$, $U^{235}$, $Se^{75}$ and $Yb^{169}$.

γ-irradiation of influenza virus may be performed using commercially available devices, for example, a Gammacell irradiator manufactured by Atomic Energy of Canada Ltd., Canada (e.g. Gammacell 40 Irradiator, Gammacell 220 Irradiator, Gammacell 1000 irradiator, Gammacell 3000 irradiator), a gamma-irradiator manufactured by J. L. Shepherd and Associates (San Fernando, Calif., USA), or a Nordion Gamma Cell-1000 irradiator manufactured by Nordion Inc. (Kanata, Ontario, Canada). Other suitable devices are described, for example, in U.S. Pat. No. 3,557,370 and U.S. Pat. No. 3,567,938.

Preferably, the influenza virus is exposed to a dose of γ-irradiation sufficient to inactivate it. More preferably, the dose of γ-irradiation is sufficient to inactivate the virus without substantially disrupting the structure of viral antigens, and in particular without substantially disrupting the structure of viral surface antigens. The immunogenicity of antigenic determinant/s may therefore be retained by γ-irradiated virus.

Thus, in a preferred embodiment of the invention, influenza virus is treated with a dose of γ-irradiation capable of inactivating the virus while retaining its antigenic structure. Preferably, the dose of γ-irradiation is administered to the virus over a period of time and at a level sufficient to ensure that all viruses under treatment are exposed without adversely affecting the structural integrity of viral antigenic determinants.

For example, influenza virus may be exposed to a total dose of γ-irradiation in the range of about $1\times10^3$ rad and about $2\times10^9$ rad (or about 10 Gy to about $2\times10^4$ kGy). In certain embodiments of the invention, influenza virus is exposed to a total dose of γ-irradiation of between about $1\times10^3$ rad and about $2\times10^9$ rad, between about $1\times10^3$ rad and about $1\times10^9$ rad, between about $1\times10^3$ rad and about $1\times10^8$ rad, between about $1\times10^3$ rad and about $1\times10^7$ rad, between about $1\times10^3$ rad and about $1\times10^6$ rad, between about $1\times10^3$ rad and about $1\times10^5$ rad, between about $1\times10^3$ rad and about $1\times10^4$ rad, between about $1\times10^3$ rad and about $2\times10^9$ rad, between about $1\times10^4$ rad and about $2\times10^9$ rad, between about $1\times10^5$ rad and about $2\times10^9$ rad, between about $1\times10^6$ rad and about $2\times10^9$ rad, between about $1\times10^7$ rad and about $2\times10^9$ rad, between about $1\times10^8$ rad and about $2\times10^9$ rad or between about $1\times10^9$ rad and about $2\times10^9$ rad. In one embodiment of the invention, the influenza virus is exposed to a total dose of γ-rays of between about $6.5\times10^4$ rad and about $2\times10^7$ rad (about 0.65 KGy to about 200 kGy). In preferred embodiments of the invention, the influenza virus is exposed to a total γ-irradiation dose of about $1.26\times10^6$ rad (12.6 KGy), a total γ-irradiation dose of about $1\times10^6$ rad (about 10 kGy) γ-rays or a total γ-irradiation dose of about $1\times10^5$ rad (1 KGy).

The optimal dose of γ-irradiation may be influenced by factors such as the medium in which the virus is present, the amount of virus to be treated, the temperature of the virus present, and/or the subtype or strain of virus under treatment. Accordingly, the total dose of γ-irradiation, the exposure time and/or the level of γ-irradiation applied over the period of exposure may be optimised to enhance the effectiveness of the treatment.

The total dose of γ-irradiation may be administered to the virus cumulatively over a period of time. For example, γ-irradiation may be administered to the virus at a level lower than that of the total dose, over a time period sufficient to achieve the total dose of γ-irradiation required.

In one embodiment, influenza virus preparations are maintained in a frozen state while being exposed to γ-irradiation. This may facilitate the preservation of biological integrity and avoid unnecessary damage of viral antigens thereby enhancing the immunogenicity of γ-irradiated viral preparations, and in particular, their ability to elicit cross-reactive/cross-protective immunity against multiple influenza subtypes and strains. In general, a γ-irradiation dose of 10-20 kGy may be effective for treating frozen viral preparations.

As mentioned above, it is preferable that treatment with γ-irradiation is sufficient to inactivate the influenza virus without substantially disrupting the structure of viral antigens. Inactivation of the virus may be assessed using methods generally known in the art. For example, viral infectivity can be measured following γ-irradiation by inoculating embryonic eggs and/or cell lines as described above to determine whether the virus is capable of propagation.

The integrity of antigenic determinants can be assessed, for example, by assaying the virus for hemagglutinating activity following γ-irradiation. Methods of performing hemagglutination assays are known in the art, and are described for example, in Coico et al, (Eds) "*Current Protocols in Microbiology*", (2007), by John Wiley and Sons, Inc. (see in particular Unit 15G.1 entitled "*Influenza: Propagation, Quantification, and Storage*") and Sato et al., (1983), "*Separation and purification of the hemagglutinins from Bordetella pertussis*", Infect. Immun., 41, 313-320. Additionally or alternatively, a neuraminidase assay may be used to assess the integrity of viral antigenic determinants (see, for example, Khorlin et al., (1970), "*Synthetic inhibitors of Vibrio cholerae neuraminidase and neuraminidases of some influenza virus strains*", FEBS Lett., 8:17-19 and Van Deusen et al., (1983), "*Micro neuraminidase-inhibition assay for classification of influenza A virus neuraminidases*" Avian Dis., 27:745-50). Additionally, cytotoxic T cell responses against the internal proteins inducible by the gamma-irradiated preparations can be used to as indicator for protein integrity.

Suitable compositions and vaccines comprising γ-irradiated influenza virus may be prepared according to methods known to those of ordinary skill in the art, and accordingly may include a pharmaceutically acceptable carrier, diluent and/or adjuvant.

The carriers, diluents and adjuvants must be "acceptable" in terms of being compatible with the other ingredients of the composition, and not deleterious to the recipient thereof.

Although adjuvant/s may be combined with compositions and vaccines of the invention comprising γ-irradiated influenza virus, experimental data provided herein demonstrates that similar levels of immunogenicity may obtained using γ-ray inactivated influenza preparations in the absence of an adjuvant. Hence, it will be understood although adjuvants may be included in compositions and vaccines of the invention they are not generally required. Accordingly, reactogenicity problems arising from the use of adjuvants can be avoided.

Preferably, an adjuvant will enhance the immune response induced and/or enhanced by the γ-irradiated influenza virus, thereby improving protective efficacy. Preferably, the adjuvant will enable the induction of protective immunity utilising a lower dose of γ-irradiated influenza virus.

Any suitable adjuvant may be included in the compositions and vaccines of the invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223.

Oil in water emulsions may be utilised as adjuvants in the compositions and vaccines of the invention. Oil in water emulsions are well known in the art. In general, the oil in water composition will comprise a metabolizable oil, for example, a fish oil, a vegetable oil, or a synthetic oil. Examples of suitable oil in water emulsions include those described in European Patent No. 0399843, U.S. Pat. No. 7,029,678 and PCT publication No. WO 2007/006939. The oil in water emulsion may be utilised with other adjuvants and/or immunostimulants.

Non-limiting examples of other suitable adjuvants include immunostimulants such as granulocyte-macrophage colony-stimulating factor (GM-CSF), monophosphoryl lipid A (MPL), cholera toxin (CT) or its constituent subunit, heat labile enterotoxin (LT) or its constituent subunit, toll like receptor ligand adjuvants such as lipopolysaccharide (LPS) and derivatives thereof (e.g. monophosphoryl lipid A and 3-Deacylated monophosphoryl lipid A), muramyl dipeptide (MDP) and F protein of Respiratory Syncytial Virus (RSV).

Examples of pharmaceutically acceptable carriers or diluents include demineralised or distilled water; saline solution; vegetable based oils such as peanut oil, safflower oil, olive oil, cottonseed oil, maize oil, sesame oils, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Compositions and vaccines of the present invention can be administered by standard routes, including, but not limited to, parenteral (e.g., intravenous, intraspinal, subcutaneous or intramuscular), oral, mucosal (e.g. intranasal) or topical routes.

The compositions and vaccines of the present invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, subcutaneous, intramuscular or intravenous injection.

The intranasal administration of the compositions and vaccines can be formulated, for example, in liquid form as nose drops, spray, or suitable for inhalation, as powder, as cream, or as emulsion.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents. Another type of 'self adjuvant' is provided by the conjugation of immunogenic peptides to lipids such as the water soluble lipopeptides Pam3Cys or its dipalmitoyl derivative Pam2Cys. Such adjuvants have the advantage of accompanying the immunogenic peptide into the antigen presenting cell (such as dendritic cells) and thus producing enhanced antigen presentation and activation of the cell at the same time. These agents act at least partly through TOLL-like receptor 2. (Reference Brown L E and Jackson D C, Lipid based self adjuvanting vaccines. Current Drug Delivery, 23:83, 2005).

The composition and vaccines of the present invention may include a pharmaceutically acceptable excipient such as a suitable adjuvant. Suitable adjuvants are commercially available such as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

In one embodiment of the invention, the adjuvant composition may induce an immune response predominantly of the TH1 type. Suitable adjuvants for use in eliciting a predominantly TH1-type response include, for example, a combination of monophosphoryl lipid A, preferably 3-de-O-acylated monophosphoryl lipid A (3D-MPL) together with an aluminium salt. For example, the composition or vaccine may be formulated with adjuvant ASO4 containing aluminium hydroxide (alum) and 3-O-deacylated monophosphorylated lipid A (MPL) such as described in Thoelen, S., et al., "A prophylactic hepatitis B vaccine with a novel adjuvant system", *Vaccine* (2001) 19:2400-2403. Other known adjuvants which preferentially induce a TH1 type immune response include CpG containing oligonucleotides. The oligonucleotides are characterised in that the CpG dinucleotide is unmethylated. Such oligonucleotides are well known and are described in, for example PCT publication No. WO 1996/02555. Immunostimulatory DNA sequences are also described, for example, by Sato et al., 1996, *"Immunostimulatory DNA sequences necessary for effective intradermal gene immunization"*, Science, 273: 352-354. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in PCT publication No. WO 1994/00153, or a less reactogenic composition where the QS21 is quenched with cholesterol, as described in PCT publication No. WO 1996/33739. Other preferred formulations comprise an oil-in-water emulsion and tocopherol. An adjuvant formulation involving QS21, 3D-MPL and tocopherol in an oil-in-water emulsion is described in PCT publication No. WO 1995/17210. The adjuvant composition may include a formulation involving QS21, 3D-MPL and tocopherol in an oil in water emulsion such as described in PCT publication No. WO 1995/17210. In one embodiment the composition comprises the adjuvant Montanide ISA720 (M-ISA-720; Seppic, Fairfield, N.J.), an adjuvant based on a natural metabolizable oil.

Vaccines and compositions of the present invention may be prepared according to standard methods, for example as is generally described in Pharmaceutical Biotechnology, Vol. 61 *"Vaccine Design—the subunit and adjuvant approach"*, edited by Powell and Newman, Plenum Press, 1995, and *"New Trends and Developments in Vaccines"*, edited by Voller et al., University Park Press, Baltimore, Md., U.S.A. 1978.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The compositions and vaccines of the present invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions and vaccines of the present invention may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq.

Medicaments and Vaccines

Also contemplated by the present invention are methods for the production of vaccines for the prevention of influenza infection. The methods comprise inactivating a preparation of influenza virus by γ-irradiation. Influenza virus preparations for use in the vaccine production methods may be generated and γ-irradiated as described above in this section (i.e. "Compositions and Vaccines").

The influenza virus preparation may comprise influenza A virus. The influenza A virus preparation may comprise strain/s from one or more subtypes of influenza A that commonly infect humans. The influenza A strain/s may be currently circulating in human population/s.

Preferably, the influenza vaccines of the invention induce and/or enhance cross-reactive immunity against multiple influenza virus subtypes in a subject. Most preferably, the multiple influenza virus subtypes comprise influenza virus subtype H5N1 (e.g. HPAI A(H5N1)) and/or H1N1 (e.g. H1N1 09 Swine Flu). The vaccine may be formulated for intranasal administration.

In one embodiment, the influenza virus preparation comprises one or more strains of a zoonotic influenza A virus.

In another embodiment, the influenza vaccine is formulated for intranasal administration.

In one embodiment, the vaccine production method comprises inactivating a preparation of influenza virus by gamma-irradiation (see Section above entitled "Compositions and Vaccines").

In one embodiment, the vaccine production method comprises purifying influenza virus by tangential/cross-flow filtration prior inactivating by gamma-irradiation (see Section above entitled "Compositions and Vaccines")

In another embodiment, the vaccine production method comprises gamma-irradiating a frozen preparation of influenza virus (see Section above entitled "Compositions and Vaccines").

In another embodiment, the vaccine production method comprises the step of freeze-drying the virus after inactivating by gamma-irradiation (see Section below entitled "Routes of Administration").

In another embodiment, the vaccine production method comprises exposing a viral preparation to a total dose of between about $6.5 \times 10^4$ rad and about $2 \times 10^7$ rad of gamma rays.

In another embodiment, a vaccine produced in accordance with the production method described herein can be used in vaccination or for the purpose of re-vaccination.

In another embodiment, the vaccine production method comprises exposing a viral preparation to a total dose of about $1 \times 10^6$ rad of gamma rays.

In one embodiment of the invention, the vaccine may be used for revaccination. Typically, revaccination is made at least 6 months after the first vaccination/s, suitably 8 to 14 months after the first vaccination/s, suitably about 10 to 12 months after the first vaccination/s. The revaccination (or "booster") may be administered together with a pharmaceutically acceptable carrier, adjuvant or excipient.

In one aspect, the invention provides a vaccine produced in accordance with the vaccine production method decribed herein.

The invention also provides the use of a gamma-irradiated influenza virus for the preparation of a medicament for treatment and/or prevention of influenza virus infection. The gamma-irradiated influenza virus may be any influenza virus, including, but not limited to, influenza A virus. Preferably, the medicament induces cross-reactive immunity against multiple influenza virus subtypes. In one embodiment, the medicament is for the treatment and/or prevention of influenza virus subtype H5N1 (e.g. HPAI A(H5N1)) and/or H1N1 (e.g. H1N1 09 Swine Flu) infection. In another embodiment the medicament is a vaccine. In a preferred embodiment, the medicament is formulated for intranasal administration.

Also provided by the invention is gamma-irradiated influenza virus for use in the treatment or prevention of influenza infection.

Methods of Treatment

The present invention provides methods of treatment or prevention of influenza virus infection in a subject. The method comprises administering a therapeutically effective amount of a gamma-irradiated influenza virus to the subject.

The γ-irradiated influenza virus may be administered to the subject in the form of a composition or vaccine of the invention (see section above entitled "Compositions and vaccines"). In general, the γ-irradiated influenza virus will be immunogenic. Typically, the method comprises immunizing a subject against an influenza virus infection.

The "subject" is a mammal, such as any mammal of economic, social or research importance including bovine, equine, ovine, primates, and rodents. Typically the subject is a human. The subject may be infected with influenza virus, suspected of infection with influenza virus, previously infected with influenza virus, and/or at risk of infection with influenza virus. A subject at risk of infection with influenza virus may be, for example, a subject working with or caring for an individual infected with influenza virus.

The term "therapeutically effective amount" as used herein, includes within its meaning a non-toxic but sufficient amount of composition or vaccine for use in the invention to provide the desired therapeutic effect. The exact amount required will vary from subject to subject depending on factors such as the viral subtype/strain being treated, the age and general condition of the subject, the severity of the condition being treated, the particular agent being administered and the mode of administration, and so forth. Thus, it is not possible to specify an exact "effective amount". However, for any given case, an appropriate "effective amount" may be determined by one of ordinary skill in the art using only routine experimentation.

A therapeutically effective amount of γ-irradiated influenza virus (or composition comprising γ-irradiated influenza virus) in accordance with the methods of the invention may be administered to a subject in one dose or may be administered in more than one dose.

Generally, the term "therapeutically effective amount" means an amount of said γ-irradiated influenza virus (or composition comprising γ-irradiated influenza virus) which is capable of inducing and/or enhancing an immune response against one or more strains of influenza virus. Preferably, the immune response is induced and/or enhanced against strains from one or more different subtypes of influenza. Typically, a therapeutically effective amount when administered to a subject will induce an immune response in the subject sufficient to diminish the severity of infection upon subsequent exposure of said subject to influenza virus or to diminish one or more symptoms of an influenza virus infection when administered to an influenza virus-infected subject. It will be understood that reduction in any one or more symptoms typically seen in influenza infection is encompassed within the meaning, for example a decrease in the duration of infection, a decrease in the duration of one or more symptoms, such as fever, headache, cough, painful throat, body aches, muscle pain, nasal congestion, coughing, sneezing, reddened eyes, skin, mouth, throat and nose, diarrhea, vomiting and fatigue.

Accordingly, the invention provides methods for the treatment of such conditions where said condition is associated with influenza virus infection, by administration of a therapeutically effective amount of γ-irradiated influenza virus (or composition comprising γ-irradiated influenza virus). The γ-irradiated influenza virus may be any suitable subtype or strain of γ-irradiated influenza virus. The administration of mixtures of two or more strains of γ-irradiated influenza virus are also contemplated. The strains may be derived from different influenza virus subtypes.

The influenza strain/s may be derived from any genera of the family Orthomyxoviridae. For example, the influenza strain may be derived from a subtype of the genus influenzavirus A (type A), influenzavirus B (type B), or influenzavirus C (type C).

Preferred subtypes of influenzavirus A include, but are not limited to H1N1 (e.g. H1N1 09 Swine Flu), H1N2, H1N7, H2N2, H3N1, H3N2, H3N8, H4N8, H5N1 (e.g. HPAI A(H5N1)), H5N2, H5N3, H5N8, H5N9, H6N5, H7N1, H7N2, H7N3, H7N4, H7N7, H8N4, H9N2, H10N7, H11N6, H12N5, H13N6, H14N5, and any other subtypes arising from re-assortment between influenza A viruses.

In certain embodiments, γ-irradiated influenza virus strain/s utilised in the methods of the invention comprise γ-irradiated zoonotic influenza virus strain/s.

Influenza virus for use in accordance with the methods of the present invention may be generated using methods known in the art. For example, influenza virus may be generated by serial passaging in embryonated eggs and/or generated in cell culture, techniques which are described in the section above entitled "Compositions and Vaccines".

γ-irradiation of influenza virus for use in accordance with the methods of the present invention may be carried out by methods known in the art. Examples of suitable methods for the γ-irradiation of influenza virus are provided in the section above entitled "Compositions and Vaccines".

Preferably, the subject is a human, and the γ-irradiated influenza virus administered comprises influenza subtype/s known to infect humans. Alternatively, the γ-irradiated influenza virus administered may comprise influenza subtype/s not known to infect humans. The administration may be intranasal administration. The γ-irradiated influenza virus may be prepared in a freeze-dried form (see Section below entitled "Routes of Administration"). The γ-irradiated influenza virus administered to the subject may be prepared from a virus stock purified by tangential/cross-flow filtration as described in the Section above entitled "Compositions and Vaccines". Viral stock used to prepare the γ-irradiated influenza virus administered to the subject may be frozen during γ-irradiation (see Section above entitled "Compositions and Vaccines").

In accordance with the methods of the invention, administration of γ-irradiated influenza virus to a subject will, in general, induce and/or enhance the immune response against influenza virus in a subject. In one embodiment of the invention, an immune response may be induced in an immunologically unprimed patient previously unexposed to (or having failed to respond to) influenza virus.

In another embodiment of the invention, an immune response may be induced in an immunologically unprimed patient previously unexposed to (or having failed to respond to) the particular γ-irradiated influenza virus subtype/s from which the administered strain/s derive. Additionally or alternatively, an immune response may be induced in an immunologically unprimed patient previously unexposed to (or having failed to respond to) the particular γ-irradiated influenza virus strain/s administered.

In another embodiment of the invention, an immune response may be enhanced in a subject that has been previously exposed to and generated an immune response to the particular γ-irradiated influenza virus strain/s administered. Additionally or alternatively, an immune response may be enhanced in a subject that has been previously exposed to and generated an immune response to the particular γ-irradiated influenza virus subtype/s from which the administered strain/s derive.

Preferably, the immune response induced and/or enhanced in the subject is a cross-reactive immune response. Accordingly, in a preferred embodiment of the invention, the administration of a particular subtype of γ-irradiated influenza virus induces and/or enhances the immune response to other additional influenza virus subtype/s. In a preferred embodiment, the administration of one or more γ-irradiated preparations of strain/s derived from currently circulating human influenza A subtype/s induces and/or enhances the immune response against avian influenza subtype H5N1 (e.g. HPAI A(H5N1)) and/or H1N1 (e.g. H1N1 09 Swine Flu).

The methods of the invention may be used to induce and/or enhance T cell responses in a subject specific to multiple strains of influenza virus. Preferably, the strains are derived from multiple different subtypes of influenza virus. In general, induction and/or enhancement of the T cell immune response may involve enhancement of the activity of CD4+ T cells and/or CD8+ T cells. The T cells may be helper T cells (e.g. helper CD4+ T cells) or cytotoxic T cells (e.g. cytotoxic CD4+ T cells, cytotoxic CD8+ T cells).

The induction and/or enhancement of the T cell immune response in a subject can be detected using methods known in the art. For example, an increased number of influenza virus-specific T cells can be measured to provide indication that the T cell immune response is enhanced or induced. Methods and techniques for enumeration and characterization of virus-specific CD4+ T cells and CD8+ T cells are known in the art. Influenza-specific T cells may be detected by ELISpot assays, using methods generally described in, for example, Vogt et al., 2008, *"Transcutaneous anti-influenza vaccination promotes both CD4 and CD8 T cell immune responses in humans"*, J. Immunol., 180: 1482-1489. Additionally of alternatively, influenza virus-specific T cells can be detected by measuring the proportion CD4+ T cells and/or CD8+ T cells responsive to challenge with influenza virus and/or protein antigen/s derived therefrom. Typically, responsive T cells secrete one or more specific cytokines upon exposure to influenza viral antigens (e.g. IL-2, IFN-γ, TNFα and/or CD40L) which can be detected, for example, using intracellular cytokine staining assays (see, for example, Vogt et al., supra and Longhi et al., 2008, *"Interleukin-6 Is Crucial for Recall of Influenza-Specific Memory $CD4^+$ T Cells"*, PLoS Pathog., 4(2): e1000006). Examples of other suitable assays for the detection of influenza-specific T cells include tetramer-based assays (see, for example, Longhi et al., supra and Flynn et al., 1999, *"In vivo proliferation of naive and memory influenza-specific $CD8^+$ T cells"* PNAS, 96(15): 8597-8602).

Additionally or alternatively, the methods of the invention may induce and/or enhance the humoral immune response in a subject specific to multiple strains of influenza virus. Preferably, the strains are derived from multiple different subtypes of influenza virus. In general, induction and/or enhancement of the humoral immune response may involve enhancement of the activity of B cells. This may be reflected by an increased frequency of peripheral blood B lymphocytes capable of differentiation into antibody-secreting plasma cells upon encounter with influenza virus antigens. Accordingly, induction or enhancement of the humoral immune response may involve an increase in the quantity of influenza virus-specific antibodies (e.g. IgA and IgG) in the circulation. Methods for the detection of influenza-specific antibodies are known in the art (see, for example, Sasaki et al., 2007, *"Comparison of the influenza virus-specific effector and memory B-cell responses to immunization of children and adults with live attenuated or inactivated influenza virus vaccines"*, J Virol. 2007; 81:215-28 and Cox et al., 1994, *"An early humoral immune response in peripheral blood following parenteral inactivated influenza vaccination"*, Vaccine, 12:993-999).

In a preferred embodiment, administration of γ-irradiated influenza virus in accordance with the methods described herein induces and/or enhances the T cell immune response and/or the humoral immune response against influenza virus in a subject. In a particularly preferred embodiment, the administration of one or more strains of γ-irradiated human influenza A virus induces and/or enhances the T cell immune response and/or the humoral immune response against avian influenza H5N1 (e.g. HPAI A(H5N1)) and/or H1N1 (e.g. H1N1 09 Swine Flu), in a subject. The γ-irradiated human influenza A virus may be administered intranasally.

Cross-Reactive/Cross-Protective Immunity

Current influenza vaccines target highly variable viral surface glycoproteins subject to frequent antigenic variation due to mutation. Accordingly, their protective value is significantly restricted as little or no protection is provided against other influenza virus subtypes and/or newly arising subtypes.

The present invention overcomes these disadvantages by inducing and/or enhancing immune responses against internal influenza virus proteins. These proteins are highly conserved among all influenza virus subtypes and are less susceptible to mutation. Accordingly, the present invention provides a method for inducing and/or enhancing cross-reactive immunity against multiple influenza virus subtypes in a subject. The method comprises administering to the subject a therapeutically effective amount of a gamma-irradiated influenza virus. The cross-reactive immunity may arise from the induction and/or enhancement of cross-reactive T cell immunity. Additionally or alternatively, the cross-reactive immunity may arise from the induction and/or enhancement of cross-reactive humoral immunity in the subject.

Preferably, the subject is a human, and the γ-irradiated influenza viruses administered comprise influenza subtype/s known to infect humans. Alternatively, the γ-irradiated influenza viruses administered may comprise influenza subtype/s not known to infect humans.

In one embodiment, the γ-irradiated influenza viruses administered comprise zoonotic influenza virus strain/s.

The administration may be intranasal administration. Preferably, cross-protective immunity is induced and/or enhanced against conserved influenza virus antigens. Most preferably, cross-protective immunity is induced and/or enhanced against conserved influenza virus antigens that are not subject to antigenic shift and/or drift, or influenza virus antigens that are subject to a negligible degree of antigenic shift and/or drift. A negligible degree of antigenic shift and/or drift will, in general, be a degree of antigenic shift and/or drift that does not alter the ability of host immune cells to recognise and respond to the antigen.

In a preferred embodiment of the invention, cross-reactive immunity comprising immunity to influenza virus is induced or enhanced by intranasal administration of γ-irradiated influenza virus to a subject. The γ-irradiated influenza virus may be prepared in a freeze-dried form (see Section below entitled "Routes of Administration"). The γ-irradiated influenza virus administered to the subject may be prepared from a virus stock purified by tangential/cross-flow filtration as described in the Section above entitled "Compositions and Vaccines". Viral stock used to prepare the γ-irradiated influenza virus administered to the subject may be frozen during γ-irradiation (see Section above entitled "Compositions and Vaccines").

In a preferred embodiment of the invention, the cross-reactive immunity arises from the induction (and/or enhancement of activity) of cross-reactive CD8+ T cells specific for multiple influenza virus subtypes.

In general, a cross-reactive immune response will be directed towards one or more influenza virus antigens that are identical or substantially similar in one or more different influenza virus subtypes. A cross-reactive immune cell will thus recognise and respond to substantially similar or identical viral antigen/s shared by multiple virus subtypes.

Administration of γ-irradiated influenza virus to a subject in accordance with the methods described herein may thus generate cross-reactive immune cells. The cross-reactive immune cells will be capable of recognising and responding to strains of the influenza virus subtype/s administered to the subject. In addition, the cross-reactive immune cells will be capable of recognising and responding to strains of at least one other additional influenza virus subtype that was not administered to the subject.

Cross-reactive immunity induced and/or enhanced in a subject in accordance with the methods of the present invention may comprise cross-reactive cellular immunity. Cross-reactive cellular immunity may comprise, for example, cross-reactive helper T cell responses and/or cross-reactive cytotoxic T cell responses. Preferably, cross-reactive cellular immunity will involve cross-reactive cytotoxic CD8+ T cell responses. Without being bound by a particular mechanism, it is believed that cross-reactive T cell immunity induced and/or enhanced by the methods of the present invention may arise from efficient uptake of γ-irradiated influenza virus into antigen presenting cells due to the preserved integrity of functional domains of viral surface proteins (e.g. functional receptor and fusion domains) afforded by γ-irradiation. This in turn may allow more efficient uptake and uncoating of viral particles providing sufficient viral antigen (e.g. matrix and nucleoprotein) into the cytoplasm of antigen presenting cells and the effective presentation of viral antigens on major histocompatibility (MHC) proteins. Additionally or alternatively, abortive replication/translation of fragmented genomic influenza virus RNA may occur providing a dominant source of viral antigen (i.e. defective ribosomal products including prematurely terminated and/or misfolded gene products) for MHC presentation thereby priming virus-specific T cell immunity.

The induction and/or enhancement of the cross reactive cellular immunity can be detected using methods known in the art. For example, cross-reactive T cells (e.g. helper T cells and cytotoxic T cells) may be detected or quantified using general methods utilised for the detection virus-specific T cells including ELISpot assays, intracellular cytokine staining assays and tetramer-based assays (as described above).

Cross-reactive immunity induced and/or enhanced in a subject may comprise cross-reactive humoral immunity. Cross-reactive humoral immunity will generally involve cross-reactive B cell responses. This in turn may result in an increased quantity of cross-reactive influenza virus-specific antibodies (e.g. IgA and IgG) in the circulation of the subject. In general, a cross-reactive antibody will have the ability to react with and/or bind to an influenza virus antigen that did not stimulate its production. Cross-reactive B cells and antibodies derived therefrom may be detected using methods known in the art (e.g. by microneutralisation assay, flow cytometry or immunohistochemistry). Specific examples of suitable techniques for detecting cross-reactive influenza virus-specific antibodies are described in, for example, Rota et al., 1987 "*Comparison of the immune response to variant influenza type B hemagglutinins expressed in vaccinia virus*", Virology, 161:269-75, and Harmon et al., 1988, "*Antibody Response in Humans to Influenza Virus Type B Host-Cell-Derived Variants after Vaccination with Standard (Egg-Derived) Vaccine or Natural Infection*", J. Clin. Microbiol., 26:333-337.

In accordance with the methods of the invention, cross-reactive immunity induced and/or enhanced by administration of γ-irradiated strain/s from a given influenza virus subtype will provide cross-protection against strain/s of the administered subtype. Preferably, administration of γ-irradiated strain/s from a given influenza virus subtype will also provide cross-protection against strain/s from at least one additional influenza virus subtype.

Accordingly, the administration to a human subject of a therapeutically effective amount of a given γ-irradiated strain derived from one influenza A virus subtype known to infect humans will induce and/or enhance the immune response against strain/s from that subtype and strain/s from at least one other additional influenza virus subtype. The additional virus subtype may be an influenza A virus subtype, an influenza B virus subtype and/or an influenza C virus subtype. The additional influenza virus subtype may be, for example, a distinct influenza A subtype found in human populations (e.g. H1N1 (including H1N1 09 Swine Flu), H1N2, and H3N2). Additionally or alternatively, the additional influenza virus subtype/s may be commonly found in other species. For example, the additional influenza virus subtype may be commonly found in avian (e.g. A subtypes H5N1 (e.g. HPAI A(H5N1)), H7N2, H7N3, H7N7 and H9N2), swine (e.g. A subtypes H1N1, H1N2, H3N1, H3N2), canine (e.g. A subtype H3N8) or equine (e.g. A subtypes H3N8, H7N7) populations. The additional influenza virus subtype/s may also be recombinant viral strains derived from genetic recombination between subtypes. The subtypes may be derived from (i.e. infect) different species.

Antigenic shift and/or drift in influenza viruses are known causes of influenza pandemics. Cross-reactive immunity induced and/or enhanced by administration of γ-irradiated influenza virus in accordance with the methods described herein provides an effective means of preventing such pandemics by vaccination. Additionally or alternatively, individuals infected with influenza during pandemics may be treated with γ-irradiated influenza virus in accordance with the methods described herein.

In certain embodiments, the cross-reactive immunity induced or enhanced by administration of γ-irradiated influenza virus comprises immunity to zoonotic influenza virus strain/s.

In a preferred embodiment of the invention, the cross-reactive immunity induced or enhanced by administration of γ-irradiated influenza virus comprises immunity to (avian) influenza A virus subtype H5N1 (e.g. HPAI A(H5N1)). Current human influenza A virus binds predominantly to α2,6 linked sailic acid receptors expressed in the upper respiratory tract. Binding to α2,6 linked receptors is generally associated with low virulence highly transmissible influenza virus infection. In contrast, avian influenza H5N1 binds to α2,3 linked receptors expressed in the lower respiratory tract. Binding to α2,3 linked receptors is generally associated with low transmissibility but high virulence and lethal influenza virus infections. An avian H5N1 influenza pandemic is therefore expected to be associated with a mutation in the hemagglutinin (HA) protein of H5N1 allowing the virus to bind α2,6 linked receptors. Vaccines directed against currently prevalent H5N1 subtype proteins (i.e. α2,3 linked receptors) cannot induce immunity against H5N1 virus mutation/s that allow binding to α2,6 linked receptors. Accordingly, antibody-mediated protection by such vaccines is essentially ineffective against possible avian influenza pandemics.

Cross-recognition of avian H5N1 influenza virus (e.g. HPAI A(H5N1)) by T cell populations directed to human influenza A virus represents a means of overcoming the above-mentioned problem. In accordance with the methods of the present invention, the administration of γ-irradiated influenza virus to a subject induces and/or enhances cross-protective immunity in a subject against avian H5N1 influenza virus (e.g. HPAI A(H5N1)). The γ-irradiated influenza virus administered to the subject may or may not comprise γ-irradiated avian H5N1 influenza virus. Preferably, the subject is a human, and the γ-irradiated influenza virus administered comprises influenza A subtype/s known to infect humans. The administration may be intranasal administration. Preferably, cross-protective immunity is induced and/or enhanced against conserved avian H5N1 influenza virus antigens, including, but not limited to, HPAI A(H5N1) viral antigens. Most preferably, cross-protective immunity is induced and/or enhanced against conserved avian H5N1 influenza virus antigens that are not subject to antigenic shift and/or drift, or avian H5N1 influenza virus antigens that are subject to a negligible degree of antigenic shift and/or drift. A negligible degree of antigenic shift and/or drift will, in general, be a degree of antigenic shift and/or drift that does not alter the ability of host immune cells to recognise and respond to the antigen.

In a preferred embodiment of the invention, cross-reactive immunity comprising immunity to (avian) influenza virus subtype H5N1 (e.g. HPAI A(H5N1)) is induced or enhanced by intranasal administration of γ-irradiated influenza virus to a subject. The γ-irradiated influenza virus may be prepared in a freeze-dried form (see Section below entitled "Routes of Administration"). The γ-irradiated influenza virus administered may comprise influenza A virus subtype/s derived from human populations. Alternatively, the γ-irradiated influenza virus administered may comprise influenza subtype/s not known to infect humans. The γ-irradiated influenza virus administered to the subject may be prepared from a virus stock purified by tangential/cross-flow filtration as described in the Section above entitled "Compositions and Vaccines". Viral stock used to prepare the γ-irradiated influenza virus administered to the subject may be frozen during γ-irradiation (see Section above entitled "Compositions and Vaccines").

In another preferred embodiment of the invention, the cross-reactive immunity induced or enhanced by administration of γ-irradiated influenza virus comprises immunity to H1N1 09 Swine Flu virus (otherwise referred to by the World Health Organisation as "pandemic influenza A (H1N1)"). The γ-irradiated influenza virus administered to the subject may or may not comprise γ-irradiated H1N1 09 Swine Flu virus. The γ-irradiated influenza virus administered may comprise influenza A subtype/s known to infect humans. Alternatively, the γ-irradiated influenza virus administered may comprise influenza subtype/s not known to infect humans. The administration may be intranasal administration. Preferably, cross-protective immunity is induced and/or enhanced against conserved H1N1 09 Swine Flu virus antigens. Most preferably, cross-protective immunity is induced and/or enhanced against conserved H1N1 09 Swine Flu virus antigens that are not subject to antigenic shift and/or drift, or H1N1 09 Swine Flu virus antigens that are subject to a negligible degree of antigenic shift and/or drift. A negligible degree of antigenic shift and/or drift will, in general, be a degree of antigenic shift and/or drift that does not alter the ability of host immune cells to recognise and respond to the antigen.

In a preferred embodiment of the invention, cross-reactive immunity comprising immunity to H1N1 09 Swine Flu virus is induced or enhanced by intranasal administration of γ-irradiated influenza virus to a subject. The γ-irradiated influenza virus may be prepared in a freeze-dried form (see Section below entitled "Routes of Administration"). The γ-irradiated influenza virus administered may be an influenza A virus subtype derived from human populations. The γ-irradiated influenza virus administered to the subject may be prepared from a virus stock purified by tangential/cross-flow filtration as described in the Section above entitled "Compositions and Vaccines". Viral stock used to prepare the γ-irradiated influenza virus administered to the subject may be frozen during γ-irradiation (see Section above entitled "Compositions and Vaccines").

Dosages

The appropriate dosage of γ-irradiated influenza virus (or compositions/vaccines comprising γ-irradiated influenza virus) for use in accordance with the methods of the present invention may depend on a variety of factors. Such factors may include, but are in no way limited to, a subject's physical characteristics (e.g., age, weight, sex), whether the compound is being used as single agent or adjuvant therapy, the type of MHC restriction of the patient, the progression (i.e., pathological state) of the influenza infection, and other factors that may be recognized by one skilled in the art. In general, a γ-irradiated influenza virus preparation (or compositions/vaccines comprising a γ-irradiated influenza virus preparation) may be administered to a patient in an amount of from about 50 micrograms to about 5 mg; dosage in an amount of from about 50 micrograms to about 500 micrograms is especially preferred.

One skilled in the art would be able, by routine experimentation, to determine an effective, non-toxic amount of γ-irradiated influenza virus (or compositions/vaccines comprising γ-irradiated influenza virus) which would be required to treat applicable influenza virus infections.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would be for the duration of the disease state or condition. Further, it will be apparent to one of ordinary skill in the art that the optimal quantity and spacing of individual dosages will be determined by the nature and extent of the disease state or condition being treated, the form, route and site of administration, and the nature of the particular individual being treated. Also, such optimum conditions can be determined by conventional techniques.

It will also be apparent to one of ordinary skill in the art that the optimal course of treatment can be ascertained using conventional course of treatment determination tests.

Where two or more therapeutic entities are administered to a subject "in conjunction", they may be administered in a single composition at the same time, or in separate compositions at the same time or in separate compositions separated in time.

In certain embodiments, the methods of the invention involve the administration of γ-irradiated influenza virus (or compositions/vaccines comprising γ-irradiated influenza virus) in multiple separate doses. Accordingly, the methods for the prevention (i.e. vaccination) and treatment of influenza virus infection described herein encompass the administration of multiple separated doses to a subject, for example, over a defined period of time. Accordingly, the methods for the prevention (i.e. vaccination) and treatment of influenza virus infection disclosed herein include administering a priming dose of γ-irradiated influenza virus (or composition/vaccine comprising γ-irradiated influenza virus) of the present invention. The priming dose may be followed by a booster dose. The booster may be for the purpose of revaccination. In various embodiments, the composition or vaccine is administered at least once, twice, three times or more.

The γ-irradiated influenza virus (or compositions/vaccines comprising γ-irradiated influenza virus) of the present invention may be administered as a single agent therapy or in addition to an established therapy, such as inoculation with live, attenuated, or killed virus, or any other therapy known in the art to treat influenza virus. For example, they may be administered in conjunction with a subunit vaccine, a split influenza virus or split influenza virus antigenic preparation, an inactivated whole virus or a live attenuated influenza preparation.

Routes of Administration

The present invention contemplates administration of a therapeutically effective amount of γ-irradiated influenza virus (or a composition/vaccine comprising γ-irradiated influenza virus) to a subject. The γ-irradiated influenza virus (or composition/vaccine) may be administered together with a pharmaceutically acceptable carrier, adjuvant or excipient.

Administration may be performed by any suitable route, including, but not limited to, the parenteral (e.g. intravenous, intradermal, subcutaneous or intramuscular), mucosal (e.g. oral or intranasal) or topical route (see section above entitled "Compositions and vaccines").

Accordingly, γ-irradiated influenza virus (or composition/vaccine comprising the same) may be administered in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

In a preferred embodiment, γ-irradiated influenza virus (or compositions/vaccines comprising γ-irradiated influenza virus) is administered to a subject by the intranasal route. Intranasal administration of γ-irradiated influenza virus (or compositions/vaccines comprising the same) to a subject provides advantages over other routes of administration. For example, intranasal administration induces secretory IgA production at mucosal epithelium eliciting cross protection more effectively than serum IgG. Without being bound to a particular mechanism, inactivation of influenza virus by γ-irradiation is believed to inactivate the virus by way of causing strand breaks in the viral genome, without affecting the antigenic structure of the viral particles. Thus, the combination of γ-irradiation of influenza virus followed with intranasal administration is thought to offers several advantages, including, but not limited to: 1) facilitating the binding of inactivated virus to tissue specific receptors, 2) allowing the induction of tissue specific immune responses, 3) reducing the systemic exposure to whole virus antigen, and 4) limiting the side effects associated with whole virus vaccines.

In one embodiment, γ-irradiated influenza virus for intranasal administration is provided in a freeze-dried powder form capable of re-constitution immediately prior to use. Powder vaccine formulations of vaccines and compositions of the present invention provide a means of overcoming refrigerated storage and distribution requirements associated with liquid-based vaccine stability and delivery. Dry powder formulations offer the advantage of being more stable and also do not support microbial growth.

As demonstrated herein, freeze-dried formulations of γ-ray inactivated influenza virus induce levels of heterosubtypic immunity similar to that of non freeze-dried formulations. γ-irradiated influenza virus may be freeze-dried using any suitable technique known in the art. For example, liquid preparations of γ-ray inactivated influenza virus may be frozen in a dry ice-isopropanol slurry and lyophilized in a freeze Dryer (e.g. Virtis Model 10-324 Bench, Gardiner, N.Y.) for a suitable time period (e.g. 24 hours).

In one embodiment, a dry powder nasal vaccine formulation of γ-irradiated influenza virus is produced by generating spray-freeze-drying (SFD) particles (see, for example, Costantino et al., (2002), "Protein spray freeze drying. 2. Effect of formulation variables on particle size and stability", J Pharm Sci., 91:388-395; Costantino, et al., (2000), "Protein spray-freeze drying. Effect of atomization conditions on particle size and stability", Pharm Res., 17:1374-1383; Maa et al., (1999), "Protein inhalation powders: spray drying vs spray freeze drying", Pharm Res, 16:249-254; Carrasquillo et al., (2001); "Non-aqueous encapsulation of excipient-stabilized spray-freeze dried BSA into poly(lactide-co-glycolide) microspheres results in release of native protein", J Control Release, 76:199-208; Carrasquillo et al., (2001), "Reduction of structural perturbations in bovine serum albumin by non-aqueous microencapsulation", J Pharm Pharmacol., 53:115-120; and U.S. Pat. No. 6,569,458). For example, aqueous solutions containing γ-irradiated influenza virus and 10% solids (e.g. trehalose) may be passed through a sprayer with atomizing nitrogen gas and droplets collected in trays containing liquid nitrogen then lyophilized in a Manifold Freeze-Dryer. The freeze-dried formulation may be re-constituted immediately prior to use.

Intranasal administrations for use in accordance with the methods of the invention can be formulated, for example, in liquid form as nose drops, spray, or suitable for inhalation, as powder, as cream, or as emulsion.

Typically, the γ-irradiated influenza virus (or compositions/vaccines comprising the same) is administered to the nasopharyngeal area for absorption by nasal mucosa, preferably without being inhaled into the lungs. Suitable devices for intranasal administration in accordance with the methods of the invention include spray devices. Suitable commercially available spray devices may be used. Multiple-dose delivery devices containing sub-doses of γ-irradiated influenza virus (or compositions/vaccines comprising the same) may be utilised.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

The invention will now be described with reference to specific examples, which should not be construed as in any way limiting.

Example 1: Intravenous Vaccination of BALB/c Mice with Gamma-Irradiated Influenza a Virus (i) Materials and Methods Animals BALB/c mice of the same sex and within a similar age group (8-12 weeks old) were used in each experiment.

Viruses and Immunization

Influenza virus strains A/WSN (H1N1), A/JAP (H2N2) and A/PC (H3N2) were grown and titrated as described by Yap et al., 1977, *"Cytotoxic T cells specific for influenza virus-infected target cells"*, Immunology, 32: 151. Virus titres are expressed as haemagglutinating units (HAU). A/JAP influenza virus was inactivated either by exposure of crude allantoic fluid to $1.26 \times 10^6$ rad (12.6 KGy) from a $Co^{60}$ source (60 hours at 350 rad/min) or by exposure as dialysed, infectious allantoic fluid to UV radiation (320 μW/cm$^2$) for 10 min. Exposure to γ or UV radiation for these periods destroyed infectivity completely as tested in embryonated eggs. Animals were immunized by a single injection of $10^3$ HAU intravenously.

Target Cells

P815 thioglycollate-induced peritoneal macrophages (TGM), concanavalin-A (con-A) and lipopolysacharide (LPS) induced lymphoblasts were obtained, prepared and infected as described in Yap et al., 1977, *"Cytotoxic T cells specific for influenza virus-infected target cells"*, Immunology, 32: 151, and Parish and Müllbacher, 1983, *"Automated colorimetric assay for T cell cytotoxicity"*, J. Immunol Meth., 58: 225-237.

Generation of Effector Cells

Memory cultures for the generation of secondary in vitro influenza-immune Tc cells were generated using methods described in Müllbacher, 1984, *"Hyperthermia and the generation and activity of murine influenza-immune cytotoxic T cells in vitro"*, J. Virol., 52, 928-931. Briefly, $8 \times 10^7$ spleen cells from mice immunized with influenza virus 3 months previously were co-cultured with $1 \times 10^7$ virus-infected stimulator cells for 5 days in vitro. The stimulator cells were infected with infectious or inactivated virus at a multiplicity of infection of approximately $10^3$ HAU per $10^6$ cells.

Cytotoxicity Assay

The methods used for tumour cells and macrophage targets are described in detail in Yap et al., 1977, *"Cytotoxic T cells specific for influenza virus-infected target cells"*, Immunology, 32: 151, Parish and Müllbacher, 1983, *"Automated colorimetric assay for T cell cytotoxicity"*, J. Immunol Meth., 58: 225-237, and Müllbacher, 1984, *"Hyperthermia and the generation and activity of murine influenza-immune cytotoxic T cells in vitro"*, J. Virol., 52, 928-931. The duration of the assays was 6 hours. The percent specified lysis was calculated using the formula:

$$\text{Specific lysis (\%)} = \frac{\text{experimental release} - \text{medium release}}{\text{maximum release} - \text{medium release}} \times 100$$

(ii) Results

Priming of BALB/c Mice with Infectious or Inactivated Influenza Virus for Memory Tc Cells BALB/c mice were injected with $10^3$ HAU of either infectious, γ-irradiated or UV inactivated A/JAP virus. Three months later, spleens were removed and the cells boosted in vitro with infectious A/JAP-infected stimulator spleen cells and the Tc cell response measured 5 days later at three effector:target cell ratios. Table 1 shows representative data of percent specific lysis of infected P815 target cells. Clearly, infectious virus primed for a Tc cell response more effectively than γ-irradiated or UV-irradiated virus, but the γ-irradiated virus gave substantial lysis using all three infected target cells (A/WSN, A/JAP and A/PC) compared with a much weaker response by UV-irradiated virus. From precursor frequency analysis under limiting dilution conditions, animals primed with infectious virus gave approximately three-fold higher estimates of Tc cell precursor frequency in spleens than animals primed with γ-irradiated virus. This is in agreement with the values of lysis obtained in bulk cultures (Table 1).

TABLE 1

Secondary in vitro stimulation with infectious A/JAP virus of spleen cells from mice previously immunized with infectious, γ-irradiated or UV irradiated A/JAP virus.

| Primary immunization | Effector cell:target cell ratio | % Specific lysis of P815 cells* infected with: | | |
|---|---|---|---|---|
| | | A/WSN (H1N1) | A/JAP (H2N2) | A/PC (H3N2) |
| Infectious | 10 | 78 | 70 | 66 |
| | 3 | 86 | 67 | 76 |
| | 1 | 43 | 52 | 44 |
| γ-irradiated | 10 | 36 | 25 | 22 |
| | 3 | 35 | 27 | 20 |
| | 1 | 11 | 8 | 6 |
| UV-irradiated | 10 | 14 | 28 | 0 |
| | 3 | 0 | 13 | 0 |
| | 1 | 2 | 7 | 0 |

*Values for percent specific lysis given were obtained by subtracting the values of lysis by effector cells on uninfected P815 cells. The standard errors of the means of triplicate samples were always less than 8% and usually less than 4%. Spontaneous $^{51}$Cr release ranged from 16 to 19%.

Ability of Inactivated Virus to Boost Memory Influenza-Immune Tc Cells

Spleen cells of mice primed with infectious A/JAP virus ($10^3$ HAU) 3 months previously were boosted in vitro with A/JAP treated stimulator cells, using either infectious virus, γ-irradiated or UV-inactivated virus and Tc cell activity assays were carried out. The results shown in Table 2 demonstrate that all three viruses were able to restimulate cross-reactive Tc memory cells, but that γ-irradiated virus was superior to UV-irradiated virus. Cells boosted with UV-inactivated virus gave significant lysis only on target cells infected with the homologous virus.

TABLE 2

Secondary in vitro stimulation with infectious or inactivated A/JAP virus of spleen cells from mice previously immunized with infectious A/JAP virus.

| Primary immunization | Effector cell:target cell ratio | % Specific lysis of P815 cells* infected with: | | |
|---|---|---|---|---|
| | | A/WSN (H1N1) | A/JAP (H2N2) | A/PC (H3N2) |
| Infectious | 30 | 71 | 62 | 65 |
| | 10 | 80 | 82 | 84 |
| | 3 | 82 | 87 | 82 |
| | 1 | 38 | 59 | 31 |
| γ-irradiated | 30 | 47 | 62 | 41 |
| | 10 | 30 | 66 | 31 |
| | 3 | 16 | 33 | 24 |
| | 1 | 4 | 12 | 4 |
| UV-irradiated | 30 | 18 | 51 | 18 |
| | 10 | 15 | 28 | 19 |
| | 3 | 6 | 12 | 15 |
| | 1 | 2 | 7 | 0 |

*Values for percent specific lysis given were obtained by subtracting the values of lysis by effector cells on uninfected P815 cells. The standard errors of the means of triplicate samples were always less than 8% and usually less than 4%. Spontaneous $^{51}$Cr release ranged from 8 to 10%.

Sensitization of Target Cells with Infectious and Inactivated A/JAP Virus

To determine if inactivated influenza virus was able to sensitize target cells, P815 tumour cells, TGM, and LPS and con-A lymphoblasts were treated with either infectious, γ-irradiated or UV-inactivated virus at $10^3$ HAU per $10^6$ cells ($2 \times 10^6$ cells/ml) for 2 hours. These targets were then tested for specific lysis by secondary in vitro influenza immune Tc cells (Table 3). Only infectious virus was able to sensitize targets (especially P815 and TGM) to give significant lysis above uninfected control targets.

TABLE 3

Sensitization of target cells by infectious and inactivated A/JAP virus as tested by secondary influenza-immune Tc cells.

| Target | K:T | Specific $^{51}$Cr release (%)* | | |
|---|---|---|---|---|
| | | Infectious | γ | UV |
| P815 | 30 | 73 | 4 | 1 |
| | 10 | 72 | 4 | 2 |
| | 3 | 53 | 2 | 1 |
| TGM | 30 | 22 | 1 | 0 |
| | 10 | 16 | 1 | 0 |
| | 3 | 11 | 3 | 2 |
| LPS-blasts | 30 | 10 | 6 | 7 |
| | 10 | 11 | 9 | 0 |
| | 3 | 3 | 9 | 3 |
| Con-A blasts | 30 | 10 | 0 | 0 |
| | 10 | 10 | 0 | 0 |
| | 3 | 6 | 0 | 0 |

*Values for percent specific lysis given were obtained by subtracting the values of lysis by effector cells on uninfected P815 cells. The standard errors of the means of triplicate samples were always less than 8% and usually less than 4%. Spontaneous $^{51}$Cr release range: 10-12% for P815, 13-17% for TGM, 37-40% for LPS and 22-25% for con-A blasts.

Protection from Lethal Influenza Virus Infection with Inactivated Virus

To investigate whether mice immunized with such inactivated virus preparations would be protected against lethal influenza virus infections, mice were primed with infectious, γ-irradiated or UV-irradiated A/JAP virus 4-5 weeks prior to a challenge with a lethal dose of live influenza virus of the same or different subtypes. The results from one of two experiments are shown in Table 4. Mice primed with any of the three viruses survived a challenge by the homologous A/JAP and heterologous A/WSN virus, though mice primed with UV-irradiated virus and challenged with A/WSN sickened and one died. The major difference observed was with A/PC virus. Mice primed with UV-irradiated virus were as susceptible as unprimed animals, whereas mice primed with γ-irradiated virus survived the challenge at least as well as mice primed with infectious virus. It is unlikely that antibody was responsible for the observed cross-protection, as transfer of immune serum from animals primed with either infectious or γ-inactivated virus significantly reduced virus titres in the lungs of animals infected with the homologous A/JAP virus but not in A/WSN-infected animals.

TABLE 4

The effect of pre-immunization of mice with infectious, g-irradiated or UV-irradiated A/JAP on survival following a subsequent challenge with a lethal dose of infectious A/WSN (H1N1), A/JAP (H2N2) or A/PC (H3N2).

| Pre-immunization | Number of mice surviving challenge with: | | |
|---|---|---|---|
| (A/JAP) | A/WSN | A/JAP | A/PC |
| Nil | 1 | 0 | 1 |
| Infectious | 8 | ND* | 4 |
| γ-irradiated | 8 | 8 | 6 |
| UV-irradiated | 7 | ND* | 0 |

*Previous experiments had shown that primed mice would always withstand a challenge by the homologous virus. BALB/c mice were injected intravenously (i.v.) with $10^3$ HAU infectious, UV-irradiated or g-irradiated A/JAP virus or with nothing. Eight weeks later, groups of mice (eight mice per group) were inoculated intranasally with a lethal dose of A/WSN ($10^4$ EID$_{50}$), A/JAP ($3 \times 10^5$ EID$_{50}$) or A/PC ($1.5 \times 10^8$ EID$_{50}$). Death of mice was recorded for 20 days with the results given above.

These results demonstrate that γ-inactivated virus protects animals against lethal infection by heterologous A strain viruses at least as well as infectious virus. UV-inactivated virus on the other hand did not confer this protection to the more distantly related virus A/PC (H3N2). The finding that γ-irradiation is more effective than UV-irradiation in retaining the ability to prime for cross-reactive Tc cells upon destroying viral infectivity suggests that γ-irradiation is less damaging to the antigenic structure of at least some internal proteins than is UV irradiation. Surprisingly, there is little previously published work on the affect of γ-irradiation on viruses or proteins. In contrast to infectious virus, neither the γ-irradiated or UV-irradiated virus was able to sensitize target cells (activated macrophages, lymphoblasts or P815 cells) facilitating lysis by virus-specific Tc cells. However, it is possible that the cells which are mainly involved in antigen presentation of irradiated virus after intravenous injection may have characteristics different from those of activated macrophages or lymphocytes.

Example 2: Intravenous Vaccination with the γ-Irradiated Influenza A Strains A/WSN [H1N1], A/PR8 [H1N1], A/JAP [H2N2] and A/PC [H3/N2]

(i) Materials and Methods

Animals and Viruses

Stocks of influenza A virus (strains A/WSN, A/Pr8 [H1N1]; A/JAP [H2N2]; A/PC [H3N2]) were prepared in 10-day-embryonated eggs. Virus stocks were prepared from allantoic fluid and stored in aliquots at −70° C. Initially, BALB/c and C57Bl/6 mice were infected intranasally, and severity of flu infection was evaluated in terms of mortality, weight loss, lung histology and lung infiltration.

γ-Irradiation of Influenza Strains

γ-ray dose response studies of frozen and room temperature-kept viral stocks were undertaken at ANSTO/Lucas Heights/NSW to define the conditions that give sterile virus preparations with optimal immunogenicity. A radiation dose of $5 \times 10^5$ rad (5 KGy) was sufficient to induce sterility determined by hemagglutination (HA) assay following amplification of residual infectious virus in embryonated eggs. To safeguard for absolute virion inactivation, a dose of $1 \times 10^6$ rad (10 KGy) of γ-ray was chosen for the γ-flu (γ-irradiated influenza virus) preparations, which were used to vaccinate mice prior to their challenge with infectious influenza. Virus stocks were kept on dry ice through out the process of irradiation.

Intravenous Vaccination and Intranasal Challenge

Groups of 8 BALB/c mice were intravenously vaccinated twice, 4 weeks apart, with γ-flu prior to lethal intranasal challenge with A/JAP. γ-A/WSN (6×10³ haemagglutinating units (HAU)/mouse), γ-A/PC (6×10³ HAU/mouse), and γ-A/JAP (3×10³ HAU/mouse) were injected intravenously. Four weeks following the $2^{nd}$ dose of γ-flu, mice were challenged with A/JAP (50 HAU/mouse) and then monitored for 20 days.

Immunohistochemistry

Lungs were fixed in 10% neutral buffered formalin for one week and embedded in paraffin. For examination of tissue morphology, 4 micron sections were stained with hematoxylin and eosin (H&E).

Lymphocyte Isolation from the Lung and FACS Analysis

To evaluate the effect of vaccination with γ-flu on tissue infiltration of CD8+ T cells, lungs from mock and vaccinated mice were harvested into ice-cold MEM containing 5% FCS on days 6 post challenge with influenza virus. The samples were digested with 2 mg/mL collagenase type 1 (Gibco-Life Technologies) in MEM/5% FCS for 30 min at 37° C. with shaking and homogenised by gently pressing through a 100 µm mesh tissue sieve. Homogenates were then centrifuged at 400×g for 10 min, and the pellets were resuspended in 2 mL 90% Percoll (Sigma-Aldrich) in MEM/5% FCS. The suspension was transferred to a 15 mL tube and overlayed gently with 60, 40, and 10% Percoll in MEM. The gradients were centrifuged at 800×g for 45 min. The lymphocytes were collected from the 40-60% interface and washed twice with MEM/5% FCS. Expression of cell surface markers on freshly isolated lymphocytes from lungs of A/WSN-infected (both mock and vaccinated) mice was determined by staining with Ab specific for CD8 (PharMingen). Cells from a single mouse were suspended in 100 µL ice-cold MEM/5% FCS and incubated with Fc Block (PharMingen) for 15 min at 4° C. Cells were washed and incubated with the relevant Ab at 4° C. for 30 min in the dark and then washed twice, fixed with 2% w/v paraformaldehyde, and stored in the dark at 4° C. until analysis using a FACScan (Becton Dickinson).

Cross-Reactive CTL Responses Induced by γ-Flu

To test whether γ-flu induces cross-reactive Tc cell responses, A/WSN and A/PC and their corresponding γ-flu preparations were used to intravenously infect or vaccinate mice. 10-week-old BALB/c mice were either infected or vaccinated with A/WSN, γ-A/WSN, A/PC, and γ-A/Pc. Five-days later, splenocytes from infected, vaccinated, and mock-immunized animals were tested for their killing activity on mock, A/WSN-infected, A/PC-infected, and target cells modified with the appropriate $K^d$ restricted nucleoprotein derived peptide (NPP-labelled P815 targets). CTL response were measured using a $Cr^{51}$ release assay as described in Müllbacher et al., 1993, *"Spontaneous mutation at position 114 in H-2Kd affects cytotoxic T cell responses to influenza virus infection"* Eur. J. Immunol. 29, 1228-1234.

Statistics

All statistical analyses were conducted using GraphPad InStat software. One-Way-ANOVA test was used to compare the MEAN, and SEM for significant differences among vaccinated and un-vaccinated groups in terms of weight loss.

(ii) Results

Intravenous γ-Flu Vaccination Protects Against Lethal Challenge with Influenza A/JAP The capacity of γ-flu preparations to induce protective immunity was tested by challenging γ-flu primed mice with homologous and heterologous influenza viruses. Respiratory infection with influenza A/JAP (H2N2) in mice is associated with lethality, and $LD_{50}$ is 50 HAU/mouse intranasally (i.n.) in 10-week-old females BALB/c mice (Table 5).

TABLE 5

The protective effect of γ-flu preparations against homologous or heterologous influenza A infection.

| Group* | $1^{st}$ γ-flu (i.v.) | $2^{nd}$ γ-flu (i.v.) | Challenge (i.n.) | Survival |
|---|---|---|---|---|
| Un-vaccinated | — | — | A/JAP | 4/8 |
| A | γ-A/JAP | γ-A/JAP | A/JAP | 8/8 |
| B | γ-A/WSN | γ-A/PC | A/JAP | 6/8 |
| C | γ-A/PC | γ-A/WSN | A/JAP | 8/8 |

*Groups of 8 BALB/c mice were vaccinated twice, 4 weeks apart, with γ-flu prior to lethal challenge with A/JAP. γ-A/WSN (6 × 10³ HAU/mouse), γ-A/PC(6 × 10³ HAU/mouse), and γ-A/JAP (3 × 10³ HAU/mouse) were injected i.v. 4 weeks following the $2^{nd}$ dose of γ-flu, mice were challenge i.n with A/JAP (50 HAU/mouse) and mice were monitored for 20 days.

Figure 2:
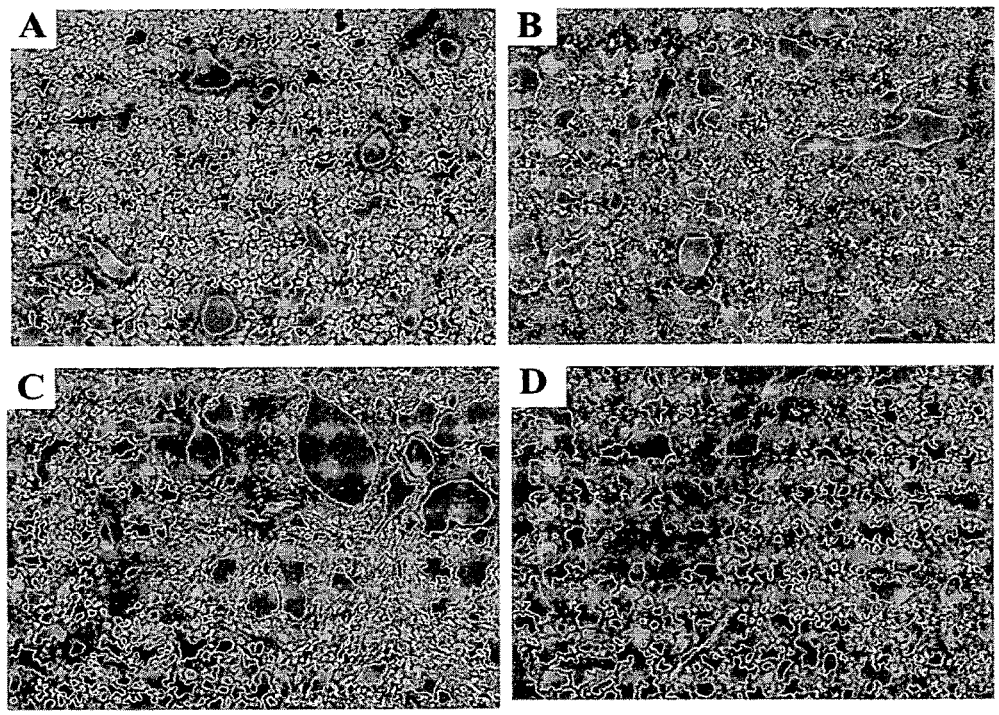
FIG. 2 shows representative photomicrographs of immunohistochemically stained lung tissue derived from naïve and γ-flu vaccinated mice. The effect of γ-flu (gamma-irradiated influenza virus) vaccination on lung inflammation in (A) naïve mice, (B) naïve mice at day 6 post A/WSN, (C) mice vaccinated with γ-flu and challenged with the homologous strain A/WSN and (D) mice vaccinated with γ-flu and challenged with the heterologous strain A/PC, is shown.
Figure 3:
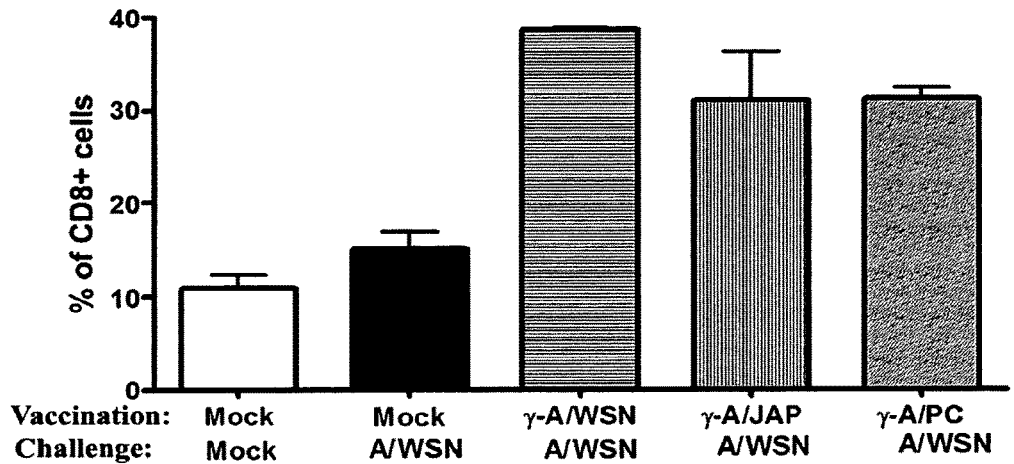
FIG. 3 is a bar graph illustrating the effect of γ-flu vaccination on CD8+ T cell infiltration. Mock or gamma-irradiated influenza virus (γ-A/WSN, γ-A/JAP, γ-A/Pc) were used to vaccinate animals intravenously. Four weeks later, mice were challenged intranasally with A/WSN. Six days following A/WSN challenge, 3 mice from each group were sacrificed and percentages of CD8+ T cells within the total lung infiltrates were estimated by FACS.

Prior intravenous (i.v.) injections of γ-ray-inactivated homologous or heterologous influenza A strains enhanced the survival rate of $LD_{50}$ A/JAP challenged mice (Table 5). When compared to unvaccinated mice, all vaccinated groups (A, B, and C) showed significant reductions in weight loss following intravenous infection with A/JAP (P value of <0.01 using ANOVA test) (FIG. 1). Naïve unvaccinated animals presented a weight loss of >30% at 6 days post A/JAP challenge. In comparison, all vaccinated animals only showed mild weight loss of <10% (FIG. 1).

γ-Flu Vaccination Reduces Lung Inflammation Following Challenge with Influenza A/WSN In addition to mortality and weight loss following A/JAP infection, lung inflammation and infiltration following A/WSN infection was assessed. Intranasal infection with A/WSN is characterized by a severe inflammatory response, evident in comparative histology of naïve (FIG. 2A) versus infected (FIG. 2B) lungs. Inflammation is substantially reduced in γ-flu vaccinated animals challenged with homologous (FIG. 2C) or heterologous (FIG. 2D) influenza virus. Despite lower total inflammation, CD8+ T cells preferentially infiltrated lungs of γ-flu vaccinated animals (FIG. 3).

γ-Flu Induces Cross-Reactive Cytotoxic (Tc) Cell Responses

Figure 4:
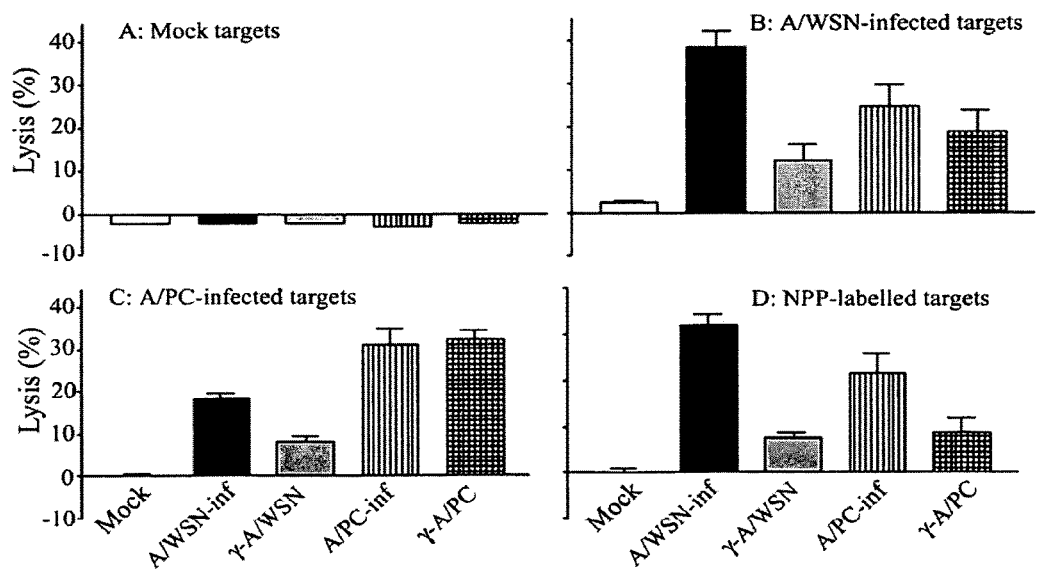
FIG. 4 provides a series of bar graphs illustrating cross-reactive cytotoxic T lymphocyte (CTL) responses induced by γ-flu. BALB/c mice were either infected or vaccinated with A/WSN, γ-A/WSN, A/PC, or γ-A/Pc, and their splenocytes tested for killing activity against (A) mock, (B) A/WSN-infected, (C) A/PC-infected, and (D) NPP-labelled P815 targets.
Figure 5:
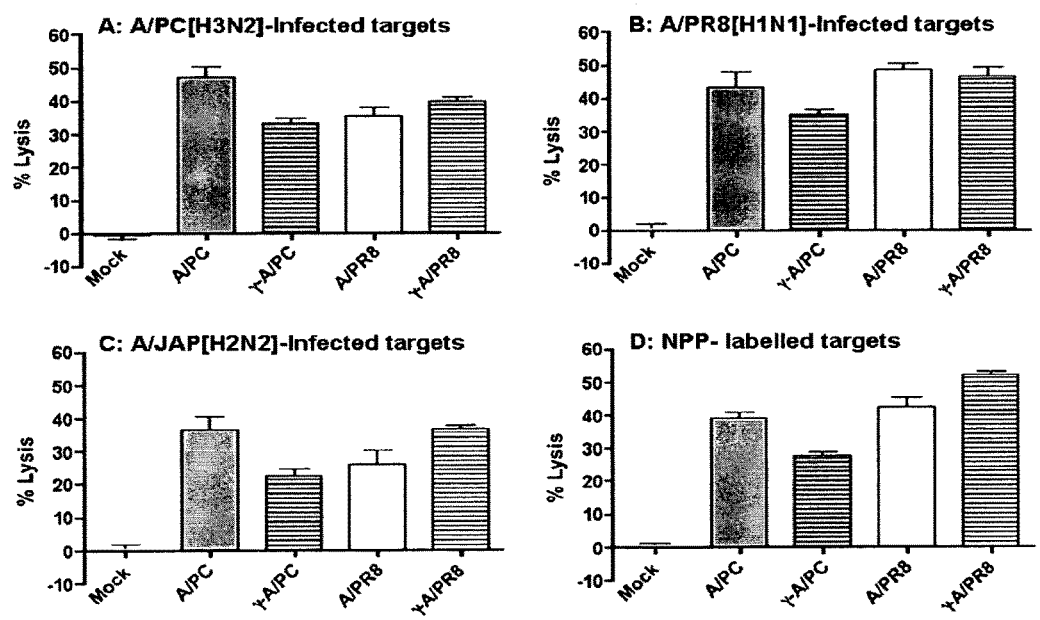
FIG. 5 provides a series of bar graphs illustrating cross-reactive cytotoxic T cell responses induced by γ-flu. Splenocytes from BALB/c mice infected or vaccinated with A/PR8, γ-A/PR8, A/PC, or γ-A/PC were tested for their killing activity on mock (data not shown), (A) A/PC[H3N2]-infected, (B) A/PR8 [H1N1]-infected, (C) A/JAP [H2N2]-infected, and NPP-labelled P815 targets.

The protective effect of γ-flu against infection with homologous virus is expected to involve both humoral and cellular immunity. The mechanism responsible for the observed cross-protective immunity (protection from heterologous infection) may be at least in part cytotoxic T (Tc) cell-mediated. To test whether γ-flu induces cross-reactive Tc cell responses, A/WSN and A/PC and their corresponding γ-flu preparations were used to infect or vaccinate mice, and splenic effectors were then tested for their killing activity on mock, A/WSN-infected, A/JAP-infected, and target cells modified with the appropriate $K^d$ restricted nucleoprotein derived peptide (NPP). As shown in FIG. 4, effector splenocytes from infected and vaccinated animals lysed homologous and heterologous virus-infected P815 targets. In addition, all splenocytes, except those from mock-infected mice, showed killing activity on nuclear protein peptide labelled targets.

Example 3: Intranasal Vaccination with Gamma-Irradiated Influenza a Virus Protects Against H5N1 (Bird Flu)

(i) Materials and Methods

Animals 10 week old BALB/c mice were utilised in this experiment.

Viruses

Virus stocks of two A strains of influenza viruses (A/PR8 [H1N1] and A/PC [H3N2]), were grown in embryonated hen eggs and purified by temperature-dependent adsorption to chicken red blood cells, and virus titres estimated by standard plaque assays on Madin-Darby canine kidney (MDCK) cells and titres expressed as pfu/mls.

γ-Irradiation of Influenza Strains

The purified stocks were exposed to $1\times10^6$ rad (10 kGy) of γ-rays (ANSTO, Lucas Height, Australia) as described in Example 2 above. The residual viral infectivity in irradiated stocks was tested by using embryonated hen eggs. Virus stocks were sterile but retained full haemagglutinating activity after irradiation.

Statistics

All statistical analyses were conducted using GraphPad InStat software. Fisher's exact and Chi Square tests were used to compare survival rates for significant differences.

Cross-Reactive Cytotoxic T Cell Responses in BALB/c Mice

Ten week old BALB/c mice were either infected or vaccinated with A/PR8, γ-A/PR8, A/PC, or γ-A/PC. Six-days later, splenocytes from these mice were tested for their killing activity on mock, A/PC-, A/PR8-, A/JAP-infected, and NPP-labelled P815 targets using $Cr^{51}$ release assay as described above in Examples 1 and 2 above.

Intranasal Vaccination with γ-Flu for Homologous and Heterologous Protection

Groups of mice were vaccinated with either $3.2\times10^6$ pfu/mouse of γ-A/PR8 (n=10), γ-A/PC (n=10), formalin inactivated A/PC (n=8), or mock treated (n=10). Four weeks post vaccination mice were challenged intranasally with $2\times10^5$ pfu/mouse of A/PR8 and monitored for weight loss and mortality for 21 days.

Intranasal γ-Flu Vaccination Versus Other Routes of Administration

Different routes (intranasal (i.n.), intravenous (i.v.), intraperitoneal (i.p.) and subcutaneous (S.c.) of inoculation were used to vaccinate BALB/c mice (10 mice/group) with $3.2\times10^6$ pfu equivalent of γ-A/PC. Three weeks post vaccination mice were challenged i.n. with a lethal dose of live A/PR8 ($6\times10^2$ pfu) and monitored for mortality and clinical symptoms using a 30% body weight loss as the end point.

Base Parameters of Lethal H5N1 Infections in BALB/c Mice

Figure 6:
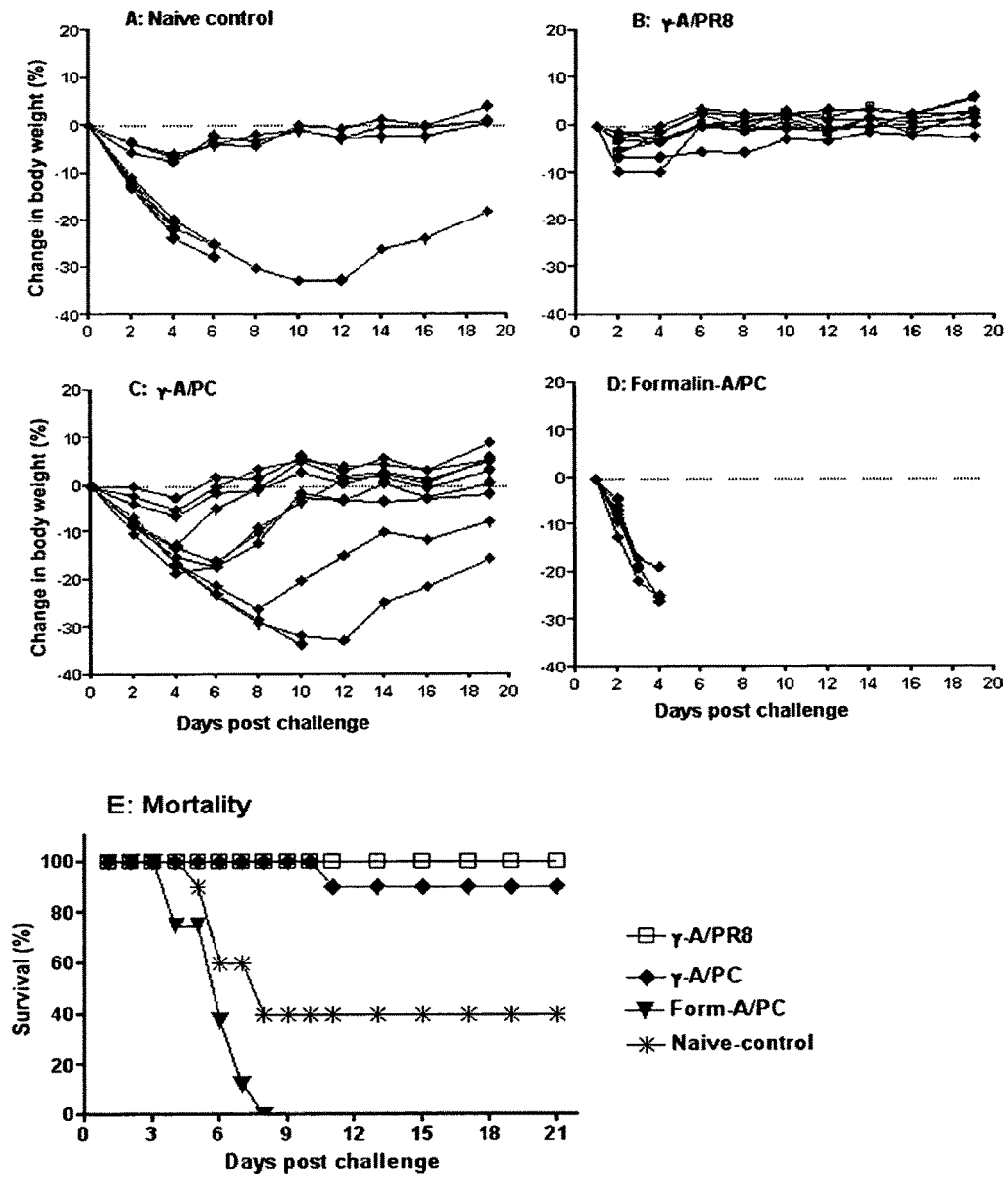
FIG. 6 shows a series of graphs illustrating mortality in mice after challenge with a lethal dose of A/PR8. Groups of mice: (A) naïve (unvaccinated), (B) vaccinated intranasally with A/PR8 γ-flu (n=10), (C) vaccinated intranasally with A/PC γ-flu (n=10), and (D) vaccinated intranasally with formalin inactivated A/PC (n=8), were challenged intranasally with $3 \times 10^2$ HAU ($2 \times 10^5$ pfu/mouse) of A/PR8. Weight loss and mortality (E) was monitored for 21 days post challenge. The end of an individual mouse's weight track indicates death of the animal.

Groups of 10-week-old BALB/c mice were infected intranasally with 10-fold serial dilutions of H5N1 virus stock. Mice were monitored for weight loss and morbidity. The end of an individual mouse's weight track indicates sacrificing due to ~25% weight loss.

Protection Against H5N1 Using Intranasal Vaccination with γ-FLU (γ-A/PR8[H1N1])

The protective effect of γ-flu against a lethal challenge of H5N1 was tested. BALB/c mice (10 mice/group) were either mock treated or vaccinated intranasally with a single dose of γ-A/PR8 [H1N1] ($3.2\times10^6$ pfu equivalent/mouse). Four weeks post vaccination mice were challenged intranasally with 3× mouse infectious dose 50 (3×MID50) of A/Vietnam/1203/2004 [H5N1] and monitored daily for mortality and clinical symptoms for 21 days using a 20% body weight loss as the end point.

Real-Time PCR (RT-PCR) to Estimate the Effect of γ-Flu Vaccine on H5N1 Genetic Load Following the addition of 100 μl of lung or brain homogenate into 600 μl of RLT buffer, RNA was extracted using an RNeasy Mini Kit (Qiagen) according to the manufacturer's instructions. The total RNA concentration of each sample was determined by spectrophotometry and adjusted to 40 ng $\mu l^{-1}$ with nuclease free water. Standardised amounts (200 ng) of template were subsequently reverse transcribed using the TaqMan Reverse Transcription Reagents kit (Applied Biosystems) in 20 μl reactions following the recommendations of the manufacturer. For quantitation of viral cDNA, universal influenza virus type A-specific primers and TaqMan probe, which amplified and detected a product from within the viral matrix gene, were use as described previously (see Heine, H. G., et al, 2007 "*Rapid detection of highly pathogenic avian influenza H5N1 virus by TaqMan reverse transcriptase polymerase chain reaction*" Avian Dis. 51: 370-372).

Reactions were performed in triplicate and contained 12.5 μl of TaqMan 2× Universal PCR Master Mix, 900 nM of each primer, 250 nM of probe, 2 μl of cDNA template and 6.8 μl of water. Separate triplicate reactions to quantify 18S rRNA (TaqMan Ribosomal Control Reagents, Applied Biosystems) were also performed to exclude the presence of PCR inhibitors in all samples tested. Reactions were performed in 96-well plates using the 7500 Fast Real-Time PCR System (Applied Biosystems) and the following cycling parameters: 50° C. for 2 min; 95° C. for 10 min; 45 cycles of 95° C. for 15 sec and 60° C. for 1 min. For relative quantitation of viral genetic loads, a standard curve was generated using, as template, 10-fold serial dilutions of extracted stock virus RNA in 40 ng $\mu l^{-1}$ of RNA prepared from uninfected mouse lung. To facilitate interpretation of data, 1 unit (1 U) of viral RNA was arbitrarily defined as the number of RNA molecules which, when reverse transcribed and subjected to real-time PCR, produced a $C_T$ value of 38.

(ii) Results

A/PR8 γ-Flu and A/PC γ-Flu Preparations Induce Cross-Reactive Cytotoxic T Cell Responses in BALB/c Mice The induction of cross-reactive cytotoxic T (Tc) cell responses was tested in γ-flu vaccinated mice. A/PR8 and A/PC and their corresponding γ-flu preparations were used to infect or vaccinate mice. Six days later, splenocytes from infected, vaccinated, and mock-immunized animals were tested for their killing activity on mock, A/PC-, A/PR8- or A/JAP-infected and target cells modified with the appropriate $K^d$ restricted nucleoprotein derived peptide (NPP) using $Cr^{51}$ release assay (as described in Examples 2 and 3 above). As shown in FIG. 5, effector splenocytes from influenza-infected and γ-flu vaccinated animals induced killing activity against all influenza infected P815 targets regardless of the virus strains used. In addition, all splenocyte populations, except those from mock-infected mice, showed killing activity on influenza virus nuclear protein peptide labelled targets. These data illustrate the ability of γ-flu preparations to induce cross-reactive Tc cell responses in mice.

Intranasal γ-Flu Vaccination Protects Against Lethal Dose of Influenza A/PR8

Considering that whole virus vaccine elicits complications due to a high reactogenicity and that γ-irradiation has little impact on viral immunogenecity (as shown above), the intranasal administration of γ-flu was tested. The efficacy of the intranasal γ-flu vaccine formulation was compared to that of chemically inactivated vaccine preparations used in current human influenza virus preparations. Mice were vaccinated intranasally with equal doses of one of three inactivated virus preparations (formalin A/PC, γ-A/PC [H3N2] or γ-A/PR8 [H1N1]). In these experiments mice were vaccinated with a single dose only and challenged 4 weeks later with a lethal dose (>300× the lethal dose 50) of A/PR8. Mice were weighed and observed for mortality for 3 weeks post challenge (FIG. 6). γ-A/PR8 vaccinated animals fully recovered with little weight loss after challenge with homologous virus (FIG. 6B). Challenge of γ-A/PC vaccinated animals with A/PR8 (i.e. with heterologous virus) caused in a proportion of animals weight loss with most starting recovery by day 4 (FIG. 6C) coinciding with the peak of a memory Tc cell response (Müllbacher and Tha Hla, 1993, "In vivo administration of major histocompatibility complex class I-specific peptides from influenza virus induces specific cytotoxic T cell hyporesponsiveness", Eur. J. Immunol., 23, 2526-2531). The survival rate of γ-A/PC vaccinated animals is significant compare to unvaccinated group (p<0.05 using Chi-square test). All mice vaccinated with formalin inactived vaccine preparations rapidly lost weight (FIG. 6D). The mortality data (FIG. 6E) confirm the morbidity data and show that intranasal vaccination with γ-flu protects from homologous and heterologous influenza A challenges.

Intranasal γ-Flu Vaccination Versus Other Routes of Administration

Figure 7:
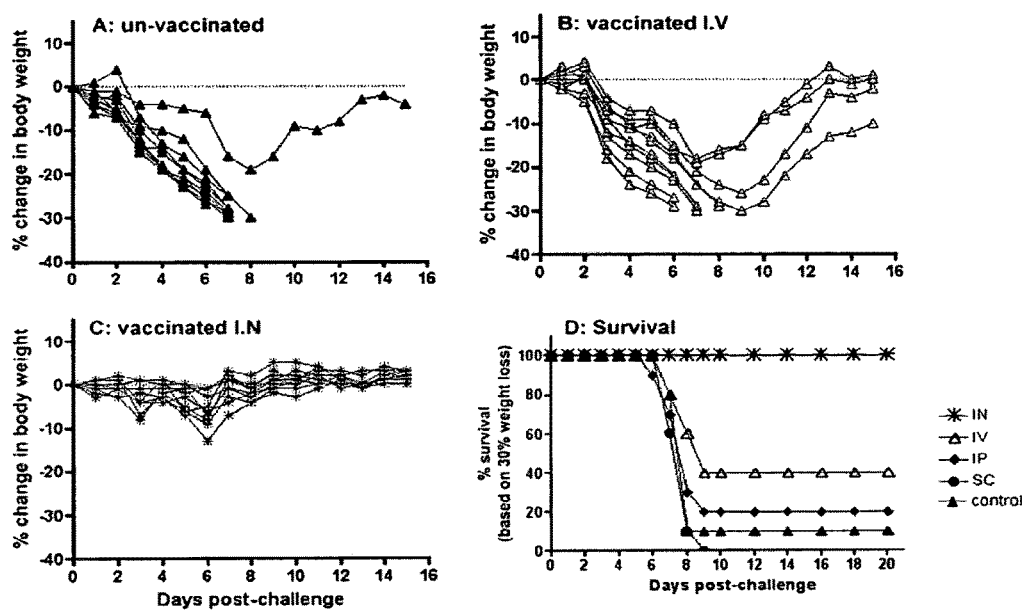
FIG. 7 shows a series of graphs illustrating that intranasal vaccination with γ-flu provides superior protection to heterotypic virus challenge. Groups of 10 BALB/c mice were either mock treated (A) or vaccinated with γ-A/PC ($3.2 \times 10^6$ PFU equivalent) intravenously (B) or intranasally (C). Mice were challenged intranasally after 3 weeks with a lethal dose ($6 \times 10^2$ PFU) of A/PR8 and weight recorded daily for 21 days. Survival defined by 30% weight loss (D) of mice mock treated, or vaccinated i.n., i.v., i.p., or s.c. and challenged as for (A-C) and monitored for 21 days.

Different routes (intranasal (i.n.), intravenous (i.v.), intraperitoneal (i.p.) and subcutaneous (S.c.) of inoculation were used to vaccinate BALB/c mice (10 mice/group) with $3.2 \times 10^6$ plaque forming units (PFU) equivalent of γ-A/PC. Three weeks post vaccination mice were challenged i.n. with a lethal dose of live A/PR8 ($6 \times 10^2$ PFU) and monitored for mortality and clinical symptoms using a 30% body weight loss as the end point (FIG. 7). All i.n. vaccinated animals fully recovered with little if any weight loss after challenge with heterotypic virus (FIG. 7C). In contrast, the majority of unvaccinated (FIG. 7A), i.v. vaccinated (FIG. 7B), and i.p. and S.c. vaccinated (data not shown) mice lost weight progressively to reach 30% body weight loss at days 7 and 8 post infection. The survival data (FIG. 7D) show that despite the use of unnaturally high challenge doses of A/PR8, i.n. vaccinated mice survived at significant levels the heterotypic challenge (P<0.05 using Fisher's Exact test).

Base Parameters of Lethal H5N1 Infections in BALB/c Mice

Figure 8:
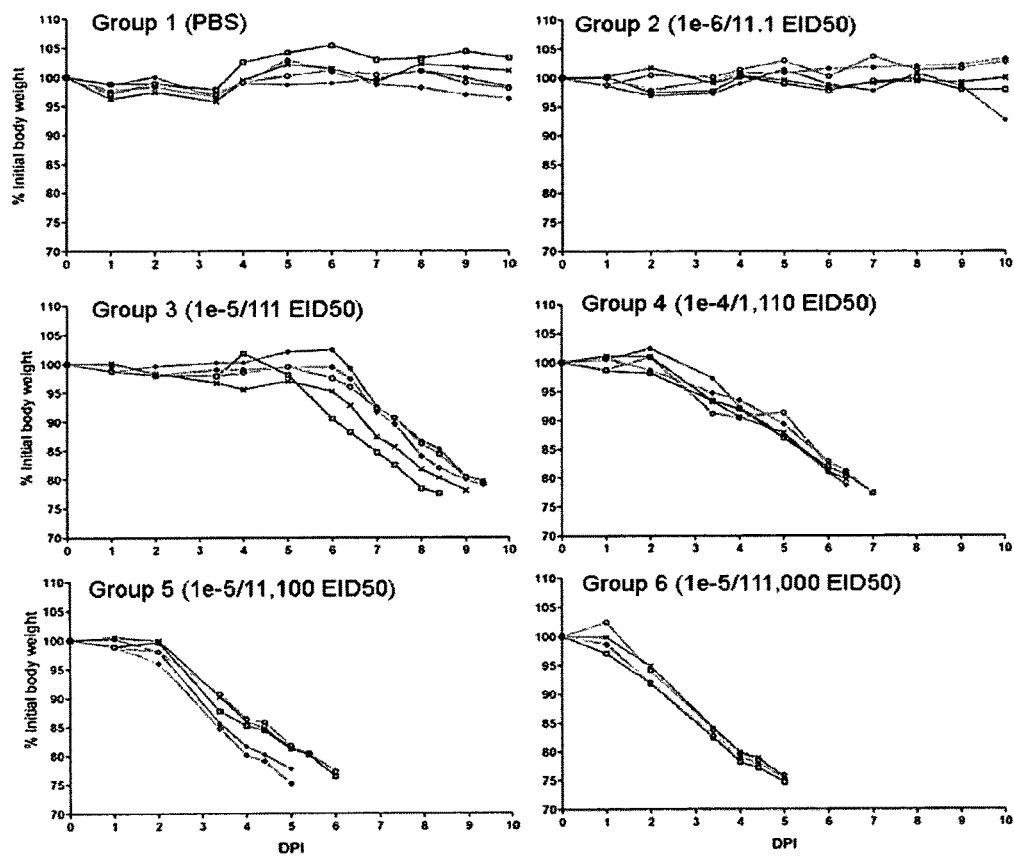
FIG. 8 shows a series of graphs illustrating weight loss following intranasal infection with H5N1 (A/Vietnam/1203/2004). Infected mice were monitored for weight loss and morbidity. The end of an individual mouse's weight track indicates sacrificing due to ~25% weight loss.

Weight loss in BALB/c mice was assessed following intranasal infection with H5N1 (A/Vietnam/1203/2004). As shown in FIG. 8, groups of 5 mice were challenged with either diluent alone (Group 1) or 10-fold serial dilutions of stock virus (Groups 2-6, in order of increasing concentration of inoculum). Mice were weighed and observed for morbidity and sacrificed before reaching a body weight loss of >25%. Mice infected with 111 EID50 (group 3) and those infected with 11100 EID50 (group 5) started to show weight loss by day 6 and 2 post-infection, respectively.

Protection Against H5N1 Avian Influenza Virus

Figure 9:
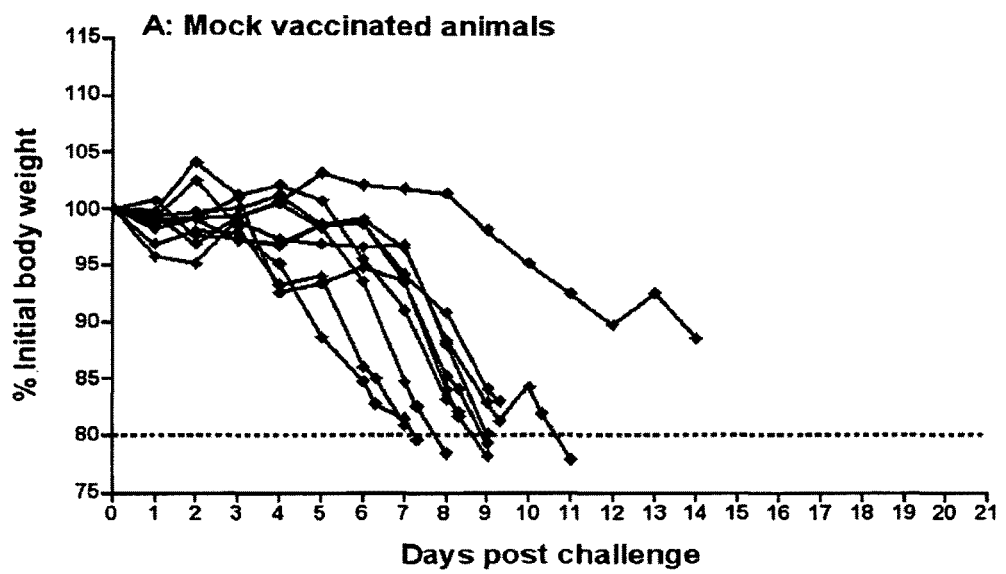
FIG. 9 shows two graphs illustrating body weight and mortality of BALB/c mice following challenge with H5N1. Groups of 10 mice were either (A) mock treated or (B) vaccinated with γ-A/PR8 [H1N1] intranasally. Weight was recorded daily for 21 days.
Figure 9:
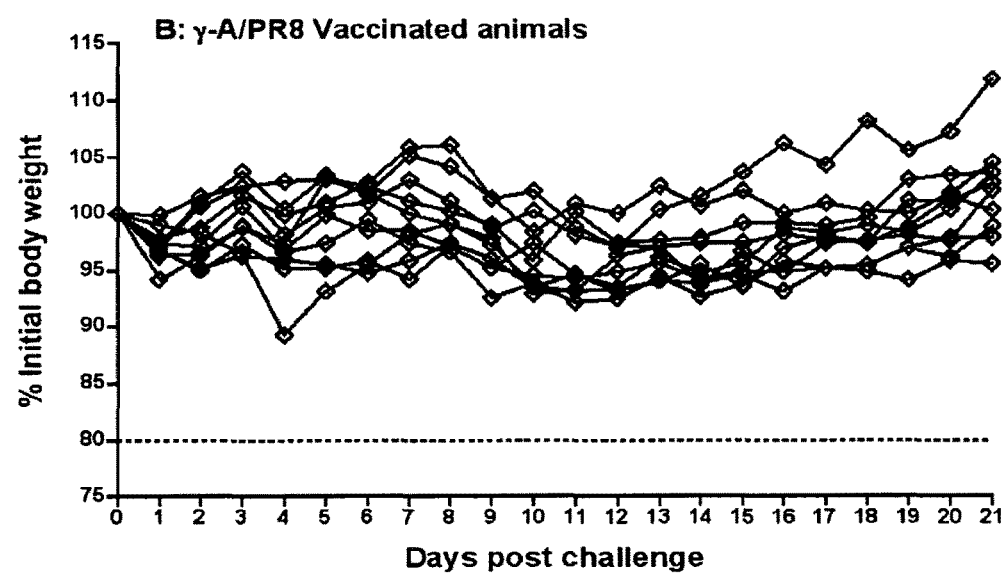

The protective effect of γ-flu against a lethal challenge of H5N1 as tested. BALB/c mice (10 mice/group) were vaccinated intranasally with a single dose of γ-A/PR8 [H1N1] ($3.2 \times 10^6$ PFU equivalent/mouse). Four weeks post vaccination mice were challenged intranasally with 3× mouse infectious dose 50 (3×MID50) of A/Vietnam/1203/2004 [H5N1] and monitored for mortality and clinical symptoms using a 20% body weight loss as the end point (FIG. 9). All ten mice in the control group (mock vaccinated) developed clinical signs consistent with H5N1 infection and were euthanized between DPI 7 and 14 days post infection according to the experimental end-points that were approved by the AEC (where weight loss of 20% or more was observed, where any neurological sign was detected or where the infection had led to an inability to eat/drink (e.g. severe hunching, severe dehydration, inactivity)) (FIG. 9A). In general, unvaccinated mice developed greasy/ruffled fur from days 4 post-infection, two mice developed neurological signs categorised by an abnormal hindlimb gait and hindlimb weakness at which time they were euthanized, and all other mice were euthanized at ~20% body weight loss (with varying degrees of depression, inactivity and dehydration).

In contrast, all vaccinated mice (gamma-A/PR8 [H1N1]) remained bright and active throughout the study and were euthanized at the conclusion of the trial on day 21 post-infection (FIG. 9B). A single animal lost 11% body weight by day 4 post-infection but was bright and active and regained the pre-challenge weight by the end of the trial. In general, all mice survive the lethal challenge with H5N1 and some animals gained more body weight to exceed their pre-challenge weight.

Intranasal γ-Flu Vaccination Results in Early Clearance of H5N1 from the Lung

As shown above, all vaccinated mice survived the lethal challenge with H5N1. Therefore, the data demonstrates that a single dose of γ-flu preparation administered intranasally induces cross-protective immunity in mice against a lethal challenge with H5N1 virus. Quantitation of viral infectivity and viral genetic loads confirmed the protective effect of γ-A/PR8[H1N1] against avian influenza and show clearance of H5N1 virus from lung tissues by day 6 post-challenge (Table 6). The detection of viral infectivity and viral RNA in the lung of one vaccinated animal on day 3 post-challenge but none at day 6 indicates that the observed cross-protective immunity is most likely mediated by memory Tc cells, which express accelerated activation kinetics over that of naïve Tc cells, as described previously (Bennink et al, 1978, *"Influenzal pneumonia: early appearance of cross-reactive T cells in lungs of mice primed with heterologous type A viruses*", Immunology 35: 503-509).

TABLE 6

H5N1 infectivity and viral genetic loads in lung and brain

| | | | Infectivity | | Genetic load | |
|---|---|---|---|---|---|---|
| DPI* | Treatment | Mouse | Lung | Brain | Lung | Brain |
| 3 | Mock | 1 | 6.5 | ≤3.2 | 3.4 ± 0.03 | —† |
| | | 2 | 5.8 | — | 2.0 ± 0.02 | — |
| | Vaccinated | 1 | — | — | — | — |
| | | 2 | 7.4 | — | 3.6 ± 0.02 | — |
| 6 | Mock | 1 | 6.4 | — | 4.2 ± 0.003 | — |
| | | 2 | 6.4 | — | 4.2 ± 0.01 | — |
| | | 3 | 7.4 | 5.0 | 4.4 ± 0.03 | 3.0 ± 0.03 |
| | Vaccinated | 1 | — | — | — | — |
| | | 2 | — | — | — | — |
| | | 3 | — | — | — | — |

Viral infectivity and relative viral genetic loads are expressed as $\log_{10}$ $TCID_{50}$ $g^{-1}$ and $\log_{10}$ U per 20 ng of extracted RNA (geometric mean ± s.d. of triplicate reactions), respectively, where 1 unit (1 U) of viral RNA is arbitrarily defined as the number of RNA molecules which, when reverse transcribed and subjected to real-time PCR, produced a $C_T$ value of 38.

*Days post infection.

†Undetectable (< $10^{3.2}$ $TCID_{50}$ $g^{-1}$ (infectivity) or < 1 U per 20 ng of extracted RNA (genetic load)).

Example 4: Gamma-Ray Inactivated Influenza a Viruses Induce Cross-Protective Immunity in Mice that is Primarily Mediated by Cytotoxic T Cells (i) Materials and Methods Cells and Viruses P815 mastocytoma and Madin-Darby canine kidney (MDCK) cells were maintained in EMEM plus 5% FCS at 37° C. in a humidified atmosphere with 5% $CO^2$. The influenza type A viruses, A/PR/8 [A/Puerto Rico/8/34 (H1N1)] and A/PC [A/Port Chalmers/1/73 (H3N2)] were grown in 10-day-old embryonated chicken eggs. Each egg was injected with 0.1 ml normal saline containing 1 hemagglutinin unit (HAU) of virus, incubated for 48 hours at 37° C., then held at 4° C. for overnight. The amniotic/allantoic fluids were harvested, pooled and stored at −80° C. Titres were $10^7$ PFU/ml (A/PC) and $2\times10^8$ PFU/ml (A/PR8) using plaque assays on MDCK cells. Viruses were purified using chicken red blood cells for vaccine preparation as described in (Sheffield, et al. (1954), "*Purification of influenza virus by red-cell adsorption and elution*", British journal of experimental pathology, 35:214-222). Briefly, infectious allantoic fluid was incubated with red blood cells for 45 minutes at 4° C. allowing the viral hemagglutinin to bind red blood cells, and then centrifuged to remove the allantoic fluid supernatant. The pellets were resuspended in normal saline, incubated for 1 hour at 37° C. to release the red blood cells from the virus and then centrifuged to remove the red blood cells and collect the virus in the supernatant. Purified A/PC stock titre was $5\times10^8$ PFU/ml.

Virus Inactivation

For formalin inactivation, the viruses were incubated with 0.2% formalin at 4° C. for a week. Formalin was then removed by pressure dialysis using normal saline for 24 hours at 4° C. The dialysis method was adapted from Current Protocols in Immunology (see Andrew et al., (2001), "*Dialysis and concentration of protein solutions*", in *Current protocols in immunology*, Coligan et al., (eds), Appendix 3: Appendix 3H). For UV inactivation, the viruses were placed in 60-mm petri dishes with a fluid depth of 10 mm. The virus was exposed to 4000 ergs per $cm^2$ for 45 minutes at 4° C. For gamma ray inactivation, influenza viruses received a dose of 10 kGy from a $^{60}Co$ source (Australian Nuclear Science and Technology Organization—ANSTO). The virus stocks were kept frozen on dry ice during gamma irradiation. Loss of viral infectivity was confirmed by titration of inactivated virus preparations in eggs. The HAU titres of inactivated virus stock were determined to be $7.3\times10^4$ HAU/ml for gamma-inactivated A/PC, $2.4\times10^4$ HAU/ml for formalin- and UV-inactivated A/PC.

Protection Experiments

BALB/c, C57BL/6, 129Sv/Ev, β2-microglobulin (β2 $m^{-/-}$), Ig μ-chain ($\alpha MT^{-/-}$), perforin ($Prf^{-/-}$), IFN-γ receptor ($IFN-IIR^{-/-}$) and $MHC-II^{-/-}$ mice were bred under specific pathogen-free conditions. 10–44-week-old females were used. Mice were immunized intranasally with inactivated virus preparations ($3.2\times10^6$ PFU equivalent). For lethal challenge, at 3 weeks post-immunization, mice were infected intranasally with A/PR8 ($7\times10^2$ PFU). Mice were weighed daily and monitored for mortality until day 20 post-challenge.

Adoptive Immune Lymphocyte Transfer Experiment 10-week-old donor BALB/c mice were immunized intravenously with γ-irradiated A/PC ($1\times10^8$ PFU equivalent). Splenocytes were collected at week 3 post immunization. Single-cell suspensions were prepared and red blood cells were lysed. The splenic lymphocytes were separated into B and T cell populations by passing the cells through nylon wool columns. 2 ml of $5\times10^7$ cells/ml were loaded onto columns and incubated for 2 hours at 37° C. The columns were washed with warm (37° C.) Hanks balanced salt solution+5% FCS and non-adherent T cells in the first effluent were collected. Nylon wool-bound B cells were then collected by washing the columns with cold (4° C.) Hanks-balanced salt solution. Purity of T (82.8%, +7.94% B cell) and B (84.2%, +8.3% T cell) populations was confirmed by flow cytometric analysis. Small samples of purified splenocytes were washed in PBS with 2% FCS. Fc receptors were blocked by incubation with mouse CD16/CD32 (Fcγ III/II receptor) Ab (BD Pharmingen) for 20 min at 4° C. Cells were washed and further incubated with a mixture of fluorescent-conjugated anti-CD3, anti-CD8, anti-CD19 (BD Pharmingen) Abs. Dead cells were labelled with 7-aminoactinomycin D (Sigma-Aldrich). Stained cells were quantified using a FACS Calibur (Becton Dickinson). Purified T or B cells ($1.1\times10^7$ cells in a volume of 0.2 ml) were intravenously injected into recipient mice, which were then challenged with A/PR8 ($7\times10^1$ PFU) intranasally at 3 hours after the adoptive cell transfer. Mice were monitored for body-weight loss and mortality until day 20 post-challenge.

Passive Serum Transfer Experiment

Sera from intranasally immunized mice with γ-irradiated A/PC were collected at 3 weeks post-immunization. The pooled immune sera were heated for 30 minutes at 56° C. to inactivate complement. Recipient mice received 200 μL of immune sera intravenously. After two hours, the recipient mice were challenged with A/PR8 ($7\times10^2$ PFU). Mice were monitored for body weight and mortality until day 20 post challenge.

Plaque Reduction Assay

Immune sera were collected 3 weeks post-immunization from mice vaccinated with live, γ-irradiated, formalin or UV-inactivated A/PC. After heat inactivation of serum samples at 56° C. for 30 minutes, 190 μL of serially diluted (×10, ×30, ×90, ×270) serum was mixed with 10 μL virus (A/PC or A/PR8 strain) suspension containing roughly 100 PFU. After 60 minute incubation at 37° C. the residual virus infectivity was measured by plaque assay on MDCK cells.

Cytotoxic T Lymphocyte (Tc Cell) Assay

Influenza-specific Tc cells were generated by intravenously injecting BALB/c mice with either live A/PC (~$2\times10^6$ PFU) or inactivated A/PC (gamma-, formalin-, or UV-inactivated, ~$1\times10^8$ PFU equivalent). Spleens were harvested at 7 days post immunization and red blood cell-depleted cell suspensions were prepared for use as effector cells. Target cells were prepared by infecting P815 cells with live A/PC at a multiplicity of infection (m.o.i) of 1, followed by 1 hour incubation in medium containing 100–200 μCi of $^{51}Cr$. After washing, target cells were mixed with effector cells at different ratios in an 8 hour chromium release assay. The level of radioactivity in the supernatant was measured in a gamma counter. Specific lysis is given as mean percent lysis of triplicate wells and values were calculated using the formula: (experimental cpm–spontaneous cpm)/(maximal release cpm–spontaneous cpm)×100. For secondary ex vivo Tc cell responses, the primed mice received an intravenous secondary immunization at 3 months post primary immunization and splenocytes were harvested at 7 days post-immunization for chromium release assay.

(ii) Results

Role of Immune Sera and B and T Lymphocytes in Heterosubtypic Immunity Induced by γ-Irradiated Influenza Virus To determine the role of antibodies in cross-protective immunity, mice were intranasally immunized with either live A/PR8 ($7\times10^1$ PFU) or γ-irradiated A/PC ($3.2\times10^6$ PFU equivalent), and 3 weeks later blood was collected. Groups of naïve mice injected intravenously with 200 μl of either γ-irradiated A/PC immune serum, hyper-immune serum (from mice that received two doses of live A/PR8 at three week intervals) or pre-immune serum and challenged with a lethal dose of A/PR8 virus ($7\times10^2$ PFU) 2 hour post serum transfer.

Figure 10:
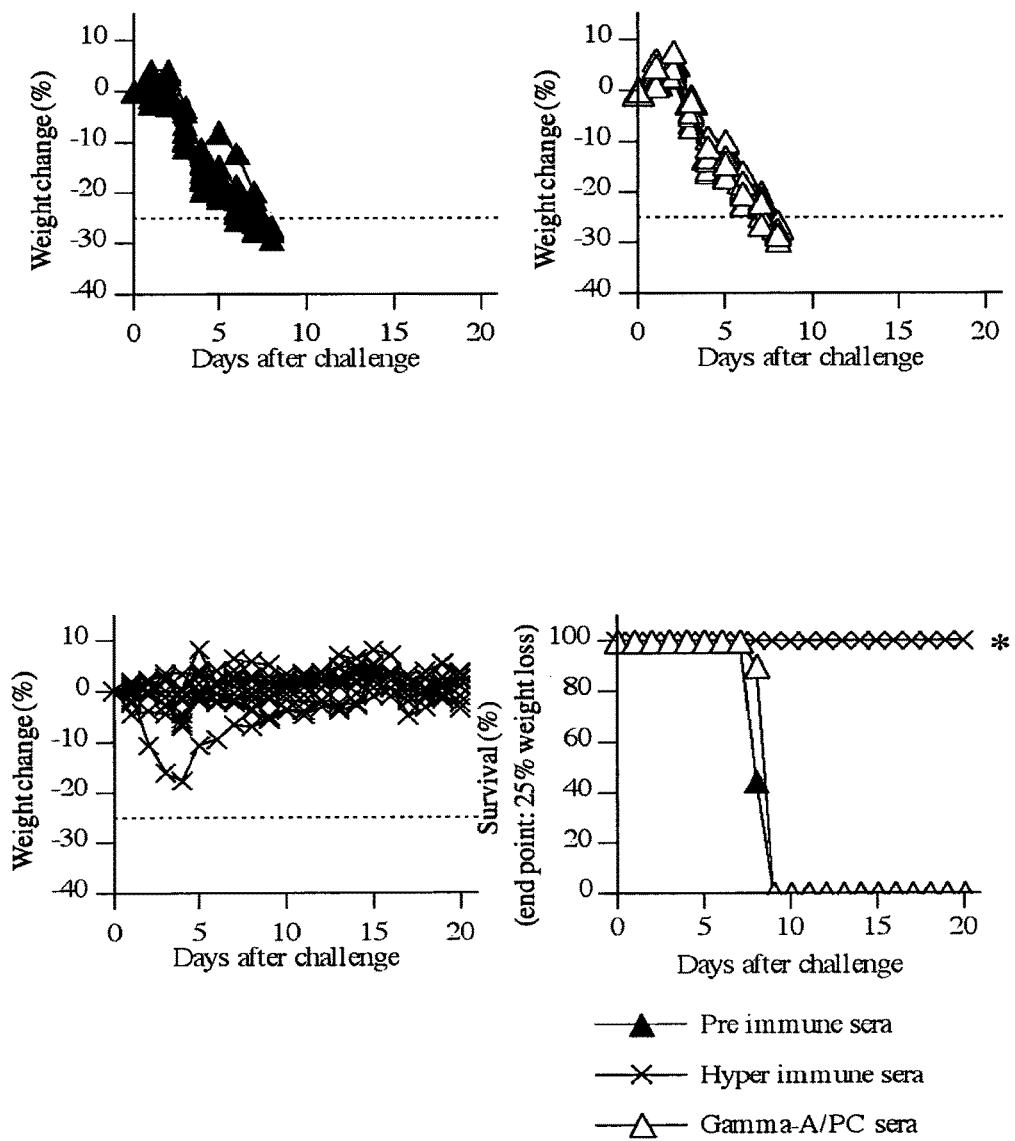
FIG. 10 provides a series of graphs showing that passive serum transfer fails to transfer heterosubtypic immunity induced by γ-irradiated A/PC to naïve mice. (A, B & C)=weight loss; (D)=mortality; Endpoint: 25% weight loss; * P<0.05 vs. control preimmune sera group; Fisher's exact test.

FIG. 10 illustrates that passive serum transfer fails to transfer heterosubtypic immunity induced by γ-irradiated A/PC, to naïve mice. Serum samples were pooled from donor mice immunized with either a single dose of γ-irradiated A/PC ($3.2\times10^6$ PFU equivalent) or two doses of live A/PR8 ($7\times10^2$ PFU) (hyper immune). Recipient mice (9~10 mice per group) were given intravenously 0.2 ml of immune sera or preimmune sera as a control. At two hours post serum transfer, mice were challenged intranasally with A/PR8 ($7\times10^2$ PFU). Mice were monitored daily for weight loss (FIGS. 10 A, B & C) and mortality (FIG. 10D). Naïve mice that received γ-irradiated A/PC immune serum developed clinical signs and weight loss similarly to those that received pre-immune serum (FIGS. 10A, C & D). These mice rapidly lost weight to reach the endpoint of 25% weight loss and accordingly were not protected from heterosubtypic challenge. In contrast, mice that received the hyper-immune serum were fully protected with virtually no weight loss when challenged with homologous A/PR8 ($7\times10^1$ PFU) (FIGS. 10B & D). These data indicate that γ-irradiated A/PC induced antibodies are not cross-protective.

Figure 11:
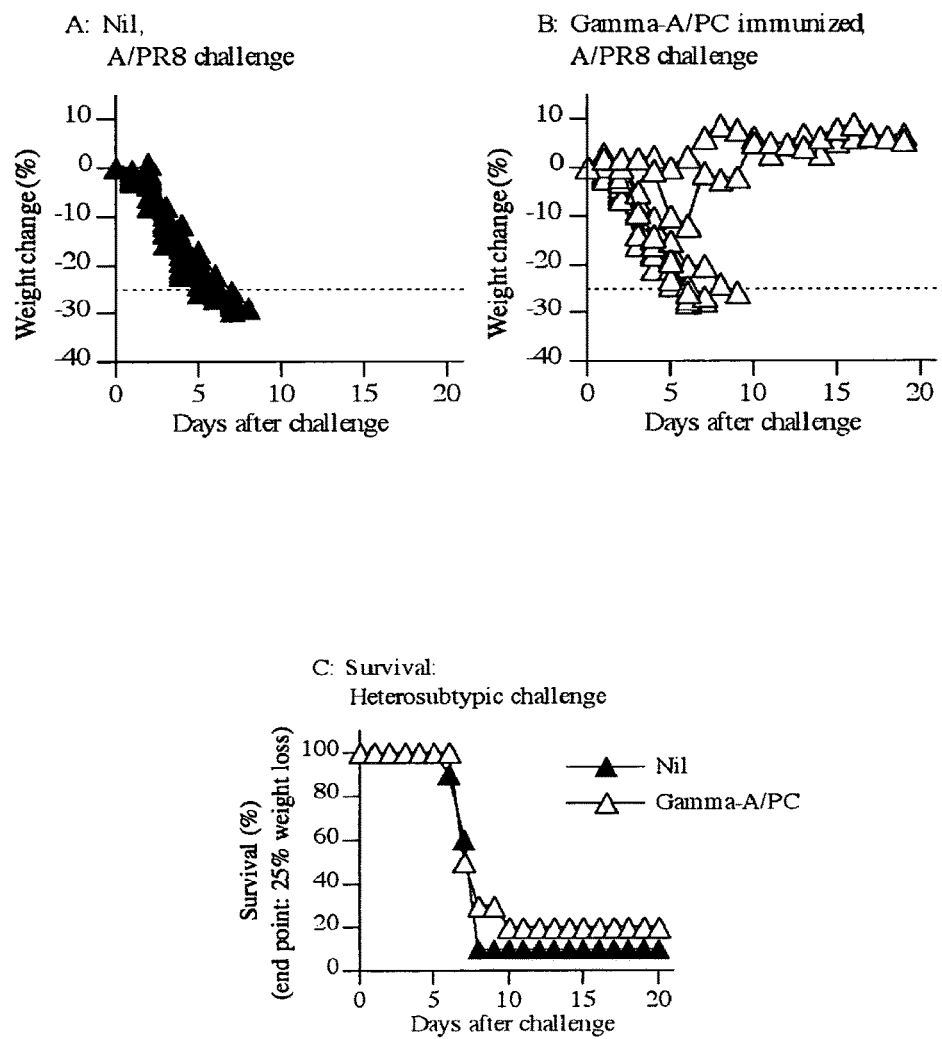
FIG. 11 provides a series of graphs showing an absence of heterosubtypic protection in B cell-deficient mice. (A)=weight loss in naïve mice; (B)=weight loss in immunized mice; (C)=mortality naïve/immunized mice.
Figure 12:
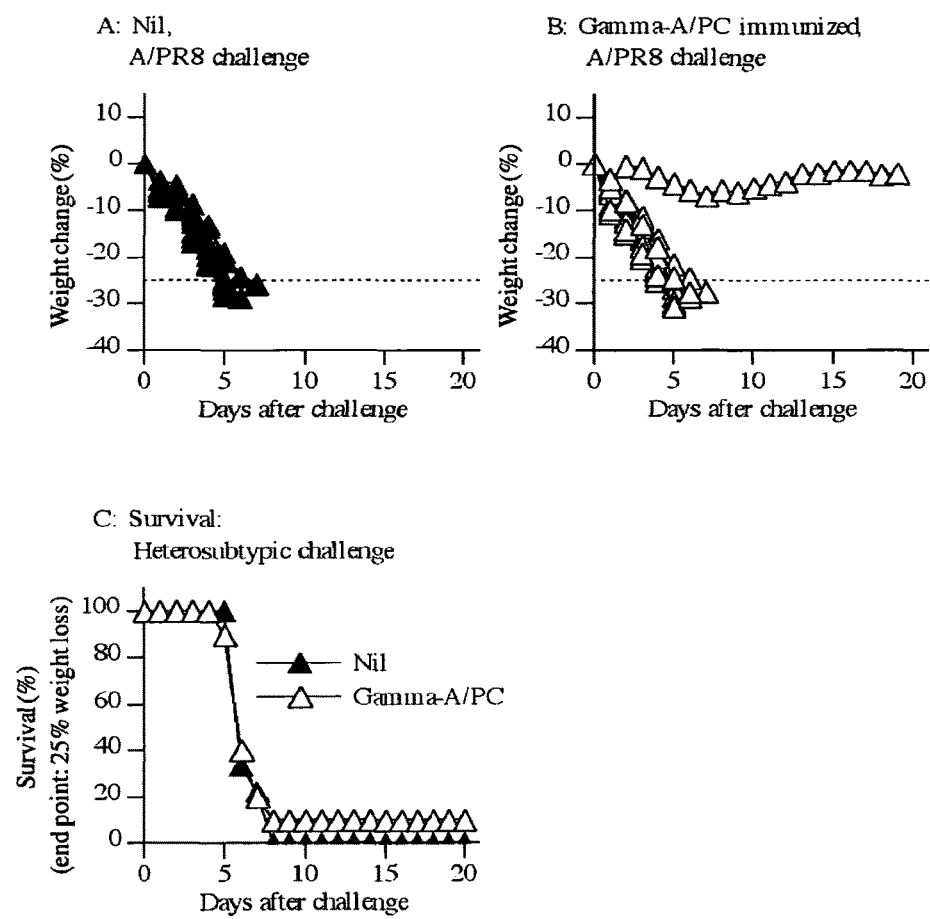
FIG. 12 provides a series of graphs showing an absence of heterosubtypic protection in MHC II deficient mice. (A)=weight loss in naïve mice; (B)=weight loss in immunized mice; (C)=mortality naïve/immunized mice.
Figure 13:
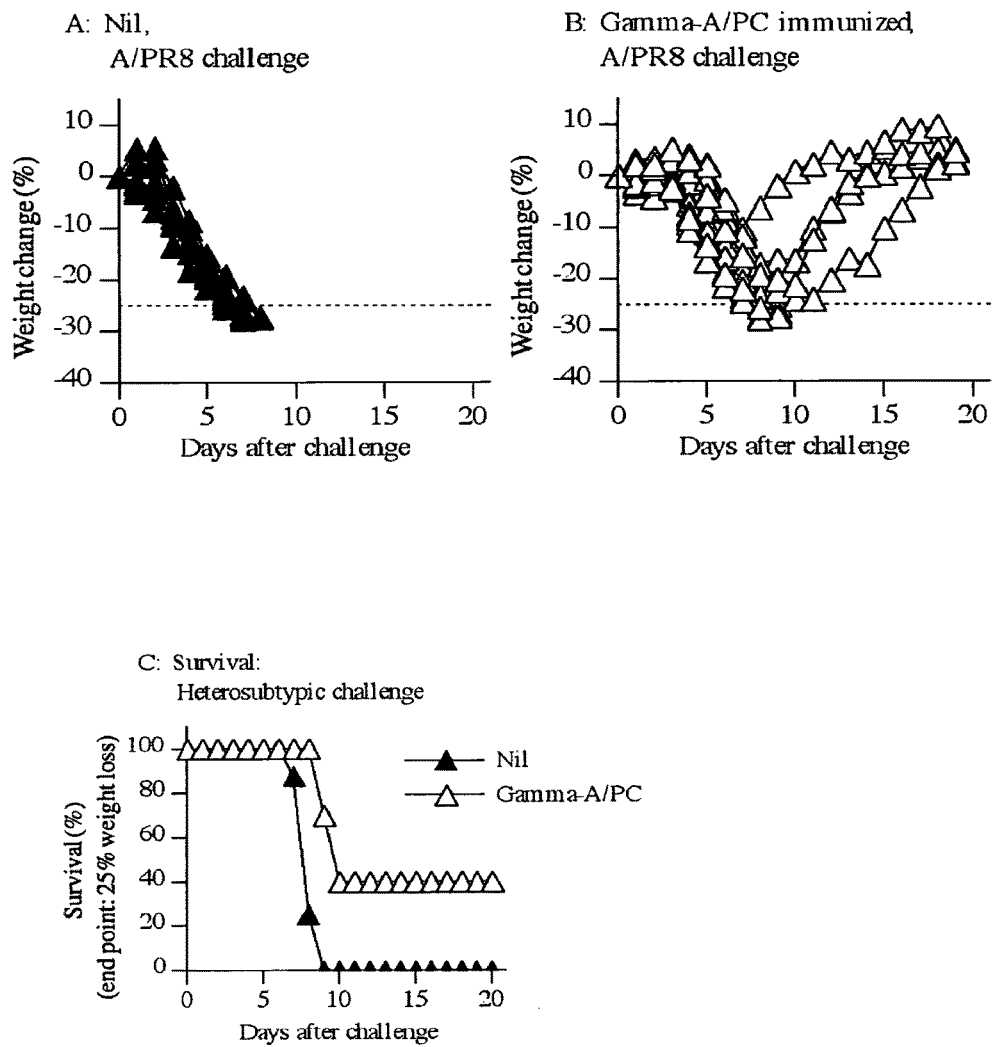
FIG. 13 provides a series of graphs showing a lack of heterosubtypic protection in β2M deficient mice. (A)=weight loss in naïve mice; (B)=weight loss in immunized mice; (C)=mortality naïve/immunized mice.

Secondly, B cell-deficient μMT$^{-/-}$ mice were used to assess the role of B cells in cross-protective immunity. 10-week-old μMT$^{-/-}$ mice were immunized intranasally with γ-irradiated A/PC ($3.2\times10^6$ PFU equivalent) and challenged with the heterosubtypic strain A/PR8 ($7\times10^2$ PFU) three weeks post-immunization. Mice were monitored daily for weight loss and mortality for 20 days. The vaccinated μMT$^{-/-}$ mice displayed a survival rate similar to that of naïve mice (FIGS. 11A, B & C), implying that an absence of B cells does impair the development of cross-protective immunity. Furthermore, intranasal vaccination with γ-irradiated A/PC ($3.2\times10^6$ PFU equivalent) failed to protect MHC-II$^{-/-}$ mice against heterosubtypic challenge with A/PR8 (FIGS. 12A, B & C). MHCII$^{-/-}$ mice were immunized intranasally with γ-irradiated A/PC ($3.2\times10^6$ PFU equivalent). 3 weeks post-immunization, naïve and immunized mice (9~10 mice per group) were challenged with heterosubtypic strain A/PR8 ($7\times10^2$ PFU). Mice were monitored daily for weight loss and mortality for 20 days. Vaccination with γ-irradiated A/PC failed to protect MHC-II$^{-/-}$ mice against heterosubtypic challenge with A/PR8. This provides evidence that B and CD4+ T cells participate in the induction of cross-protective immunity by γ-irradiated influenza virus.

β2M$^{-/-}$ mice which are deficient in CD8+ Tc cell responses were used to evaluate the contribution of CD8+ T (Tc) cells in the cross-protective immunity induced by intranasal immunisation with γ-irradiated A/PC ($3.2\times10^6$ PFU equivalent). A heterosubtypic challenge with A/PR8 ($7\times10^2$ PFU) caused a mortality rate of 60%, with the surviving mice losing over 10% of their body weight prior to their recovery (FIGS. 13B & C). Controls, unvaccinated mice infected with the same virus strain suffered 100% mortality (FIGS. 13A & C). This demonstrates a critical role for CD8+ T cells in the cross-protective immunity induced by γ-irradiated influenza virus.

Figure 14:
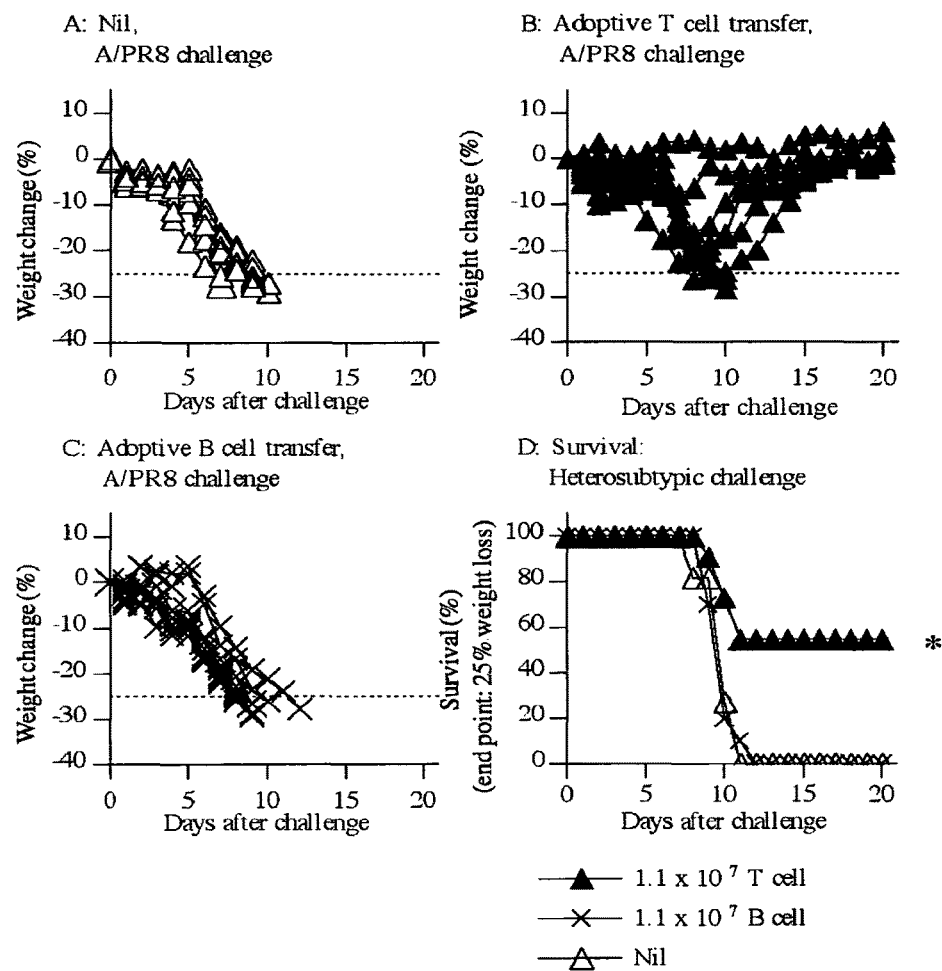
FIG. 14 provides a series of graphs showing that adoptively transferred T cells, but not B cells, protect mice against heterosubtypic challenge. (A; B & C)=weight loss; (D)=mortality; * P<0.05 vs. control nil group; Fisher's exact test.

Although these results show a role for B, CD4+ T and CD8+ T cells in the cross-protective immunity against influenza, defective primary immune responses in the knock-out mice may obscure the cross-protective potential of both humoral and cellular memory responses. As an alternative approach to assess the nature of the effector cells, we used an adoptive transfer model, with splenocytes from 3 week earlier intravenously γ-irradiated A/PC ($1\times10^8$ PFU equivalent) immunized mice as donor cells. Splenocytes were nylon wool-enriched T cells (82.8% T cells, 7.9% B cell) or B cells (84.2% B cells, 8.3% T cells) and intravenously transferred into naïve mice. Three hour post-transfer mice were challenged with 0.1×LD50 A/PR8 ($7\times10$ PFU). Mice were monitored daily for weight loss and mortality for 20 days. T cell recipients were partially protected against A/PR8 challenge (FIGS. 14A, B & D). In contrast, no protection was observed in B cell recipient mice, which developed disease symptoms similar to that of controls (unvaccinated with no lymphocyte transfer) following A/PR8 challenge (FIGS. 14A, C & D). These adoptive transfer studies further support a critical role for T cells, but not B cells, in cross protective immunity against A/PR8 challenges.

Figure 15:
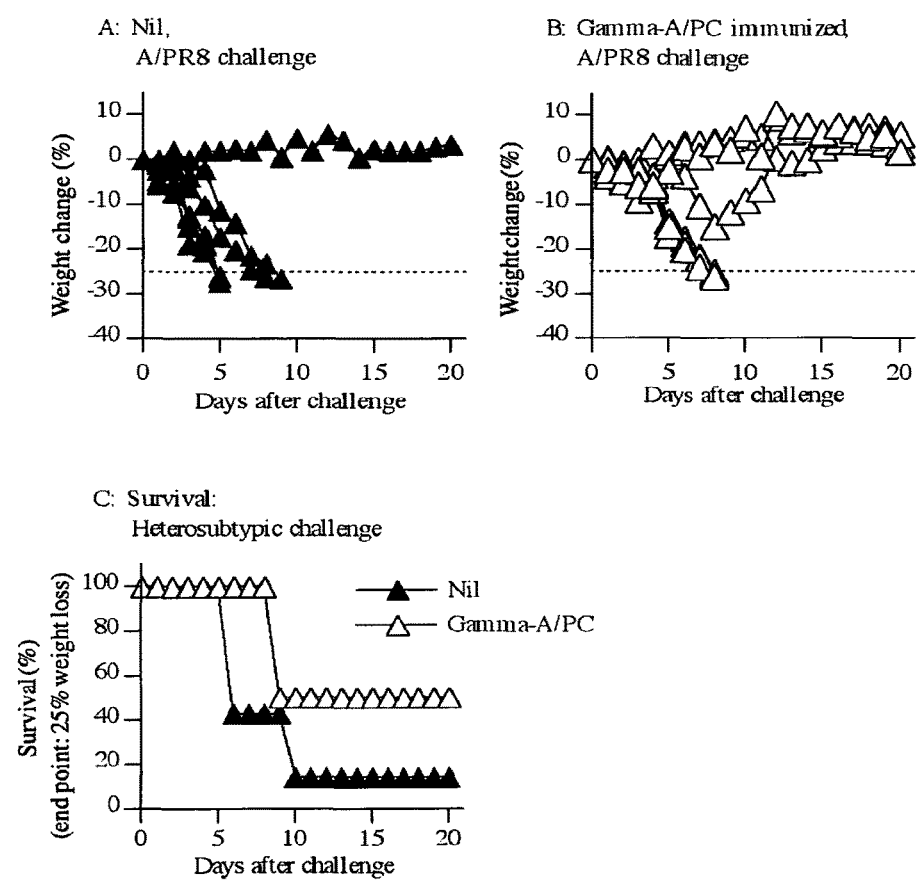
FIG. 15 provides a series of graphs showing a lack of heterosubtypic protection in perforin deficient mice. (A & B)=weight loss; (C)=mortality.

CD8+ T cells exert antiviral effects by either directly killing virus-infected cells or secreting cytokines such as IFN-γ and TNF. To delineate which effector function of T cells provides heterosubtypic immunity, prf$^{-/-}$ mice (which lack perforin-mediated lytic function) and IFN-IIR$^{-/-}$ mice (whose immune cells are unresponsive to IFN-γ) were utilised. Prf$^{-/-}$ mice were immunized intranasally with γ-irradiated A/PC ($3.2\times10^6$ PFU equivalent). 3 weeks post-immunization, naïve and immunized mice (9~10 mice per group) were challenged with the heterosubtypic strain A/PR8 ($7\times10^2$ PFU). Mice were monitored daily for weight loss and mortality for 20 days. Vaccination with γ-irradiated A/PC failed to confer significant cross-protection to prf$^{-/-}$ mice (FIGS. 15A, B & C). This strongly suggests that cross protection induced by γ-irradiated A/PC requires perforin-mediated lytic function, which is associated with CD8+ T and NK cells.

Figure 16:
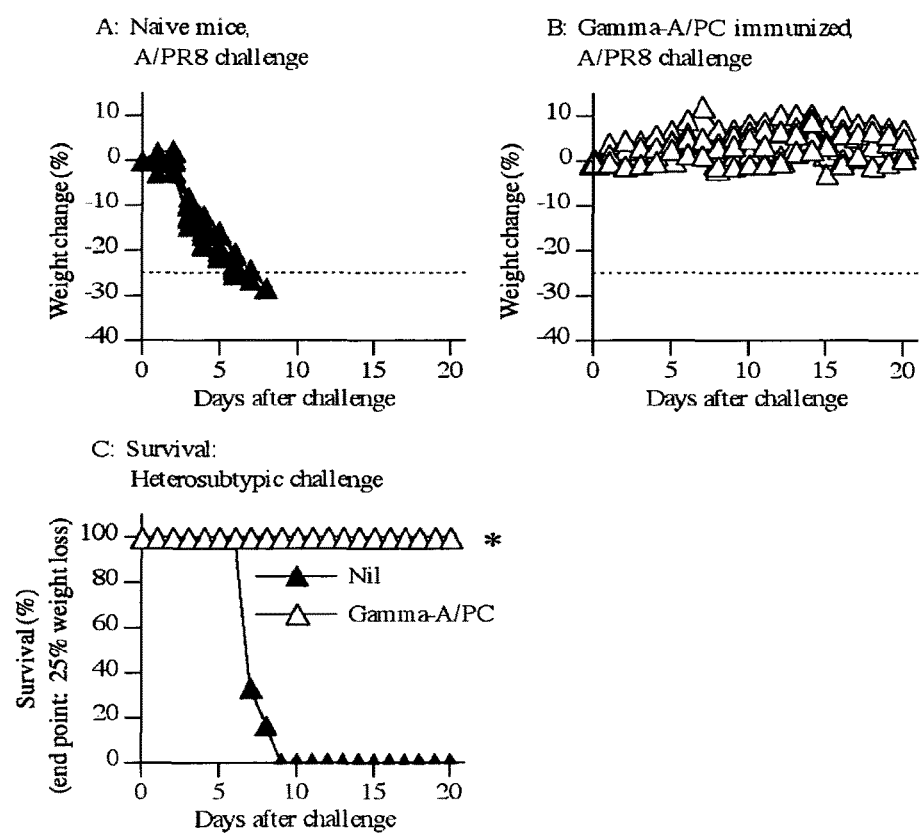
FIG. 16 provides a series of graphs showing heterosubtypic protection in Type II IFN receptor knock-out mice. (A, B)=weight loss; (C)=mortality; * P<0.05 vs. control nil group; Fisher's exact test.

In contrast, IFN-IIR$^{-/-}$ mice immunised with γ-irradiated A/PC (same conditions) were fully protected against a lethal challenge with A/PR8 (FIGS. 16A, B & C). Thus, IFN-γ function is dispensable for the induction of the cross-protective immunity.

Figure 17:
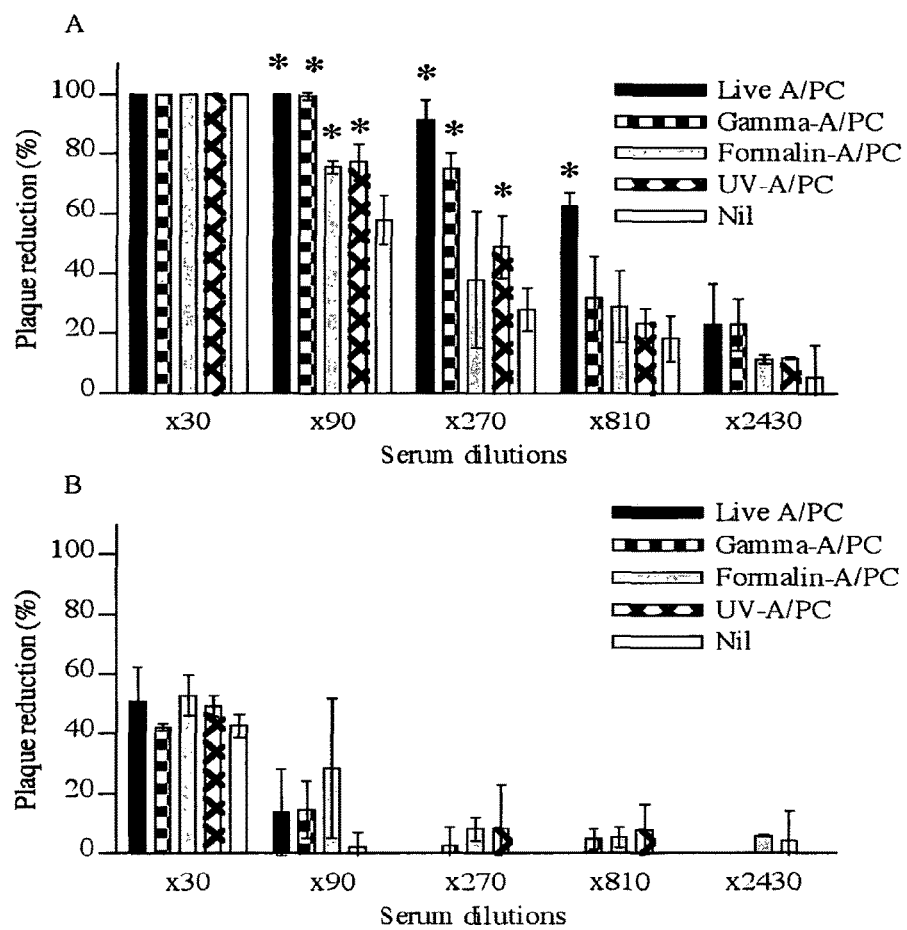
FIG. 17 provides two graphs showing an absence of cross-neutralizing activity in serum of immunized mice. (A)=viral neutralizing activities against A/PC (H3N2); (B)=viral neutralizing activities against A/PR8 (H1N1).

Absence of Cross-Neutralizing Activity in the Serum of γ-Irradiated A/PC Immunized Mice As noted in Example 3 above, immunisation with γ-irradiated (but not formalin- or UV-inactivated) influenza viruses induce cross-protective immunity. Hence, the cross-neutralizing activity of the immune sera induced by variously inactivated influenza formulations against homologous and heterosubtypic strains of influenza A viruses was tested. Viral neutralizing activities against A/PC (H3N2) or A/PR8 (H1N1) were determined by plaque reduction assays for sera collected 3 weeks after immunization with live, γ-irradiated, formalin or UV-inactivated A/PC. After heat inactivation of serum samples at 56° C. for 30 minutes, 190 μl of serially diluted (×10, ×30, ×90, ×270) sera were mixed with 10 μl virus suspension containing roughly $1\times10^2$ PFU. After 60 minutes incubation the virus/serum mixtures were added to six well plates for plaque assay. Immune sera collected from all vaccinated animals contained high levels of neutralizing activity against the homologous strain A/PC (H3N2) (FIG. 17A). The same immune sera, when tested against a heterosubtypic strain A/PR8 (H1N1), showed levels of neutralizing activity similar to that of naïve sera (FIG. 17B). These data demonstrate that immunization with any of the inactivated influenza virus preparations, including γ-irradiated influenza viruses, induces highly strain-specific neutralizing antibodies with limited, if any, cross neutralising activity.

Figure 18:
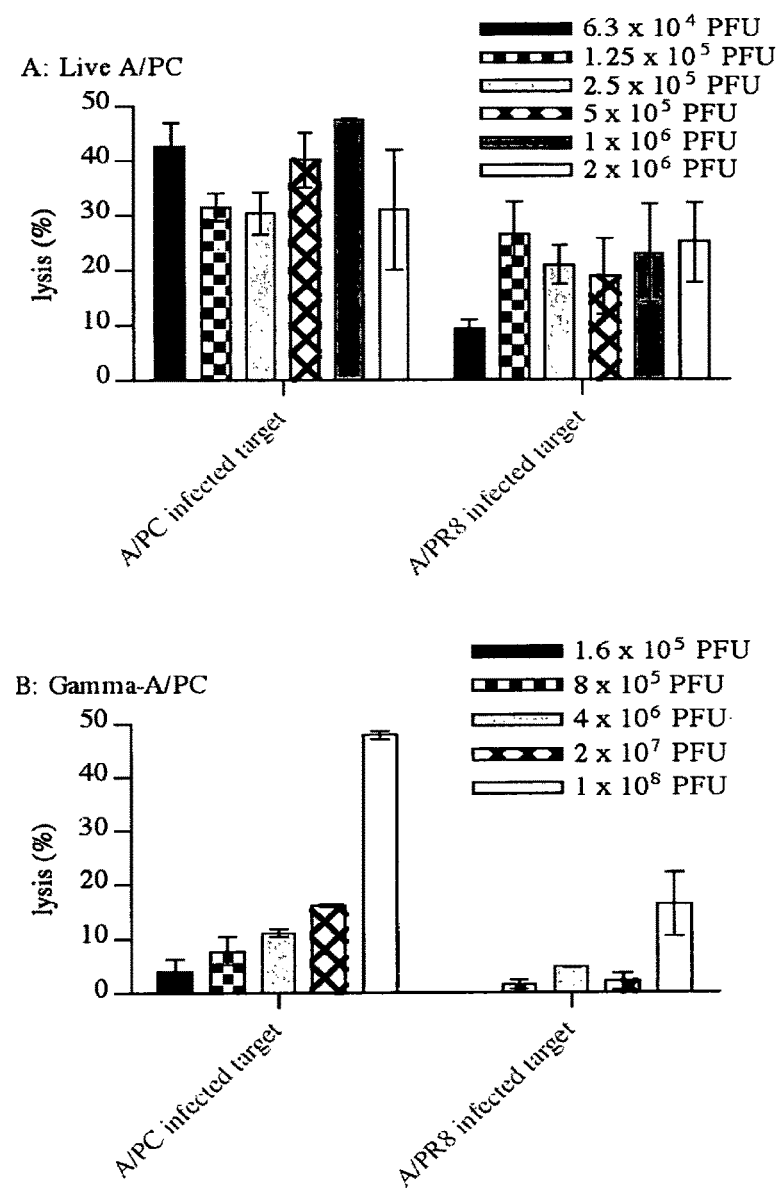
FIG. 18 provides two graphs showing dose dependence of primary Tc cell responses induced by γ-irradiated A/PC. (A, B)=splenocytes harvested 6 days post-immunization. Error bar represents the mean percent±S.D. Specific lysis values were interpolated from regression curve at effector:target ratio of 60:1.

The Induction and Magnitude of Cross-Reactive Tc Cell Response by γ-Irradiated A/PC is Dose-Dependent The absence of serum cross-neutralising activity between H3N2 and H1N1 influenza viruses, lack of cross-protective immunity in defined knock-out mice, and the results from adoptive transfer experiments indicate that cellular immunity plays a pivotal role in protecting mice against heterosubtypic challenges. To characterize the cytolytic function of T cells in vaccinated mice, mice were intravenously immunized with various doses of either live or γ-irradiated A/PC and their splenocytes tested for specific target cell killing 6 days post-immunization. Groups of two BALB/c mice were immunized intravenously with various doses of either live or γ-irradiated A/PC and splenocytes were harvested on day 6 post-immunization. Splenocytes were used as effector cells against mock treated or A/PC or A/PR8 infected P815 target cells. Live A/PC elicited strong Tc cell responses over a wide range of immunization doses (FIG. 18A). Immunization with a high dose ($10^8$ PFU equivalent) of γ-irradiated A/PC also elicited a strong Tc cell responses against both A/PC and A/PR8 infected targets (FIG. 18B). However, immunization with low doses ($1.6 \times 10^5$ PFU equivalent or less) did not induce statistically significant cross-reactive Tc cell responses. Thus, the magnitude of the Tc cell response by γ-irradiated A/PC correlates with immunization dose.

Induction of Memory. Tc Cells by γ-Irradiated A/PC

Figure 19:
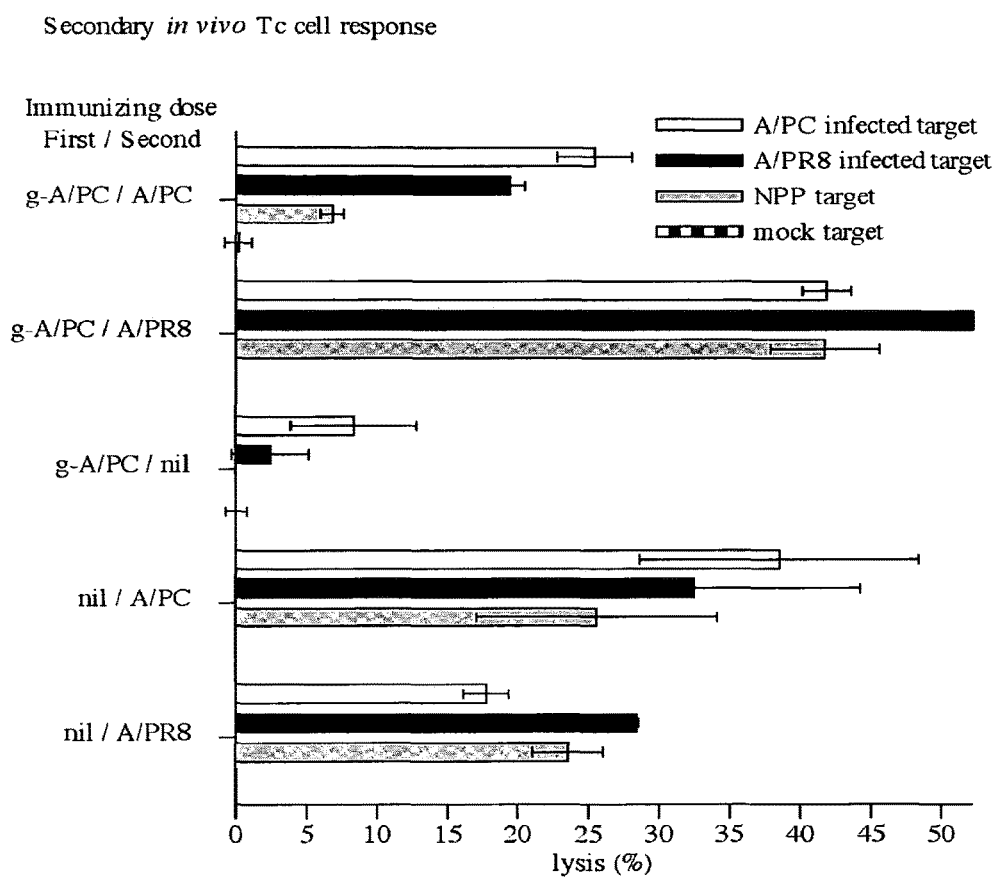
FIG. 19 is a graph showing secondary ex vivo Tc cell responses. Specific lysis values were interpolated from a regression curve at effector:target ratio of 40:1.

As noted in Example 3 above, immunization with γ-irradiated A/PC provides cross-protection for at least 3 months. Hence, the longevity of memory T cells that may account for the long lasting protection was investigated. Groups of two BALB/c mice were intravenously immunized once or twice with either live A/PC ($2 \times 10^6$ PFU), A/PR8 ($1 \times 10^7$ PFU) or γ-irradiated A/PC ($1 \times 10^8$ PFU equivalent). The secondary immunization was given 3 weeks after priming. Splenocytes were harvested 7 days after the second immunization and used as effector cells against mock, A/PC- or A/PR8 infected P815 target cells or labelled with $K_d$ restricted nucleoprotein derived peptide (NPP). The secondary immunization with live heterosubtypic strain A/PR8 induced a strong secondary Tc cell response (FIG. 19). In contrast, mice that received live homologous strain A/PC as a secondary immunization showed no increase in Tc cell potency (FIG. 19).

(iii) Discussion

As noted in the Examples above, γ-ray inactivated influenza A virus, especially when administered intranasally, confers robust protection against lethal homologous and heterosubtypic virus challenges, including the virulent avian H5N1 strain. These data demonstrate that cross-reactive cellular immunity mediated predominantly by Tc cells, and not humoral immunity, is the essential element responsible for the cross protective immunity induced by γ-irradiated influenza virus. This conclusion is based on several independent lines of evidence: 1) $\beta2M^{-/-}$ mice did not generate cross protective immune responses; 2) transfer of enriched T cells, but not of B cells or immune sera, from γ-inactivated influenza immune donor mice conferred cross reactive immunity to naïve recipients; and 3) cross-protective immunity induced by the preparation was dependent on the essential cytolytic effector molecule perforin.

The latter observation, together with the induction of cross-protective immunity induced in mice strongly suggests that cytolytic Tc cells provide protection through killing of virus-infected cells via their granule-exocytosis pathway of cytotoxicity, and not by CD8+ T cell IFN-γ-mediated virus control. Consistent with the above, immunization with γ-irradiated influenza virus can elicit similar T cell responses to that induced by live virus. This cross reactive T cell potential persists for at least 3 months and led to a stronger secondary Tc response upon in vivo re-immunization. This correlates with the observation that mice immunised with γ-irradiated influenza virus are well protected against heterosubtypic challenge for at least 3 months. However, the immunization with a homologous strain did not enhance the secondary Tc response. This observation suggests that the primary immunization elicited highly strain specific antibody responses which neutralized the secondary challenge with the homologous virus, thus preventing memory Tc cell activation.

Induction of cross-reactive Tc cell responses was highly dose dependent on γ-irradiated virus in contrast to replicative live virus. With Tc cells identified as the dominant factor in providing heterosubtypic protection, there was still some evidence of a contribution by B cells to this protective response, since $\mu MT^{-/-}$ mice also showed increased susceptibility to heterosubtypic challenge. The absence of cross-neutralizing antibody responses in serum as well as a lack of protective effect of transferred serum suggests that the contribution of B cells is independent of their principle soluble product, antibody. In certain circumstances, Naïve B cells are thought to be capable to restore immunity in $\mu MT^{-/-}$ mice against secondary infections in an antibody-independent manner. In addition, B cells may have a role in promoting effector Tc cell function. Hence, the possible role of cross protective antibodies cannot be neglected and mucosal cross-neutralizing antibodies may also be contributing to heterosubytpic immunity. The observed partial cross protection, although not statistically significant, in $\beta2M^{-/-}$ and $prf^{-/-}$ mice supports this notion. Moreover, passive immunity obtained by adoptive T cell transfer was only partially successful in protecting against a sublethal dose of virulent A/PR8. Thus, both antibodies as well as Tc cells may ultimately contribute to optimal cross-protection.

Example 5: Superiority of γ-Ray Inactivated-Influenza Vaccine Compared to UV-Inactivated and Formalin-Inactivated Influenza Vaccines (i) Materials and Methods Mice Nine- to ten-week-old female BALB/c mice were routinely used in these studies.

Viruses and Cells

P815 mastocytoma, Madin-Darby canine kidney (MDCK) and baby hamster kidney (BHK) cells were grown and maintained in EMEM plus 5% FCS at 37° C. in a humidified atmosphere with 5% $CO_2$. The influenza type A viruses, A/PR/8 [A/Puerto Rico/8/34 (H1N1)] and A/PC [A/Port Chalmers/1/73 (H3N2)] were grown in 10-day-old embryonated chicken eggs. Each egg was injected with 0.1 ml normal saline containing 1 hemagglutinin unit (HAU) of virus, incubated for 48 hours at 37° C., and held at 4° C. overnight. The allantoic fluids were then harvested, pooled and stored at −80° C. Titres were $10^7$ PFU/ml (A/PC) and $2\times10^8$ PFU/ml (A/PR8) using plaque assays on MDCK cells. Viruses were purified using chicken red blood cells for vaccine preparation as described in (Sheffield, et al. (1954), "*Purification of influenza virus by red-cell adsorption and elution*", British journal of experimental pathology, 35:214-222). Briefly, infectious allantoic fluid was incubated with red blood cells for 45 minutes at 4° C. allowing the hemagglutinin to bind red blood cells, and then centrifuged to remove the allantoic fluid supernatant. The pellets were suspended in normal saline, incubated for 1 hour at 37° C. to release the red blood cells from the virus and then centrifuged to remove the red blood cells and collect the virus in the supernatant. Purified A/PC stock titre was $5\times10^8$ PFU/ml.

Virus Inactivation

For formalin inactivation, the viruses were incubated with 0.2% formalin at 4° C. for a week. The formalin was then removed by pressured dialysis using normal saline for 24 hours at 4° C. The dialysis method was adapted from Current Protocols in Immunology (see Andrew et al., (2001), "*Dialysis and concentration of protein solutions*", in *Current protocols in immunology*, Coligan et al. (eds), Appendix 3: Appendix 3H). For UV inactivation, the viruses were placed in 60-mm petri dishes with a fluid depth of 10 mm. The virus was exposed to 4000 ergs per cm$^2$ for 45 minutes at 4° C. For γ-ray inactivation, influenza viruses received a dose of 10 kGy from a $^{60}$Co source (Australian Nuclear Science and Technology Organization—ANSTO). The virus stocks were kept frozen on dry ice during γ-irradiation. Loss of viral infectivity was confirmed by titration of inactivated virus preparations in eggs. The HAU titres of inactivated virus stock were determined to be 7.29×10$^4$ HAU/ml for γ-A/PC, 2.43×10$^4$ HAU/ml for formalin- and UV-A/PC.

Freeze-Drying of γ-Ray Inactivated-Influenza

For freeze-drying, one vial containing 0.5 ml of γ-ray inactivated A/PC was placed in a Manifold Freeze-Dryer (FTS SYSTEMS, Dura-Dry™ MP).

Hemagglutination Assay

Live and inactivated virus preparations were serially diluted in a 100 µl volume on 96-well U-bottom microtiter plate. 0.5% chicken red blood cell suspensions were added to all wells and plates were incubated for 30 minutes on ice. This method was adapted from Current Protocols in Microbiology (see Szretter et al. (2006), "*Influenza: propagation, quantification, and storage*", in *Current Protocols in Microbiology*, Coico et al. (eds), Chapter 15: Unit 15G 11).

Protection Experiment

BALB/c mice were bred under specific pathogen-free conditions. 10-14-week-old females were used. Mice were immunized intranasally with inactivated virus preparations (3.2×10$^6$ PFU equivalent) or trivalent inactivated subunit influenza vaccine (CSL fluvax vaccine; A/Solomon Islands/3/2006 H1N1, A/Brisbane/10/2007 H3N2, B/Florida/4/2006; 3 mg hemagglutinin). The formalin inactivated A/PC vaccinated mice were re-immunized once or twice 2 and 3 weeks later. For lethal challenge, at 1-3 weeks post-immunization, mice were infected intranasally with 50% mouse lethal dose (MLD50). MLD50 was determined to be 7×10$^2$ PFU and 3.2×10$^5$ PFU for A/PR8 and A/PC, respectively, in preliminary experiments. For analysis of lung virus titers, 3 mice were euthanized on day 3 and 6 post-challenge. The remaining animals were monitored for body weight and mortality until day 20 post-challenge.

Plaque Assay

The lung tissue samples were collected 3 and 6 days after intranasal challenge. After removal, whole lungs were homogenized in normal saline. Homogenates were centrifuged at 1500 rpm for 5 minutes. Supernatants were collected and were stored at −20° C. Serial dilutions of the samples were inoculated on MDCK cells cultured on 6-well tissue culture plates. After 1 hour adsorption, the cells were overlaid with EMEM medium containing 1.8% Bacto-Agar. After incubation for 2-3 days, cell monolayers were stained with 2.5% crystal violet solution and the plaques were enumerated.

Lung-Histology

Lung tissue samples were fixed for a minimum of 24 hours in 10% neutral buffered formaldehyde. 10 µm sections were stained with Haemtoxilin-Eosin and evaluated by light microscopy.

Cytotoxic T Lymphocyte (Tc Cell) Assay

Influenza-specific Tc cells were generated by intravenously injecting BALB/c mice with either live A/PC or inactivated, 10$^8$ PFU equivalent, A/PC (γ-irradiated, formalin-, or UV-inactivated). Spleens were harvested at 7 days post immunization and red blood cell-depleted cell suspensions were prepared for use as effector cells. Target cells were prepared by infecting P815 cells at a multiplicity of infection (m.o.i) of 1 for live A/PC and 10 for inactivated A/PC, followed by 1 hour incubation in medium containing 100~200 µCi of $^{51}$Cr. After washing, target cells were mixed with effector cells at different ratios in an 8 hour chromium release assay. The level of radioactivity in the supernatant was measured in a gamma counter. Specific lysis is given as mean percent lysis of triplicate wells and values were calculated using the formula: (experimental cpm−spontaneous cpm)/(maximal release cpm−spontaneous cpm)×100.

(ii) Results

The Effect of Virus Inactivation on Hemagglutination Activity

Hemagglutination activity after virus inactivation provides one indicator as to the denaturing effect of the sterilization treatment. Purified influenza stock was aliquoted into batches and treated with either formalin, UV or γ-irradiation. Following complete inactivation of infectivity verified by the absence of virus growth in embryonated eggs, the hemagglutination activity of live and inactivated viruses was compared (Table 7).

TABLE 7

| Hemagglutination activity of inactivated influenza virus A/PC preparations. | | |
|---|---|---|
| Strain | Method of inactivation | HAU/ml |
| A/PC | Original live purified stock | 2.2 × 10$^5$ |
| | Gamma-ray inactivation | 7.3 × 10$^4$ |
| | Formalin-inactivation | 2.4 × 10$^4$ |
| | UV-inactivation | 2.4 × 10$^4$ |

Hemagglutination activity was reduced by 3-fold for γ-irradiated viruses, whereas formalin and UV inactivation resulted in 9-fold reduced hemagglutination titres. These results provide evidence that, of these three virus sterilization methods, γ-irradiation denatures viral protein structure least.

Figure 20:
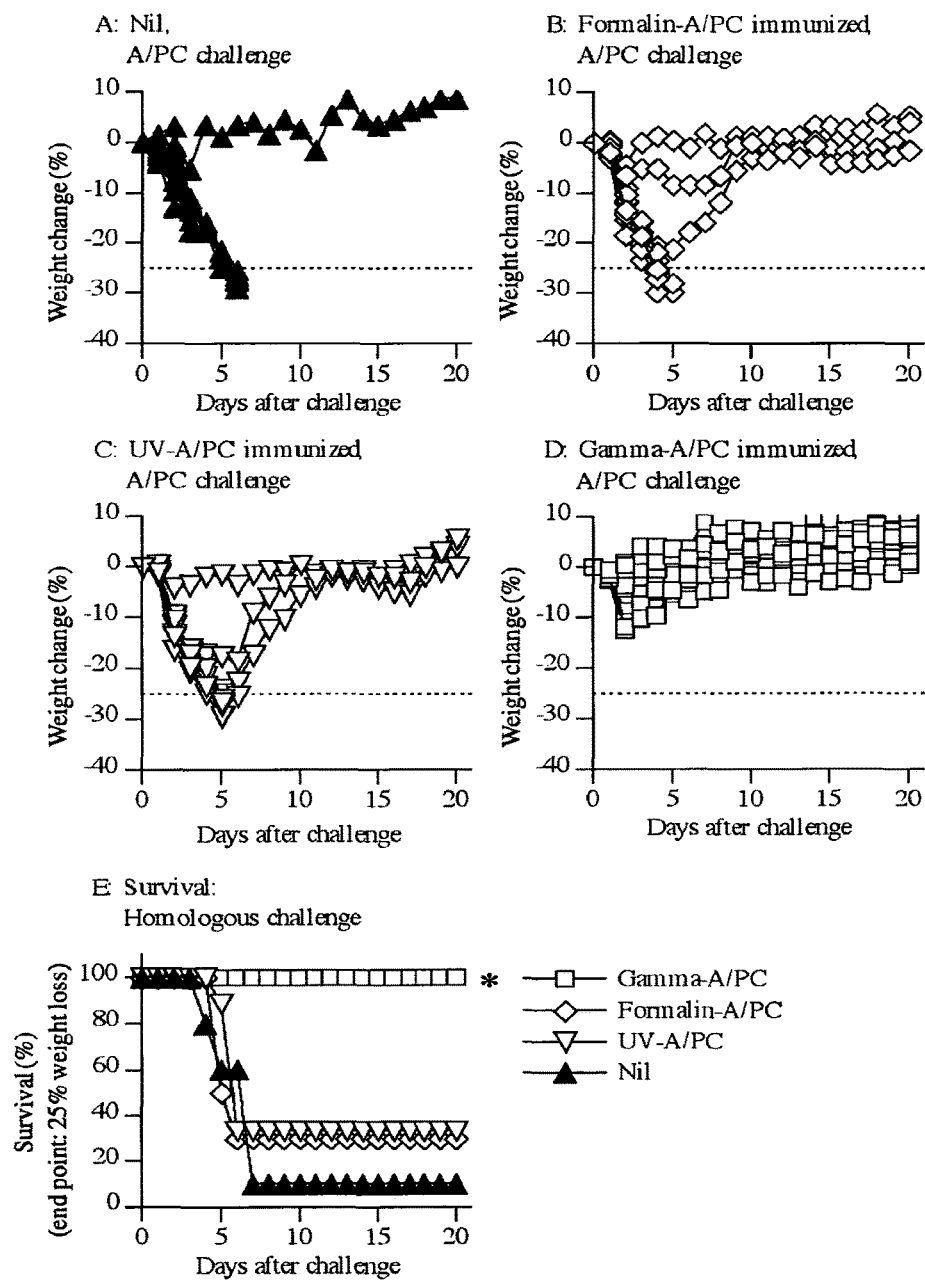
FIG. 20 provides a series of graphs showing gamma-irradiated influenza virus A/PC protects mice against both homologous and heterosubtypic challenge. (A, F)=mock treated; (B, G)=intranasally immunized with formalin inactivated A/PC; (C, H) intranasally immunized with UV inactivated A/PC; (D, I)=intranasally immunized with γ-ray inactivated A/PC; (E, J)=survival after 20 days; * P<0.05 vs. control naïve group; Fisher's exact test.
Figure 20:
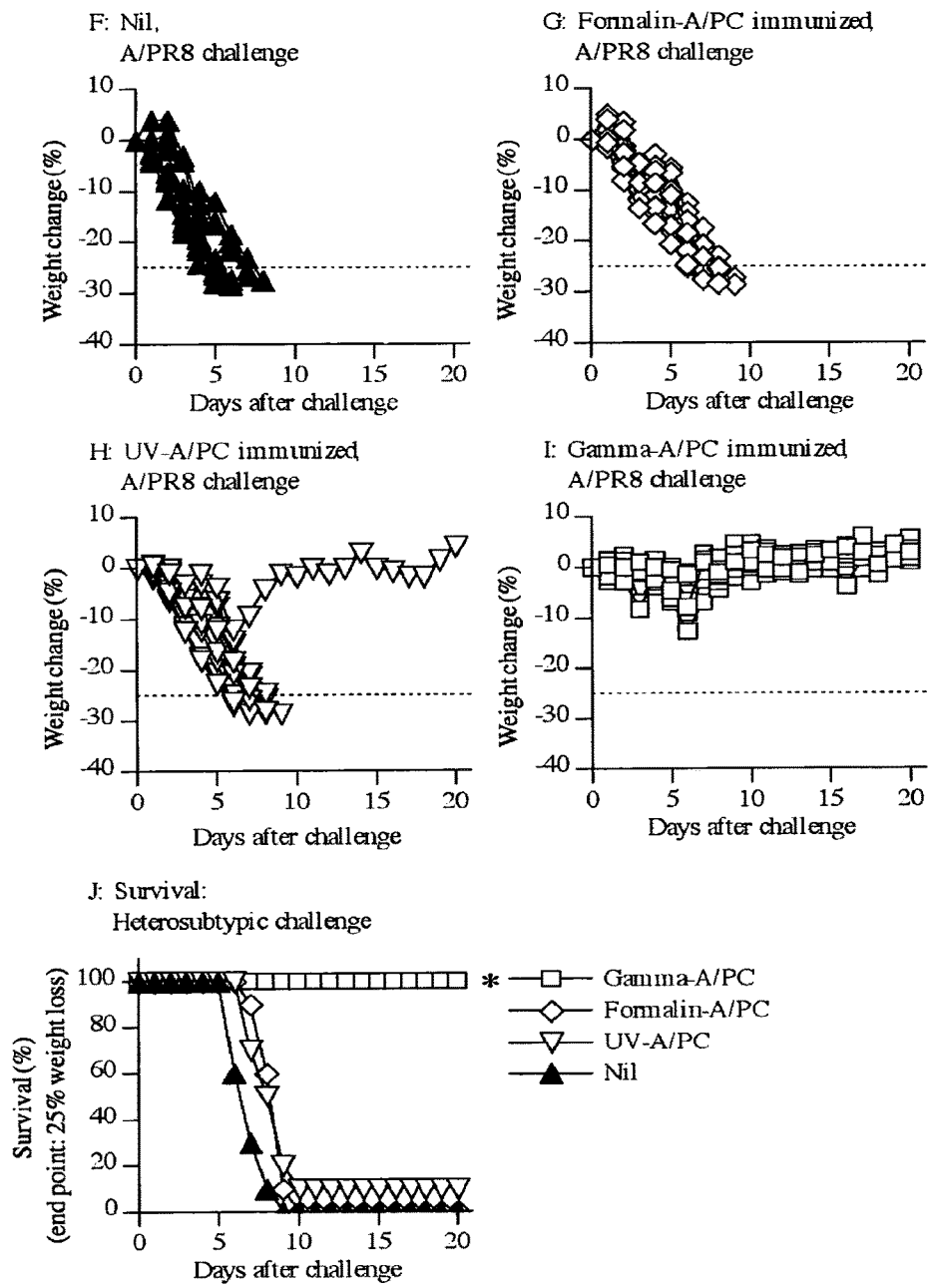

Gamma-Irradiated, but not Formalin or UV-Inactivated, Virus Preparations Induce Heterosubtypic Immunity The protective efficacy of γ-irradiated, formalin-, or UV inactivated influenza virus preparations against homo- and heterosubtypic live virus challenges was compared. Groups of 9-10 BALB/c mice were mock treated or immunized intranasally either with formalin-, UV- or γ-ray inactivated A/PC (3.2×10$^6$ PFU equivalent) and at week 3 after the immunization, naïve and immunized mice (9~10 mice per group) were intranasally infected with A/PC (MLD50; 3.2× 10$^5$ PFU) or A/PR8 (MLD50; 7.0×10$^2$ PFU). Survival of infected mice was monitored daily for 20 days. As shown in FIGS. 20 A, E, F & J, intranasal infection of naïve mice with A/PC or A/PR8 caused a rapid weight loss with 90-100% mortality (based on 25% weight loss as an end point). Mice immunized with either formalin inactivated A/PC (FIGS. 20B & E) or UV-inactivated A/PC (FIGS. 20C & E) also developed significant weight loss and resulted in ~70% mortality when challenged with live homologous virus. When similarly vaccinated mice were challenged with the heterosubtypic strain A/PR8, the animals lost substantial body weight with 90~100% mortality (FIGS. 20G, H, & J). In both cases, homologous and heterosubtypic challenge, the induced protection was considered inadequate to be used as a vaccine (P-value>0.05, Fisher's exact test). In contrast, mice immunized with a single dose of γ-inactivated A/PC were not only protected against homologous virus challenge, but also against heterosubtypic challenge, with mice losing only 5% of their body weight on average (FIGS. 20D, E, I & J). Hence, γ-irradiated influenza virus proved by far to be the most effective vaccine preparation to induce protective immunity against homo- and heterosubtypic influenza virus challenges (P<0.05).

Figure 21:
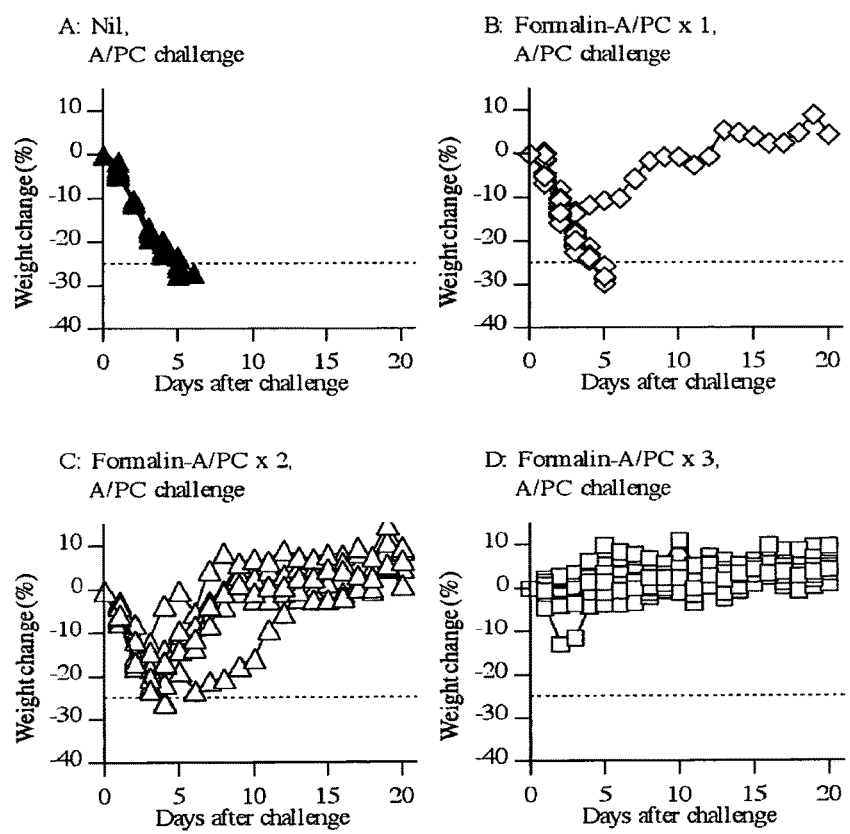
FIG. 21 provides a series of graphs showing that multiple immunizations of formalin-inactivated influenza virus A/PC are required to induce homologous protection. (A, F)=mock treated; (B)=immunized once with formalin-inactivated A/PC; (C)=immunized twice with formalin-inactivated A/PC; (D, G)=immunized three times with formalin-inactivated A/PC; (E, H)=survival after 20 days; * P<0.05 vs. control naïve group; Fisher's exact test.
Figure 21:
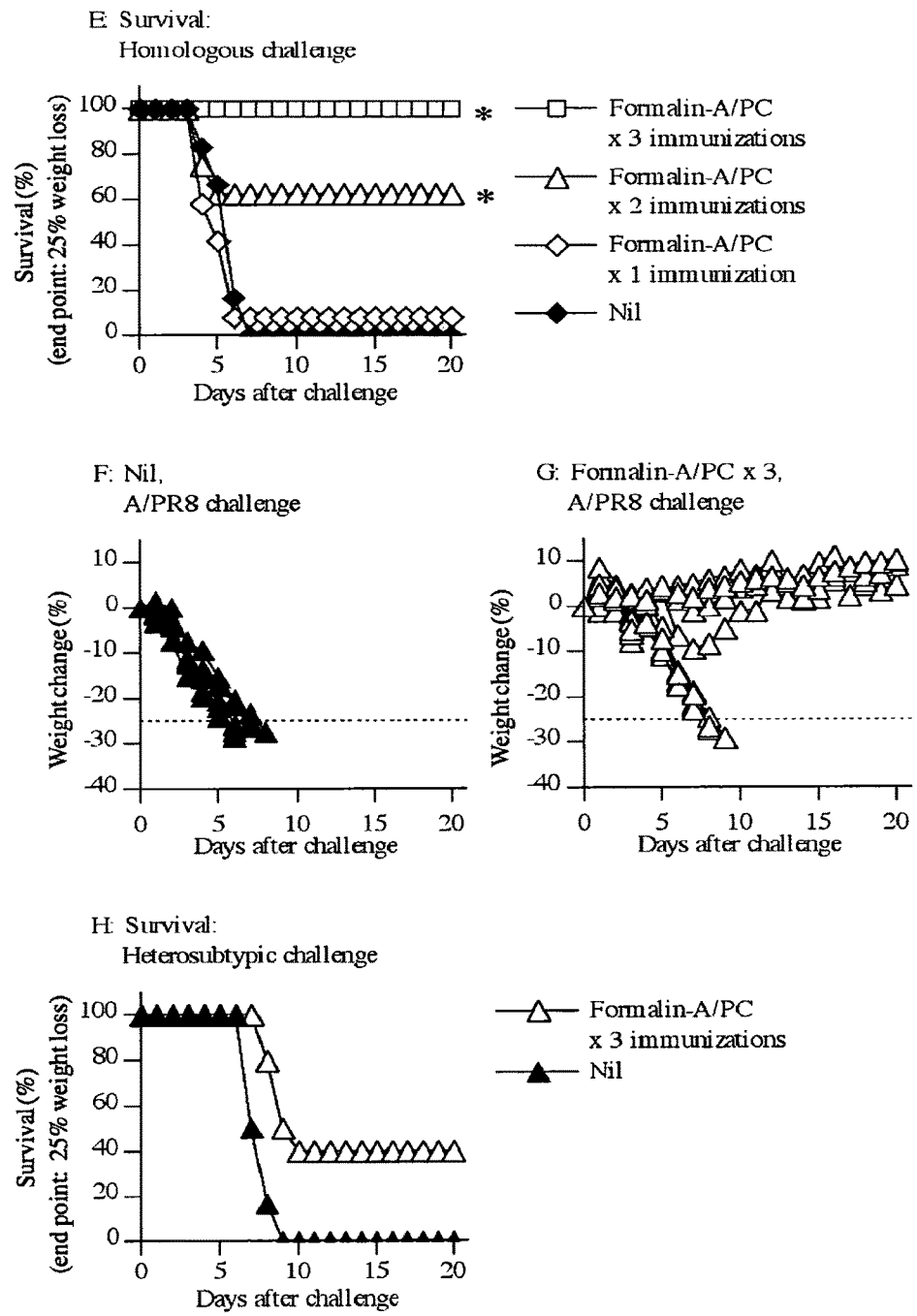

Can Multiple Doses of Formalin-Inactivated Influenza Virus Preparation Enhance the Protective Effect?

γ-ray inactivated A/PC was clearly more effective after only one intranasal dose than multiple intranasal administrations of formalin-inactivated preparations. It was then determined whether the weak protective efficacy of formalin-inactivated A/PC could be improved by testing different immunization schedules. Groups of 9-10 BALB/c mice were mock treated or immunized either once, twice or three times with formalin-inactivated A/PC ($9.6 \times 10^6$ PFU equivalent or HAU dose equivalent to that of γ-ray inactivated A/PC; 2300 HAU). Mock treated or single dose immunized mice were challenged with A/PC (MLD50; $3.2 \times 10^5$ PFU) at three weeks post immunization. Double or triple dose immunized mice were intranasally infected with A/PC (MLD50; $3.2 \times 10^5$ PFU) or A/PR8 (MLD50; $7 \times 10^2$ PFU) one week after the final immunization. Survival of infected mice were monitored daily for 20 days. The group of mice that received a single immunization had no improved survival rate compared to that of unvaccinated mice (FIGS. 21A, B & E). In contrast, double immunization improved the survival rate to 60% (P<0.05) although the majority of mice still showed a significant loss in bodyweight, indicating that they experienced severe illness (FIGS. 21C & E). The mice receiving triple immunization with formalin-inactivated A/PC showed complete protection with no mortality and little weight loss (FIGS. 21D & E). Triple immunization conferred partial protection from heterosubtypic challenge (P<0.05) (FIGS. 21F, G & H). Thus, formalin-inactivated A/PC requires more doses and fails to elicit the cross-protection suggesting that the induced immunity is not only quantitatively, but also qualitatively, substantially inferior to that induced by γ-ray inactivated A/PC.

Trivalent Flu Vaccine is Ineffective Against Drifted Strains

Figure 22:
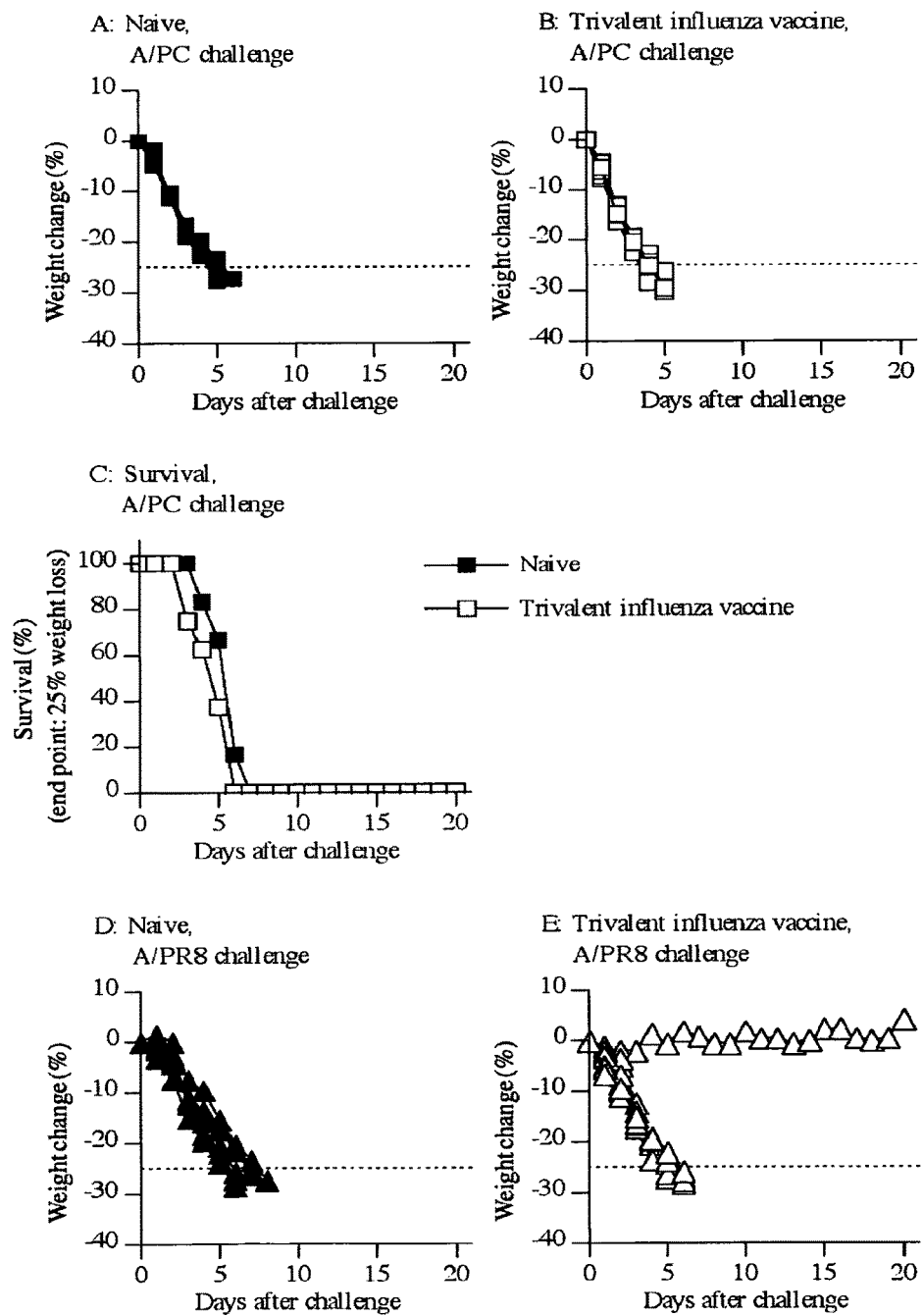
FIG. 22 provides a series of graphs showing that a trivalent influenza vaccine failed to provide protection against drifted strains. (A, D)=naïve (B, E)=immunized; (C, F)=survival after 20 days.
Figure 22:
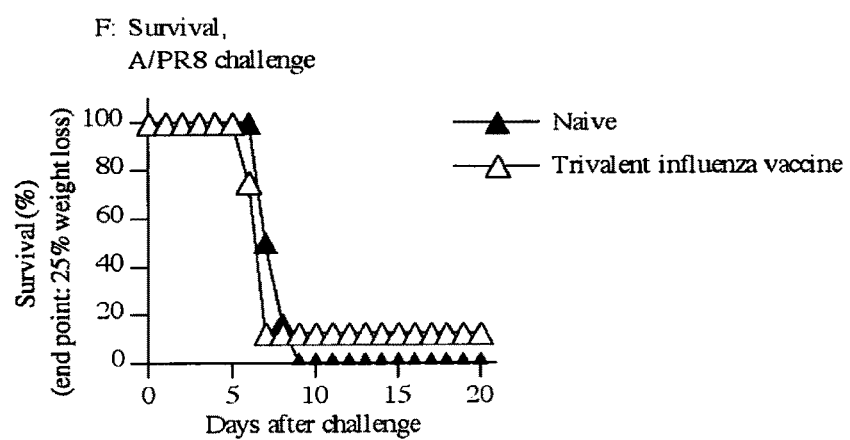

For a direct comparison, the protective efficacy of a commercially available trivalent influenza vaccine was tested in the experimental approach described herein. Mice were immunized once intranasally with trivalent influenza vaccine (CSL fluvax vaccine; A/Solomon Islands/3/2006 H1N1, A/Brisbane/10/2007 H3N2, B/Florida/4/2006; 3 μg hemagglutinin) and at 3 week post immunization, naïve and immunized mice were intranasally challenged with either A/PC ($3.2 \times 10^5$ PFU/mouse) or A/PR8 ($7 \times 10^2$ PFU). Survival of infected mice was monitored daily for 20 days. As shown in FIG. 22, single intranasal immunization of mice conferred no statistically significant protection (P>0.05) against both A/PC ($3.2 \times 10^5$ PFU) (FIGS. 22A, B & C) and A/PR8 strain ($7 \times 10^2$ PFU) (FIGS. 22D, E & F). This clearly shows that the current influenza vaccine does not confer appreciable cross-protection after a single dose, even against strains within the same subtype.

Figure 23:
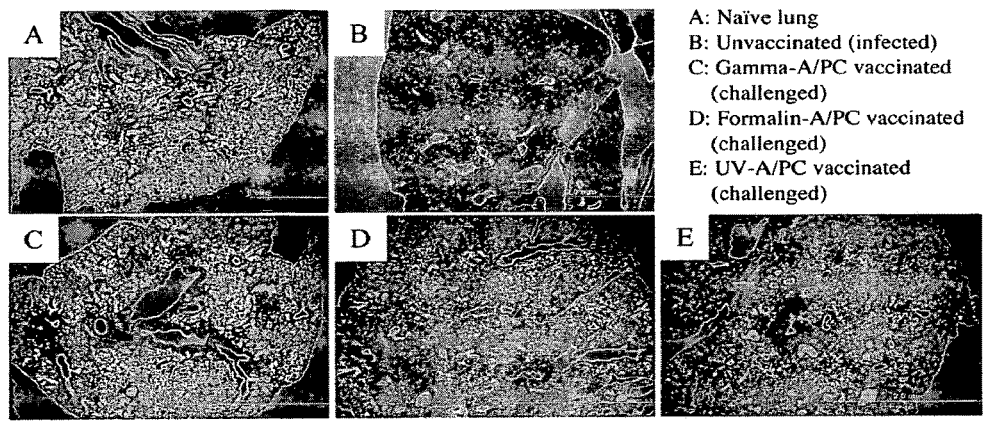
FIG. 23 provides representative photomicrographs of immunohistochemically stained lung tissue following homologous challenge. (A)=naïve lung; (B)=unvaccinated (infected); (C)=gamma-A/PC vaccinated (challenged); (D)=formalin-A/PC vaccinated (challenged); E=UV-A/PC vaccinated (challenged).

Minimal Influenza Infection-Induced Lung Inflammation after Vaccination with γ-Ray Inactivated A/PC Three weeks following vaccination ($3.2 \times 10^6$ PFU equivalent) with γ-irradiated, formalin- and UV-A/PC, mice were challenged with either A/PC (homologous) or A/PR8 strain (heterosubtypic) of live virus. Lungs of surviving mice were harvested 21 days post-challenge and lungs processed for histology. The lung samples displayed remarkable histological differences, corresponding to the type of immunization given. As shown in FIG. 23, limited inflammatory responses were seen when vaccinated mice were challenged with the homologous virus A/PC. Lung sections from all three vaccinated groups (γ-irradiated, formalin or UV-inactivated A/PC) were comparable in their appearance to that of naïve tissue (FIGS. 23 A, C, D, & E). In contrast, lung tissues from unvaccinated, A/PC-challenged, mice showed extensive inflammatory responses (FIG. 23B). The heterosubtypic challenge resulted in clear differences among the various vaccinated groups.

Figure 24:
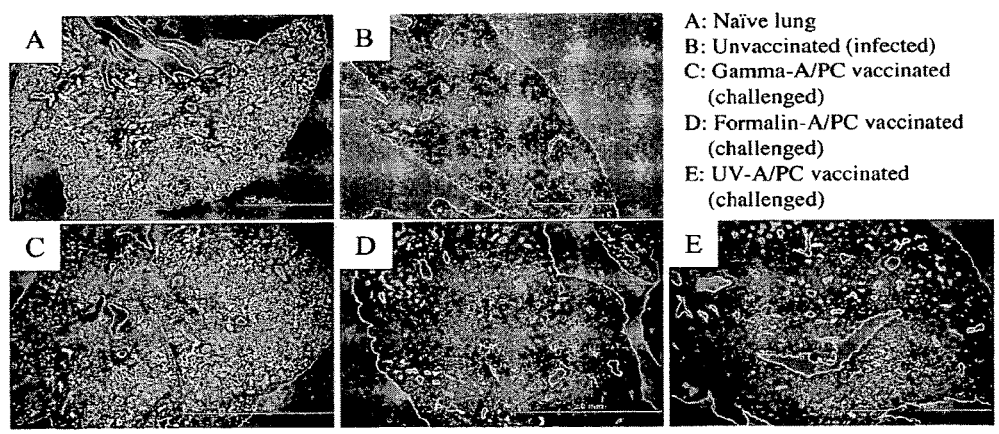
FIG. 24 provides representative photomicrographs of immunohistochemically stained lung tissue following heterosubtypic challenge. (A)=naïve lung; (B)=unvaccinated (infected); (C)=gamma-A/PC vaccinated (challenged); (D)=formalin-A/PC vaccinated (challenged); E=UV-A/PC vaccinated (challenged).

The inflammatory responses in formalin- and UV-A/PC vaccinated animals were strong and similar to that of the unvaccinated animals following A/PR8 challenge 21 days post-vaccination (FIGS. 24B, D & E). In contrast, lung inflammation in γ-irradiated A/PC vaccinated mice was limited following heterosubtypic challenge with A/PR8 (FIG. 24C). Although these lungs exhibited localised inflammation with weak lymphocyte infiltration, the overall condition was similar to that of naïve lungs (FIG. 24A).

Figure 25:
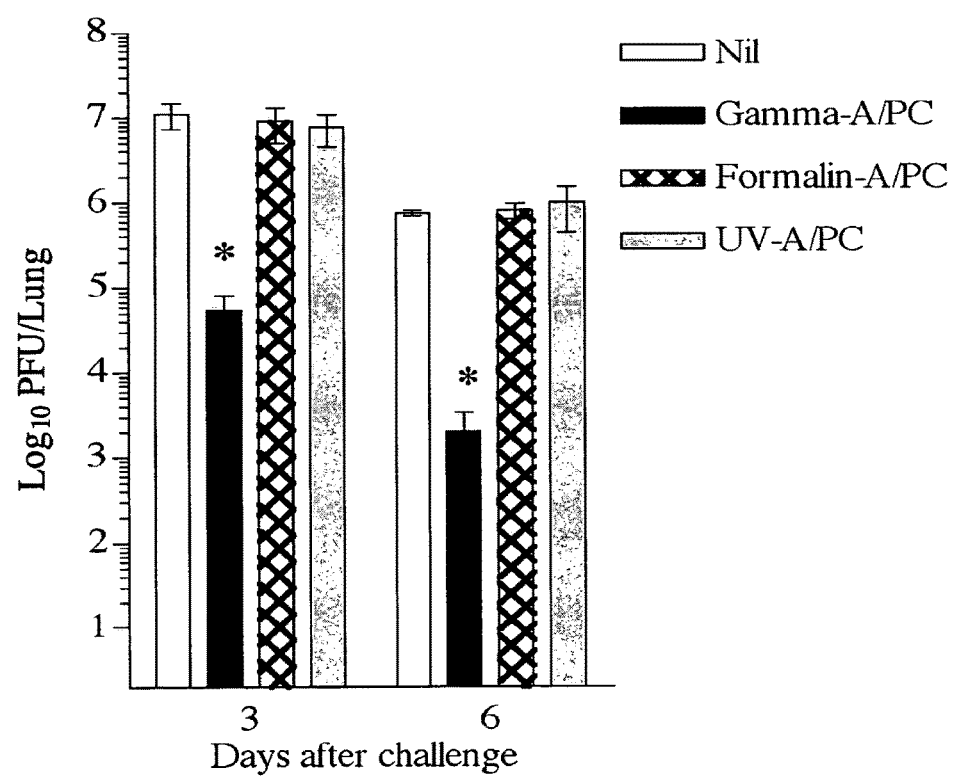
FIG. 25 is a graph illustrating that various inactivated virus preparations do not prevent influenza infection but immunization with γ-ray inactivated A/PC leads to early viral clearance.

Gamma-Ray Inactivated a/PC Vaccine does not Prevent Infection but Facilitates Viral Clearance The effect of vaccination on pulmonary viral load at days 3 and 6 after heterosubtypic challenge with A/PR8 was evaluated. BALB/c mice were intranasally immunized either with γ-irradiated, formalin or UV inactivated A/PC ($3.2 \times 10^6$ PFU equivalent) and at week 3-post immunization, naïve and immunized mice were intranasally challenged with A/PR8 virus (MLD50). On day 3 and 6 post infection, three mice per group were sacrificed and the viral titres in lungs determined by the plaque assay using MDCK cells as described above. High virus titres reaching $10^7$ and $10^6$ PFU/lung for days 3 and 6 post-infection, respectively, were detected in unvaccinated mice (FIG. 25). Virus titres in the lungs of formalin- and UV-inactivated A/PC immunized mice were comparable to those detected in unvaccinated control mice. In contrast, the γ-irradiated A/PC vaccinated group showed a >100-fold reduction of A/PR8 lung virus titres both at days 3 and 6 post-challenge (P<0.05 using Student's T test) compared to that seen in unvaccinated control mice.

Figure 26:
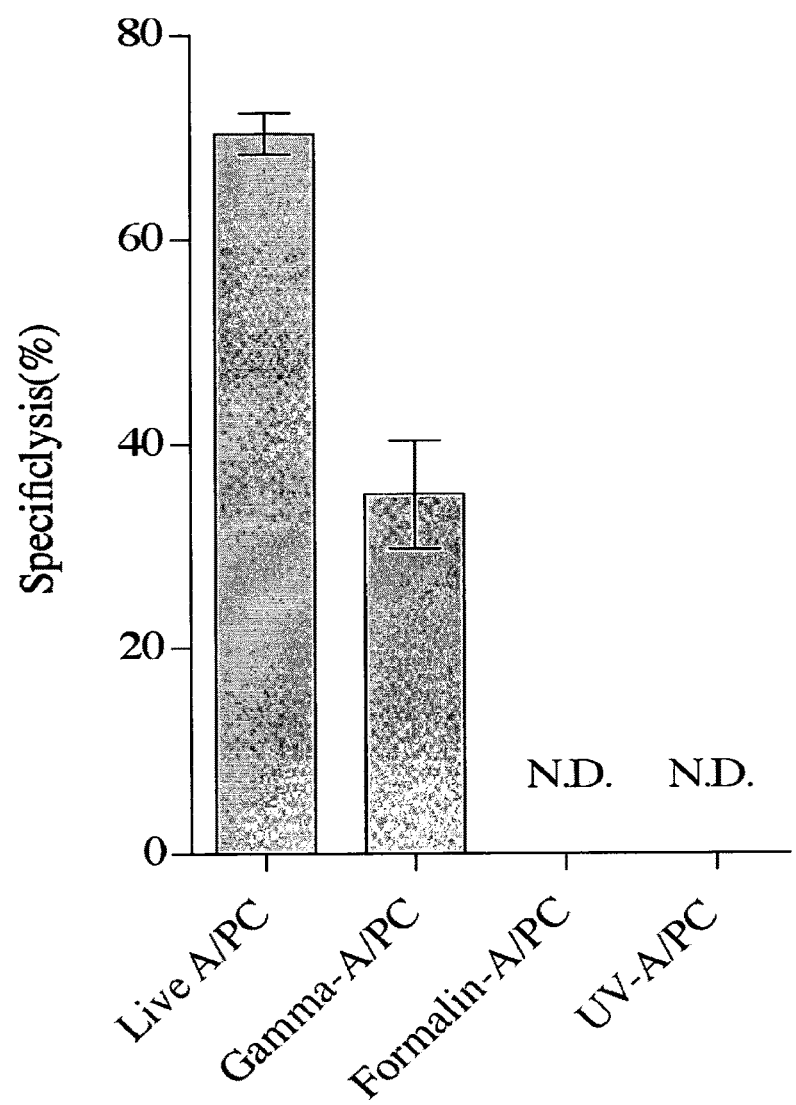
FIG. 26 is a graph showing a comparison of Tc cell responses induced by live and inactivated A/PC. Mean values±SD of two mice per group are shown. Specific lysis values were interpolated from regression curves at effector: target ratio of 50:1. N.D.: not detected.

Gamma-Irradiated, but not Formalin- or UV-Inactivated Virus Retains Tc Cell Immunogenicity The ability to generate influenza-immune cytotoxic T (Tc) cell responses by live A/PC and inactivated A/PC (γ-ray, formalin-, and UV) was compared. BALB/c mice were intravenously immunized with live, γ-irradiated, formalin-, or UV-inactivated A/PC. Splenocytes were harvested 7 days post immunization and were used as effector cells against A/PC infected P815 target cells. The peak of the Tc cell response following live virus infection was detected at day 7 post immunization (data not shown). On day 7 after intravenous immunization two mice from each group were assessed. Effector splenocytes harvested from mice immunized with live ($10^7$ PFU) or γ-ray inactivated A/PC ($10^8$ PFU equivalent) lysed A/PC infected target cells, whereas effector cells from formalin- or UV-inactivated A/PC immunized mice did not (FIG. 26).

Intranasal Immunization with γ-Ray Inactivated a/PC Confers Protection Against High Dose Heterosubtypic Challenges.

Figure 27:
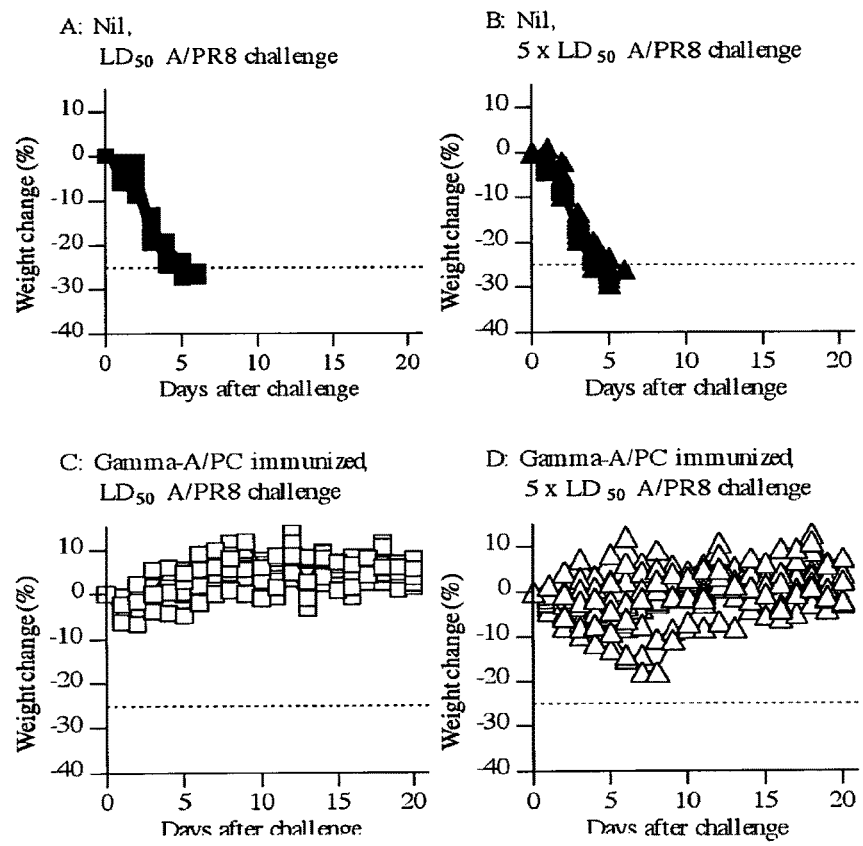
FIG. 27 provides a series of graphs illustrating that intranasal immunization with γ-irradiated A/PC provides protection against high-dose A/PR8 lethal challenge. (A, C)=mice challenged with LD50 A/PR8; (B, D)=mice challenged with 5×LD50 A/PR8; (E)=mice challenged with 50×LD50 A/PR. (F)=survival and weight loss after 20 days. * P<0.05 vs. control naïve group; Fisher's exact test.
Figure 27:
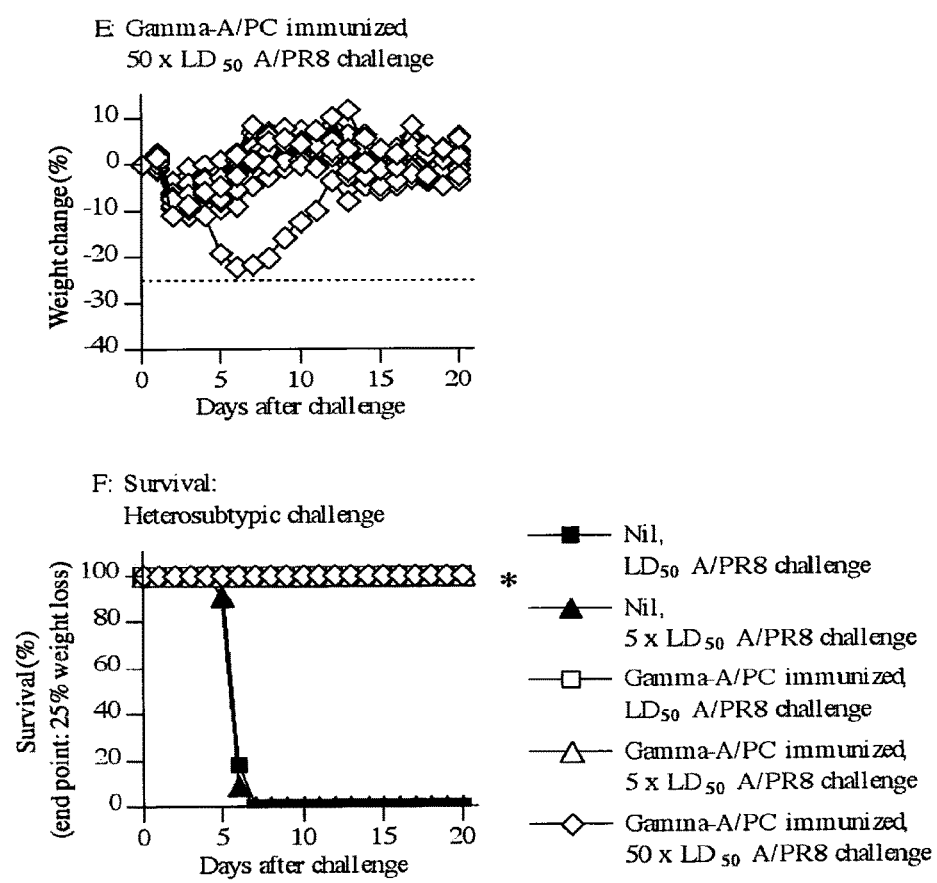

Given the excellent protective capacity of γ-irradiated A/PC to protect mice from heterosubtypic challenge, the limit of protection was investigated by challenging with increased influenza virus doses (FIG. 27). Groups of 9-10 BALB/c mice were mock treated or immunized intranasally with γ-ray inactivated A/PC ($3.2 \times 10^6$ PFU/ml equivalent)

and at 3 weeks post immunization mice were intranasally challenged with either LD50 A/PR8, 5×LD50 A/PR8, or 50×LD50A/PR8. Survival and weight loss of infected mice was monitored for 20 days. Immunized mice receiving heterosubtypic challenge of 1×LD50 all survived and there was little or no weight loss (FIGS. 27C & F). Immunized mice given a challenge dose of 5×LD50 initially lost weight during the first 7 days post-challenge, but not significantly, and all fully recovered (FIGS. 27D & F). The mice receiving 50×LD50 lost on average 8% of body weight but here, too, all mice fully recovered (FIGS. 27E & F). Naïve mice receiving 1×LD50 or 5×LD50 progressively lost weight and failed to survive the challenge (FIGS. 27A, B & F).

Figure 28:
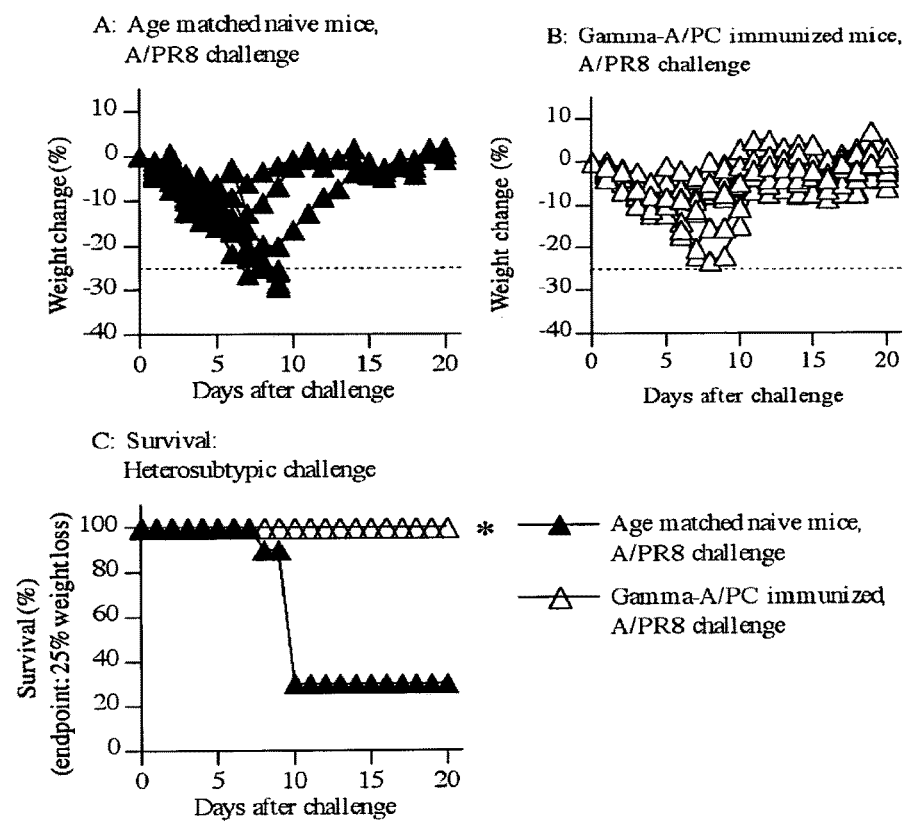
FIG. 28 provides a series of graphs illustrating that heterosubtypic protective properties of γ-irradiated A/PC are maintained after a dry freezing process. (A)=mock treated; (B)=challenged with heterosubtypic strain A/PR8; (C)=survival and weight loss after 20 days. * P<0.05 vs. control naïve group; Fisher's exact test.

Long-Lived Heterosubtypic Protection Conferred by γ-Ray Inactivated Preparations A critical requirement for an effective influenza vaccine is the induction of persistent heterosubtypic immunity. Groups of 9-10 BALB/c mice were either mock treated or immunized intranasally with γ-ray inactivated A/PC ($3.2 \times 10^6$ PFU equivalent) and at 3 months post immunization mice were intranasally challenged with MLD50 A/PR8 ($7 \times 10^2$ PFU). Survival and weight loss of infected mice was monitored for 20 days. The vaccinated mice challenged with 1×LD50 A/PR8 lost on average only up to 10% body weight and fully recovered (FIGS. 28B & C). In contrast, the majority of challenged naïve mice lost substantial weight, reaching an end point of 25% total body weight loss at around 7 days post challenge (FIGS. 28A & C).

Freeze-Drying does not Destroy the Immunogenicity of γ-Ray Inactivated-A/PC

Figure 29:
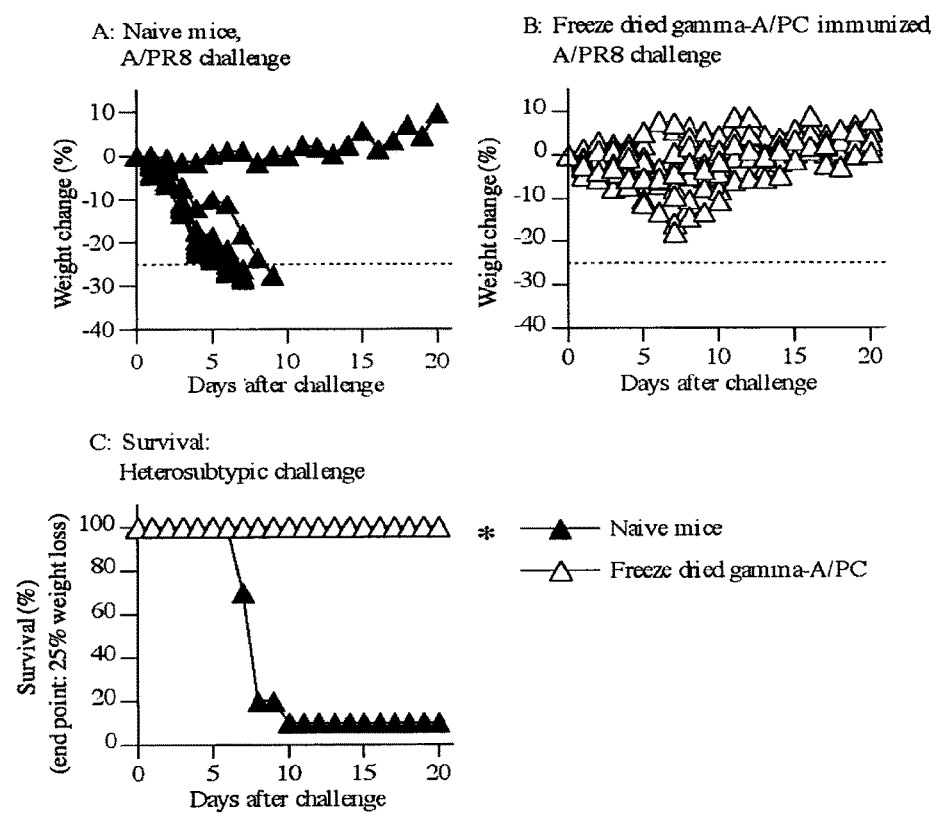
FIG. 29 provides a series of graphs illustrating that heterosubtypic protective properties of γ-irradiated A/PC are maintained after a dry freezing process. (A)=mock treated; (B)=challenged with freeze-dried γ-ray inactivated A/PR8; (C)=survival and weight loss after 20 days. * P<0.05 vs. control naïve group; Fisher's exact test.

A known shortcoming of the current liquid based influenza vaccine is the requirement of refrigerated storage that imposes a problem for vaccine distribution, particularly in developing countries. In an attempt to overcome the stringent storage requirement of the current influenza vaccine, freeze-drying γ-ray inactivated influenza virus was assessed as a means to curtail refrigeration requirements. Gamma-ray inactivated A/PC stock was freeze-dried and resuspended in distilled water immediately prior to intranasal administration ($3.2 \times 10^6$ PFU equivalent). Groups of 9-10 BALB/c mice were either mock treated or immunized with freeze-dried γ-ray inactivated A/PC and challenged with heterosubtypic strain A/PR8 ($7 \times 10^2$ PFU) at week 3-postimmunization. Survival and weight loss of mice was monitored daily for 20 days. The majority of mice lost less than 10% total body weight and only 2/10 mice lost over 10% total body weight showing mild symptoms. All vaccinated mice survived the heterosubtypic challenge with A/PR8 ($7 \times 10^2$ PFU) as opposed to 10% survival in naïve mice (FIGS. 29A, B & C). These data suggest that the freeze-drying process does not markedly reduce the ability of γ-ray inactivated A/PC to induce heterosubtypic immunity.

Superiority of γ-Ray Inactivated-Influenza Compared to Split Vaccine

A comparison of the cross-protective efficacy of the commercially available flu vaccine, Flu-vax, with gamma-irradiated purified influenza virus after intranasal vaccination in mice revealed the following:

|  | | Protection | |
|---|---|---|---|
|  | µg HA | pfu equiv. | Homosubtypic | Hetersubtypic |
| Flu-Vax | 3 | $9 \times 10^7$ | +− | −−− |
| γ-irradiated influenza vaccine | $4.5 \times 10^{-2}$ | $3 \times 10^6$ | +++ | ++ |

Accordingly, gamma-irradiated influenza virus is on an equivalent virus dose basis at least 30-100 times more efficient than the commercially available flu vaccine and is superior in quality to the present commercially available flu vaccine.

(iii) Discussion

The present study evaluated in a comparative setting the protective efficacy of three types of inactivation regimens; γ-irradiation, and formalin-, or UV-inactivation, to assess whether the currently used chemical inactivation method, used since 1945, is the most suitable choice for influenza vaccine preparation. It was shown that γ-ray inactivated A/PC ($3.2 \times 10^6$ PFU equivalent, 2300 HAU) had superior immunogenicity compared to the other sterilization methods, and confers a high level of protection against both homologous and heterosubtypic challenges. This superior protection was reflected in 100% survival and lower weight loss, which correlated with histological evaluations of lung tissues after infection as well as reduced lung viral load compared to naïve and formalin- or UV-inactivated-virus vaccinated mice. Similarly, single doses of a currently used trivalent influenza vaccine provided no protection against A/PC or A/PR8 challenges.

Three-fold higher doses of formalin-inactivated A/PC ($9.6 \times 10^6$ PFU equivalent, 2300 HAU) and multiple immunizations were required to gain the level of protection afforded by γ-ray inactivated A/PC. Furthermore, formalin-inactivated A/PC conferred protection only against homologous (and not against heterosubtypic) virus challenge. Therefore, an increase in dose and frequency of immunization only improves the strain-specific immunity of formalin-inactivated virus. It is important to note that for per virus particle inactivated, γ-ray inactivated virus is more immunogenic than formalin-inactivated virus since a formalin-inactivated virus preparation required three times more PFU for a comparable HAU dose and triple immunizations, as opposed to single priming for γ-irradiated A/PC, to obtain strain specific immunity. These findings demonstrate that γ-ray inactivation maintains superior antigenicity and immunogenicity relative to the other procedures. Thus γ-ray inactivated virus could induce immunity that is not only quantitatively but also qualitatively superior to virus preparations inactivated by formalin treatment or UV-irradiation.

In the event of a pandemic, a single dose regimen, as promised by γ-irradiated virus, would be incomparably more desirable than a multiple, high dose, formalin-inactivated influenza vaccine immunization regimens which also require adjuvants. Moreover, the fact that no adjuvants are required for γ-ray inactivated influenza suggests that reactogenicity problems are less likely to be encountered. Alum is most commonly used adjuvant for human vaccines but it has been proven to be ineffective in enhancing the immunogenicity of influenza vaccine antigens. In addition, alum skews the immune response towards T helper (Th) type 2-supported humoral immune responses which may reduce the effectiveness of γ-ray inactivated virus, as the latter is known to induce Th1-type cellular immune responses, including Tc cell responses that correlate with heterosubtypic protection. Furthermore the efficacy of γ-irradiated influenza virus is highlighted by the fact that after a single dose of intranasal priming, the immunized mice were able to resist heterosubtypic challenge doses of up to 50×LD50, for a period of up to 3 months, underscoring the robust immunity induced.

It is speculated that the cross protection induced by γ-irradiated virus is mediated by mucosal Tc cell responses. An alternative hypothesis is induction of cross-reactive secretory IgA antibodies to internal viral proteins. Some secretory IgA antibodies are capable of intracellular neutralization of influenza virus during transcytosis into the infected epithelial cells, and the present data suggests that cross-reactive Tc cells may be responsible for the cross protection observed here as other forms of inactivated influenza viruses, are unable to prime for influenza-immune Tc cell responses. Moreover, gamma-ray inactivation has less impact on hemagglutination activity than formalin or UV inactivation. γ-irradiated virus, retaining antigens similar to their native forms does appear to at least partially account for its superior immunogenicity. Intranasal administration targets the lung mucosa associated lymphoid organ for inducing immunity in the respiratory tract. However, a previously marketed intranasally administered influenza vaccine, was associated with an increase in the number of Bell's palsy cases—facial paralysis (see Mutsch, et al., (2004), "*Use of the inactivated intranasal influenza vaccine and the risk of Bell's palsy in Switzerland*", The New England journal of medicine, 350: 896-903) and consequently resulted in market withdrawal of this vaccine preparation. This adverse event has been attributed to the mucosal adjuvant used; *Escherichia coli* heat-labile toxin. Such safety concern would not be an issue with γ-ray inactivated influenza vaccine as it does not require the inclusion of potentially harmful adjuvants in its vaccine formulation.

Apart from the strong protective efficacy observed, several additional factors contribute to the attractiveness of γ-irradiation for influenza vaccines. Firstly, freeze dried γ-ray inactivated A/PC maintained its cross-protective property. Dry powder formulations will improve stability compared to liquid formulations under various storage conditions providing a significant advantage in distribution of the vaccine in an event of a pandemic. Secondly, the intranasal route of delivery, which requires little training or medical qualified personnel, would provide additional advantages for developing countries. Thirdly, γ-ray inactivated influenza vaccine would be comparatively easy and inexpensive to manufacture when compared to other vaccine production processes. Most importantly with regards to manufacturing considerations and availability, the robust heterosubtypic protection induced by γ-ray inactivated influenza may render annual reformulation of influenza vaccines obsolete.

Example 6: Preparation of Influenza Virus for Gamma-Irradiation

Viruses used in current influenza vaccines are generally purified before attenuation using ultracentrifugation which has been associated with loss of viral-antigen and/or destruction of virion structure. The induction of cytotoxic T cell responses by γ-irradiated influenza vaccines will benefit from an alternative method of virus purification (differential/tangential filtration) prior to γ-irradiation which preserves the integrity of virion structure.

It is envisaged that virus stocks will be clarified using centrifugation at low speed (~3000 rpm) and used in size exclusion based centrifugation. Clarified stocks will be spun through filtering device with pore size 50-80 nm. In general, the size of influenza virus will be 80-120 nm. Thus, variable pore size (e.g less than 80 nm) will be used to purify influenza virus at low centrifugation speeds (4000-10000 rpm) (variable speed can be used) at 4° C. for as long as needed to get liquid through the filter. The initial virus stock liquid flow path on the upstream side of the filter will be tangential or across the filter surface. Upon centrifugation, the majority of the liquid will pass through the filter (permeate), while a small portion will be retained in the central reservoir as the retentate (containing all the virus).

The retentate will be rediluted with PBS (normal saline, or any other media) that may contain sugar (dextran, sucrose) to maintain the osmotic pressure and consequently virus integrity. These diluted preparations may be filtered again, if needed. Concentrated virus from the final centrifugation step will be treated by γ-irradiation as described in the Examples above. Free radical scavengers, such as Ascorbate, can be added to purified virus stocks prior to irradiation to reduce possible damage to viral proteins while inactivating viral genome during γ-irradiation.

For example, the following protocol may be utilised for the purification of intact influenza virus to be used for γ-irradiation:

1. influenza virus stock can be harvested from embryonated eggs, or in vitro tissue culture.
2. using filter devices with a cut off of 300 Kd, virus stock can be clarified by centrifuging at 300 g for 30 minutes at 4° C. causing both influenza viruses and proteins of the allentoic fluids (or tissue culture media) to pass through the filter.
3. using filter devices with a cut off of 100 Kd, clarified virus stock can be purified by centrifuging at 300 g for 30 minutes at 4° C. In this step influenza viruses do not pass through the filter (thereby concentrating the virus) on one side of the filter.
4. concentrated virus can be washed with normal saline (or any buffered media) to remove any remaining egg proteins (washing may be performed as many times as required). Washing can be performed by diluting the concentrated viruses with saline and centrifuging as described in step 3 above.
5. the final virus concentrate will contain intact virion.

In general, pore size cut off levels for filtering devices used in the above technique can be designed to match virion size of 80-120 nm. All procedures may be conducted at 4° C. and no ultracentrifugation is required. Viral infectivity can be tested for original stock and final products. Prior knowledge of virus titres and volume can facilitate estimation of level of concentration. The purity of the final product can be determined using standard biochemical analyses.

INCORPORATION BY REFERENCE

This application claims priority from U.S. provisional patent application No. 61/085,802 filed on 1 Aug. 2008, the entire contents of which are incorporated herein by reference.

The invention claimed is:

1. A method for inducing or enhancing cross-reactive T cell responses against multiple influenza virus subtypes in a subject, the method comprising intranasally administering to the subject a therapeutically effective amount of a gamma-irradiated influenza virus without an adjuvant, wherein said gamma-irradiated influenza virus is not prepared using ultracentrifugation.

2. The method according to claim 1, wherein said multiple influenza virus subtypes comprise one or more of human, avian, swine, canine or equine influenza virus subtypes.

3. The method according to claim 1, wherein said multiple influenza virus subtypes comprise influenza A subtype HPAI A(H5N1).

4. The method according to claim 1, wherein said multiple influenza virus subtypes comprise influenza A subtype H1N1 09 Swine Flu.

5. The method according to claim 1, wherein said gamma-irradiated influenza virus is prepared in a freeze-dried form.

6. The method according to claim 1, wherein said gamma-irradiated influenza virus is prepared from a virus stock purified by tangential/cross-flow filtration.

7. The method according to claim 1, wherein said gamma-irradiated influenza virus is generated by gamma-irradiating a frozen viral preparation.

8. The method according to claim 1, wherein said gamma-irradiated influenza virus is selected from the group consisting of A/WSN [H1N1], A/PR8 [H1N1], A/JAP [H2N2] and A/PC [H3/N2].

9. The method according to claim 1, wherein said gamma-irradiated influenza virus is generated by exposing said virus to a total dose of between about $6.5 \times 10^4$ rad and about $2 \times 10^7$ rad of gamma rays.

10. The method according to claim 1, wherein said gamma-irradiated influenza virus is generated by exposing said virus to a total dose of about $1 \times 10^6$ rad of gamma rays.

\* \* \* \* \*